United States Patent
Erlanson et al.

(10) Patent No.: US 7,214,487 B2
(45) Date of Patent: May 8, 2007

(54) METHODS FOR IDENTIFYING COMPOUNDS THAT MODULATE ENZYMATIC ACTIVITIES BY EMPLOYING COVALENTLY BONDED TARGET-EXTENDER COMPLEXES WITH LIGAND CANDIDATES

(75) Inventors: Daniel A. Erlanson, San Francisco, CA (US); Robert S. McDowell, San Francisco, CA (US); Stig Hansen, El Cerrito, CA (US)

(73) Assignee: Sunesis Pharmaceuticals, Inc., South San Francisco, CA (US)

( * ) Notice: Subject to any disclaimer, the term of this patent is extended or adjusted under 35 U.S.C. 154(b) by 506 days.

(21) Appl. No.: 10/374,499

(22) Filed: Feb. 25, 2003

(65) Prior Publication Data

US 2004/0005632 A1   Jan. 8, 2004

Related U.S. Application Data

(60) Continuation-in-part of application No. 10/121,216, filed on Apr. 10, 2002, which is a continuation-in-part of application No. 09/981,547, filed on Oct. 17, 2001, which is a division of application No. 09/105,372, filed on Jun. 26, 1998, now Pat. No. 6,335,155, which is a continuation-in-part of application No. 09/990,421, filed on Nov. 21, 2001, now Pat. No. 6,919,178.

(60) Provisional application No. 60/377,034, filed on May 1, 2002, provisional application No. 60/252,294, filed on Nov. 21, 2000.

(51) Int. Cl.
C12Q 1/68 (2006.01)
C40B 20/08 (2006.01)
C40B 50/08 (2006.01)

(52) U.S. Cl. .................. 435/6; 435/4; 435/7.1
(58) Field of Classification Search ............... None
See application file for complete search history.

(56) References Cited

U.S. PATENT DOCUMENTS 5,367,058 A * 11/1994 Pitner et al. ............. 530/391.9
6,335,155 B1   1/2002 Wells et al.
6,811,966 B2 * 11/2004 Wells et al. ................ 435/4
6,919,178 B2 *  7/2005 Erlanson et al. ............ 435/6
2002/0155505 A1* 10/2002 Wells et al. ............... 435/7.1

FOREIGN PATENT DOCUMENTS

| WO | WO 02/42773 A2 | 5/2002 |
| WO | WO 03/014072 A1 | 2/2003 |
| WO | WO 03/014308 A2 | 2/2003 |
| WO | WO 03/046200 A2 | 6/2003 |

OTHER PUBLICATIONS

Yasothornsrkul, S.; Aaron, W.; Toneff, T.; Hook, V. Y. H. Evidence for the Proenkephalin Processing Enzyme Prohormone thiol Protease (PTP) as a Multicatalytic Cysteine Protease Complex. Biochemistry 1999, 38, 7421-7430.*

Burke, T., et al., "Phosphoryltyrosyl Mimetics in the Design of Peptide-Based Signal Transduction Inhibitors", Biopolymers (Peptide Science), vol. 60, 2001, pp. 32-44.

Erlanson, D., et al., "Discovery of a New Phosphotyrosine Mimetic for PTP1B Using Breakaway Tethering", Journal of American Chemical Society, Vo. 125, No. 19, 2003, 5602-5603.

Szczepankiewicz, B., et al., "Discovery of a Potent, Selective Protein Tyrosine Phosphatase 1B Inhibitor Using a Linked-Fragment Strategy", Journal of American Chemical Society, Vo. 125, No. 14, 2003, 4087-4096.

Daniel A. Erlanson, et al., "Site-directed Ligand Discovery", PNAS, Aug. 15, 2000, vol. 97, No. 17, pp. 9367-9372.

Betley et al. Direct screening for Phosphatase Activity by Turnover-Based Capture of Protein Catalysts, Angew. Chem. Int. Ed. 2002, vol. 41, No. 5, pp. 775-777.

Erlanson et al. In-Situ Assembly of Enzyme Inhibitors Using Extended Tethering. Nature Biotechnology. Mar. 2003, vol. 21, pp. 308-314.

* cited by examiner

*Primary Examiner*—Jon Epperson
(74) *Attorney, Agent, or Firm*—Heller Ehrman LLP

(57) ABSTRACT

The present invention relates to methods for identifying compounds that modulate enzymatic activity by contacting covalently bonded PTP-extender complexes or modified covalently bonded PTP-extender complexes with ligand candidates.

19 Claims, 4 Drawing Sheets

```
                1                                                          50
PTP-1B   ..  MEMEKEFEQI  DK SGSWAAIY  QDIRHEASDF  PCRVAKLPKN  KNRNRYRDVS
hTC-ptp      MPTTIEREFEEL DT QRRWQPLY  LEIRNESHDY  PHRVAKFPEN  RNRNRYRDVS
LAR          PITDLADNIERL KANDGLKFSQE  YESIDPGQQF  TWENSNLEVN  KPKNRYANVI 51                                                          100
PTP-1B       PFDHSRIKLH  QED     NDYINAS  LIKMEEAQRS  YILTQGPLPN  TCGHFWEMVW
hTC-ptp      PYDHSRVKLQ  NAE     NDYINAS  LVDIEEAQRS  YILTQGPLPN  TCCHFWLMVW
LAR          AYDHSRVILT  SIDGVPGSDYINAN  YIDGYRKQNA  YIATQGPLPE  TMGDFWRMVW 101                                                         150
PTP-1B       EQKSRGVVML  NRVMEKGSLK  CAQYWPQKEE  KEMIFEDTNL  KLTLISEDIK
hTC-ptp      QQKTKAVVML  NRIVEKESVK  CAQYWP.TDD  QEMLFKETGF  SVKLLSEDVK
LAR          EQRTATVVMM  TRLEEKSRVK  CDQYWPARG.....TETCGLI  QVTLLDTVEL 151                                                         200
PTP-1B       SYYTVRQLEL  ENLTTQETRE  ILHFHYTTWP  DFGVPESPAS  FLNFLFKVRE
hTC-ptp      SYYTVHLLQL  ENINSGETRT  ISHFHYTTWP  DFGVPESPAS  FLNFLFKVRE
LAR          ATYTVRTFAL  HKSGSSEKRE  LRQFQFMAWP  DHGVPEYPTP  ILAFLRRVKA 201                                                         250
PTP-1B       SGSLSPEHGP  VVVHCSAGIG  RSGTFCLADT  CLLLMDKRKD  PSSVDIKKVL
hTC-ptp      SGSLNPDHGP  AVIHCSAGIG  RSGTFSLVDT  CLVLMEKGDD.. .INIKQVL
LAR          CN. PLDAGP  MVVHCSAGVG  RTGCFIVID. ..AMLERMKH  EKTVDIYGHV 251                                        298
PTP-1B       LEMRKFRMGL  IQTADQLRFS  YLAVIEGAKF  IMGDSSVQDQ  WKELSHED
hTC-ptp      LNMRKYRMGL  IQTPDQLRFS  YMAIIEGAKC  IKGDSSIQKR  WKELSKED
LAR          TCMRSQRNYM  VQTEDQYVFI  HEALLEAATC  GHTEVPARNL  YAHIQKLG
```

METHODS FOR IDENTIFYING COMPOUNDS THAT MODULATE ENZYMATIC ACTIVITIES BY EMPLOYING COVALENTLY BONDED TARGET-EXTENDER COMPLEXES WITH LIGAND CANDIDATES

RELATED APPLICATIONS

This application claims the priority under 35 USC 119(e) of U.S. Provisional Application No. 60/377,034, filed May 1, 2002, and is a continuation-in-part application of, and claims priority under 35 U.S.C. §120 to, U.S. application Ser. No. 10/121,216 filed Apr. 10, 2002, which is a continuation-in-part of, and claims priority under 35 U.S.C. §120 to, U.S. application Ser. No. 09/981,547, filed on Oct. 17, 2001, which is a divisional application of, and claims priority under 35 U.S.C. §120 to, U.S. application Ser. No. 09/105,372, filed on Jun. 26, 1998, now U.S. Pat. No. 6,335,155, and which is a continuation-in-part of, and claims priority under 35 U.S.C. §120 to, U.S. application Ser. No. 09/990,421, filed on Nov. 21, 2001, now U.S. Pat. No. 6,919,178 which asserts priority under 35 U.S.C. §119 to U.S. Provisional Application 60/252,294 filed Nov. 21, 2000, all of which are incorporated herein by reference.

BACKGROUND

The drug discovery process usually begins with massive functional screening of compound libraries to identify modest affinity leads for subsequent medicinal chemistry optimization. However, not all targets of interest are amenable to such screening. In some cases, an assay that is amenable to high throughput screening is not available. In other cases, the target can have multiple binding modes such that any result from such screens is ambiguous and difficult to interpret. Still in other cases, the assay conditions for high throughput assays are such that they are prone to artifacts. As a result, alternative methods for ligand discovery are needed that do not necessarily rely on functional screens.

DESCRIPTION OF THE FIGURES

FIG. 3 is one embodiment of an alignment of the first 298 residues of PTP-1B (SEQ ID NO: 7) and the corresponding residues for TC-PTP (SEQ ID NO: 8) and LAR (SEQ ID NO: 9). All three PTPs are human versions of the enzymes.

FIG. 4A is the spectrum for the R47 mutant of PTP-1B. FIG. 4B is the spectrum for the R47 mutant of PTP-1B that has been modified with the extender wherein a covalent bond is formed between the thiol (on residue 47 and the first functionality). This complex is referred to as the PTP-1B-extender complex. FIG. 4C is the spectrum wherein the cleavable linker is cleaved thereby exposing the second functionality (in this case a thiol) and releasing the phosphotyrosine mimetic. This complex is referred to as the modified PTP-1B-extender complex.

DESCRIPTION OF THE PREFERRED EMBODIMENTS

Figure 1:
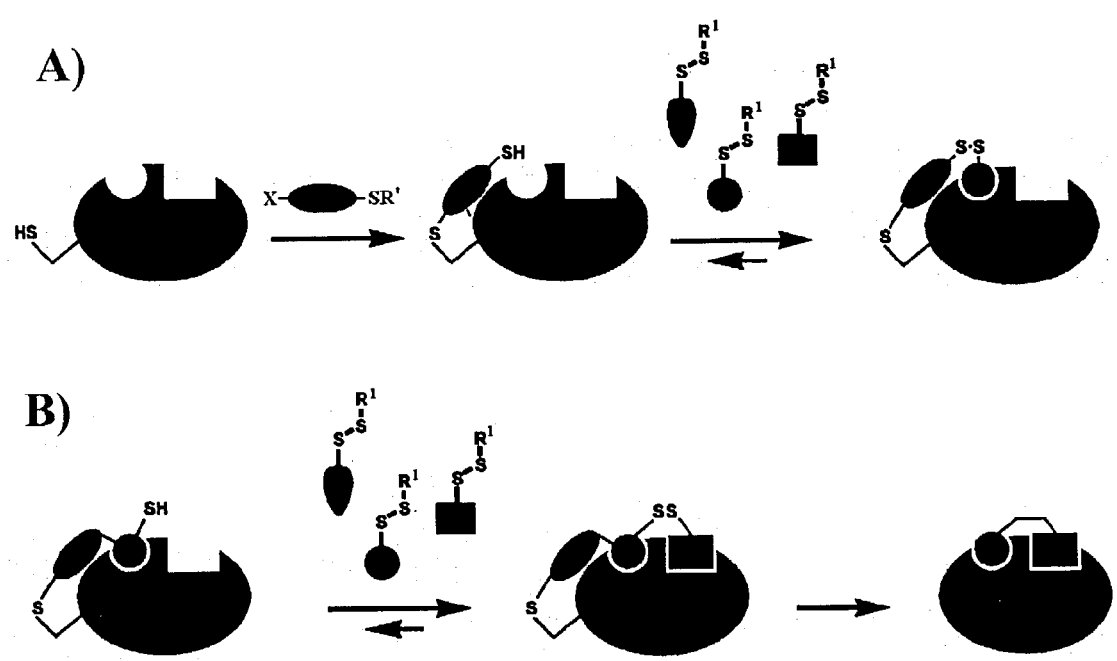
FIG. 1 is a schematic illustration of one embodiment of the tethering method.

The present invention relates to the use of "tethering" to identify compounds that modulate enzymatic activity.

Unless defined otherwise, technical and scientific terms used herein have the same meaning as commonly understood by one of ordinary skill in the art to which this invention belongs. References, such as Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

In one aspect of the present invention, compounds are provided. Unless explicitly or implicitly indicated otherwise, these compounds can be in the form of an individual enantiomer, diasteromer, geometric isomer, or mixtures thereof. In the case of compounds containing double bonds, these double bonds can be either Z or E or a mixture thereof, unless otherwise indicated.

Definitions

The definition of terms used herein include:

The term "aliphatic" or "unsubstituted aliphatic" refers to a straight, branched, cyclic, or polycyclic hydrocarbon and includes alkyl, alkenyl, alkynyl, cycloalkyl, cycloalkenyl, and cycloalkynyl moieties.

The term "alkyl" or "unsubstituted alkyl" refers to a saturated hydrocarbon.

The term "alkenyl" or "unsubstituted alkenyl" refers to a hydrocarbon with at least one carbon-carbon double bond.

The term "alkynyl" or "unsubstituted alkynyl" refers to a hydrocarbon with at least one carbon-carbon triple bond.

The term "aromatic" or "unsubstituted aromatic" refers to moieties having at least one aryl group. The term also includes aliphatic modified aryls such as alkylaryls and the like.

The term "aryl" or "unsubstituted aryl" refers to mono or polycyclic unsaturated moieties having at least one aromatic ring. The term includes heteroaryls that include one or more heteroatoms within the at least one aromatic ring. Illustrative examples of aromatics include: phenyl, naphthyl, tetrahydronaphthyl, indanyl, indenyl, pyridyl, pyrazinyl, pyrimidinyl, pyrrolyl, pyrazolyl, imidazolyl, thiazolyl, oxazolyl, isooxazoly, thiadiazolyl, oxadiazolyl, thiophenyl, furanyl, quinolinyl, isoquinolinyl, and the like.

The term "substituted" when used to modify a moiety refers to a substituted version of the moiety where at least one hydrogen atom is substituted with another group including but not limited to: aliphatic; aryl, alkylaryl, F, Cl, I, Br, —OH; —NO$_2$; —CN; —CF$_3$; —CH$_2$CF$_3$; —CH$_2$Cl; —CH$_2$OH; —CH$_2$CH$_2$OH; —CH$_2$NH$_2$; —CH$_2$SO$_2$CH$_3$; —OR$^x$; —C(O)R$^x$; —COOR$^x$; —C(O)N(R$^x$)$_2$; —OC(O)R$^x$; —OCOOR$^x$; —OC(O)N(R$^x$)$_2$; —N(R$^x$)$_2$; —S(O)$_2$R$^x$; and —NR$^x$C(O)R$^x$ where each occurrence of R$^x$ is independently hydrogen, substituted aliphatic, unsubstituted aliphatic, substituted aryl, or unsubstituted aryl. Additionally, substitutions at adjacent groups on a moiety can together form a cyclic group.

The term "ligand candidate" or "candidate ligand" refers to a compound that possesses or has been modified to possess a reactive group that is capable of forming a covalent bond with a complimentary or compatible reactive group on a target enzyme. The reactive group on either the ligand candidate or the target enzyme can be masked with, for example, a protecting group.

The phrase "protected thiol" or "masked thiol" as used herein refers to a thiol that has been reacted with a group or molecule to form a covalent bond that renders it less reactive and which may be deprotected to regenerate a free thiol.

The phrase "reversible covalent bond" as used herein refers to a covalent bond that can be broken, preferably under conditions that do not denature the target. Examples include, without limitation, disulfides, Schiff-bases, thioesters, coordination complexes, boronate esters, and the like.

The phrase "reactive group" is a chemical group or moiety providing a site at which a covalent bond can be made when presented with a compatible or complementary reactive group. Illustrative examples are —SH that can react with another —SH or —SS— to form a disulfide; an —$NH_2$ that can react with an activated —COOH to form an amide; an —$NH_2$ that can react with an aldehyde or ketone to form a Schiff base and the like.

The phrase "reactive nucleophile" as used herein refers to a nucleophile that is capable of forming a covalent bond with a compatible functional group on another molecule under conditions that do not denature or damage the target enzyme. The most relevant nucleophiles are thiols, alcohols, and amines.

The phrase "site of interest" refers to any site on a target enzyme in which a ligand can bind.

The Tethering Method

Tethering is a method of ligand identification that relies upon the formation of a covalent bond between a reactive group on a target and a complimentary reactive group on a potential ligand. The tethering method is described in U.S. Pat. No. 6,335,155; PCT Publication Nos. WO 00/00823 and WO 02/42773; U.S. Ser. No. 10/121,216 entitled METHODS FOR LIGAND DISCOVERY by inventors Daniel Erlanson, Andrew Braisted, and James Wells (corresponding PCT Application No. US02/13061); and Erlanson et al., *Proc. Nat. Acad. Sci USA* 97:9367–9372 (2000), which are all incorporated by reference. The resulting covalent complex is termed a target-ligand conjugate. Because the covalent bond is formed at a pre-determined site on the target (e.g., a native or non-native cysteine), the stoichiometry and binding location are known for ligands that are identified by this method.

Once formed, the ligand portion of the target-ligand conjugate can be identified using a number of methods. In preferred embodiments, mass spectrometry is used. Mass spectrometry detects molecules based on mass-to-charge ratio (m/z) and can resolve molecules based on their sizes (reviewed in Yates, *Trends Genet.* 16: 5–8 [2000]). The target-ligand can be detected directly in the mass spectrometer or fragmented prior to detection. Alternatively, the compound can be liberated within the mass spectrophotometer and subsequently identified. Moreover, mass spectrometry can be used alone or in combination with other means for detection or identifying the compounds covalently bound to the target. Further descriptions of mass spectrometry techniques include Fitzgerald and Siuzdak, *Chemistry & Biology* 3: 707–715 [1996]; Chu et al., *J. Am. Chem. Soc.* 118: 7827–7835 [1996]; Siudzak, *Proc. Natl. Acad. Sci. USA* 91: 11290–11297 [1994]; Burlingame et al., *Anal. Chem.* 68: 599R-651R [1996]; Wu et al., *Chemistry & Biology* 4: 653–657 [1997]; and Loo et al., *Am. Reports Med. Chem.* 31: 319–325 [1996]).

Alternatively, the target-compound conjugate can be identified using other means. For example, one can employ various chromatographic techniques such as liquid chromatography, thin layer chromatography and the like for separation of the components of the reaction mixture so as to enhance the ability to identify the covalently bound molecule. Such chromatographic techniques can be employed in combination with mass spectrometry or separate from mass spectrometry. One can also couple a labeled probe (fluorescently, radioactively, or otherwise) to the liberated compound so as to facilitate its identification using any of the above techniques. In yet another embodiment, the formation of the new bonds liberates a labeled probe, which can then be monitored. A simple functional assay, such as an ELISA or enzymatic assay can also be used to detect binding when binding occurs in an area essential for what the assay measures. Other techniques that may find use for identifying the organic compound bound to the target molecule include, for example, nuclear magnetic resonance (NMR), surface plasmon resonance (e.g., BIACORE), capillary electrophoresis, X-ray crystallography, and the like, all of which will be well known to those skilled in the art.

THE PRESENT INVENTION

The present invention relates to a form of tethering that relies on the use of an extender that is attached to a target outside of a target's site of interest. Because the extender is attached to the target outside of the site of interest, the potential for structural or functional perturbation within the site of interest is minimized. In addition, target mutants can be assessed for structural and functional integrity using functional screens.

In one aspect of the present invention, a method is provided comprising:

a) providing a target having a reactive nucleophile located outside of a site of interest;

b) contacting the target with an extender thereby forming a target-extender complex wherein the extender comprises a first functionality that forms a first covalent bond with the nucleophile and a second functionality that is capable of forming a second covalent bond;

c) contacting the target-extender complex with a candidate ligand that comprises a group that is capable of forming a second covalent bond with the second functionality;

d) forming a second covalent bond between the target-extender complex and the candidate ligand thereby forming a target-extender-ligand conjugate; and, e) identifying the candidate ligand present in the target-extender-ligand conjugate.

In one embodiment, the target comprises a —OH as the reactive nucleophile and the extender comprises a first functionality that is capable of forming a covalent bond with the reactive nucleophile on the target and a second functionality that is capable of forming a disulfide bond. In another embodiment, the reactive nucleophile on the target is a —OH from a serine, threonine, or tyrosine that is part of the naturally occurring protein sequence. In another embodiment, the reactive nucleophile on the target is an engineered —OH group where mutagenesis was used to mutate a naturally occurring amino acid to a serine, threonine, or tyrosine. In another embodiment, the first functionality of the extender is a boronic acid and the second functionality is a —SH or a masked —SH. An illustration of a masked disulfide is a thioester of the formula —SC(=O)$R^1$ or a disulfide of the formula —$SSR^1$ where $R^1$ is unsubstituted $C_1$–$C_{10}$ aliphatic, substituted $C_1$–$C_{10}$ aliphatic, unsubstituted aromatic, or substituted aromatic. In one embodiment, the masked disulfide is a thioester of the formula —SC(=O)R$^1$ where R$^1$ is C$_1$–C$_5$ alkyl. In another embodiment, the masked thiol is a disulfide of the formula —SSR$^2$R$^3$ where R$^2$ is C$_1$–C$_5$ alkyl and R$^3$ is NH$_2$, OH, or COOH. In another embodiment, the masked thiol is a disulfide of the formula —SSCH$_2$CH$_2$OH. In yet another embodiment, the masked thiol is a disulfide of the formula —SSCH$_2$CH$_2$NH$_2$.

In another embodiment, the target comprises a —SH as the reactive nucleophile and the extender comprises a first functionality that is capable of forming a covalent bond with the reactive nucleophile on the target and a second functionality that is capable of forming a disulfide bond. In one embodiment, the reactive nucleophile on the target is a naturally occurring —SH from a cysteine that is part of the naturally occurring protein sequence. In another embodiment, the reactive nucleophile on the target is an engineered —SH group where mutagenesis was used to mutate a naturally occurring amino acid to a cysteine.

In another embodiment, the target protein possesses a masked —SH in the form of a disulfide as the reactive nucleophile. In another embodiment, the target protein possesses a cysteine where the thiol is masked as a disulfide. In another embodiment, the target protein possesses a cysteine where the thiol is masked as a disulfide bond with another cysteine. In another embodiment, the target protein possesses a cysteine where the thiol is masked as a disulfide bond with glutathione. In another embodiment, the target protein possesses a cysteine where the thiol is masked as a disulfide of the formula —SSR$^1$ where R$^1$ is as previously described.

In another embodiment, the first functionality, the second functionality or both are each independently a —SH or a masked —SH. An illustrative example of a masked thiol is a thioester of the formula —SC(=O)R$^1$ or a disulfide of the formula —SSR$^1$ where R$^1$ is as previously described. In this embodiment, the covalent bond formed between the target and the extender is a disulfide bond and thus is a reversible covalent bond. In one variation of the method, the target is contacted with the extender prior to contacting the target-extender complex with one or more candidate ligands. In another variation, the target is contacted with a pool comprising the extender and one or more candidate ligands.

In another aspect of the present invention, a method is provided comprising:
  a) providing a target having a reactive thiol located outside of a site of interest;
  b) contacting the target with an extender thereby forming a target-extender complex wherein the extender comprises a first functionality that forms a covalent bond with the reactive thiol and a second functionality that is capable of forming a disulfide bond;
  c) contacting the target-extender complex with a candidate ligand that comprises a group that is capable of forming a disulfide bond with the second functionality;
  d) forming a disulfide bond between the target-extender complex and the candidate ligand thereby forming a target-extender-ligand conjugate; and,
  e) identifying the candidate ligand present in the target-extender-ligand conjugate.

In one embodiment, the reactive thiol on the target is a naturally occurring —SH from a cysteine that is part of the naturally occurring protein sequence. In another embodiment, the reactive thiol on the target is an engineered —SH group where mutagenesis was used to mutate a naturally occurring amino acid to a cysteine.

In another embodiment, the target protein possesses a masked —SH in the form of a disulfide as the reactive thiol.

In another embodiment, the target protein possesses a cysteine where the thiol is masked as a disulfide. In another embodiment, the target protein possesses a cysteine where the thiol is masked as a disulfide bond with another cysteine. In another embodiment, the target protein possesses a cysteine where the thiol is masked as a disulfide bond with glutathione. In another embodiment, the target protein possesses a cysteine where the thiol is masked as a disulfide of the formula —SSR$^1$ where R$^1$ is as previously described.

In another embodiment, the covalent bond between the reactive thiol and the first functionality is an irreversible covalent bond. In another embodiment, the covalent bond between the reactive thiol and the first functionality is a reversible covalent bond.

In another embodiment, the second functionality is a masked thiol and the method additionally comprises unmasking the second functionality subsequent to forming a target-extender complex. In another embodiment, the second functionality is a thioester and the method additionally comprises unmasking the thioester by converting the thioester into a thiol.

In another embodiment, the target-extender complex is contacted with a candidate ligand in the presence of a reducing agent. Illustrative examples of suitable reducing agents include but are not limited to: cysteine, cysteamine, dithiothreitol, dithioerythritol, glutathione, 2-mercaptoethanol, 3-mercaptoproprionic acid, a phosphine such as tris-(2-carboxyethyl-phosphine) ("TCEP"), or sodium borohydride. In one embodiment, the reducing agent is 2-mercaptoethanol. In another embodiment, the reducing agent is cysteamine. In another embodiment, the reducing agent is glutathione. In another embodiment, the reducing agent is cysteine.

In another embodiment, the first functionality is a group that is capable of forming an irreversible covalent bond with the reactive thiol of the target under conditions that do not denature the target and the second functionality is a —SH or a masked —SH. A particularly comprehensive discussion of suitable groups is found in Powers et al., *Chem Rev* 102: 4639–4750 (2002) which is incorporated herein by reference. In one embodiment, the first functionality is a group capable of undergoing SN2-like addition. Illustrative example of such extenders include: (i) α-halo acids such as

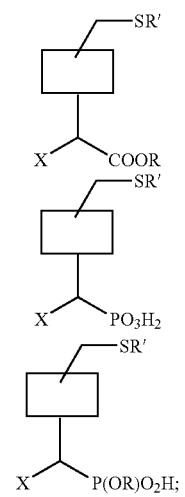

(ii) fluorophosphonates such as

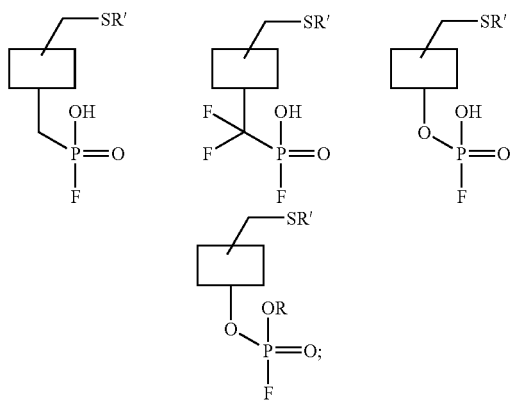

(iii) epoxides such as

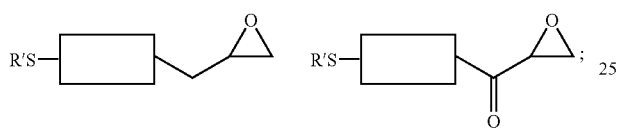

(iv) aziridines such as

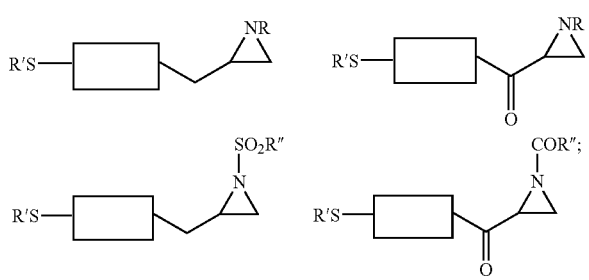

(v) thiiranes such as

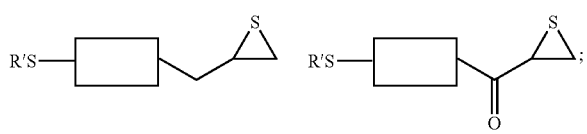

(vi) halomethyl ketones/amides such as

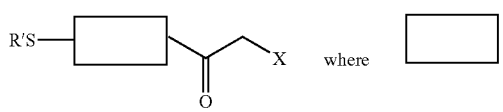

and R are each independently unsubstituted $C_1$–$C_{20}$ aliphatic, substituted $C_1$–$C_{20}$ aliphatic, unsubstituted aryl, and substituted aryl; R' is H, —$SR^1$ wherein $R^1$ has been previously defined; and X is a leaving group. Illustrative examples of include halogen, $N_2$, OR, —P(=O)Ar2, —NO(C=O)R, —(C=O)R, —O(C=O)R, and —SR.

In another embodiment, the first functionality is a group capable of undergoing SN aryl like addition. Illustrative examples of suitable groups include 7-halo-2,1,3-benzoxadiazaoles, and ortho/para nitro substituted halobenzenes such as

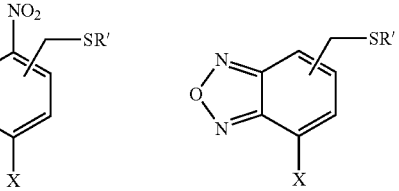

where R' and X are as previously defined.

In another embodiment, the first functionality is a group capable of undergoing Michael-type addition. Illustrative examples of suitable groups include any moiety that includes a double or triple bond adjacent to an electron withdrawing system such as a carbonyl, imines, quinines, CN, $NO_2$, —S(=O)—, and vinyl sulfones. Illustrative examples of such extenders include:

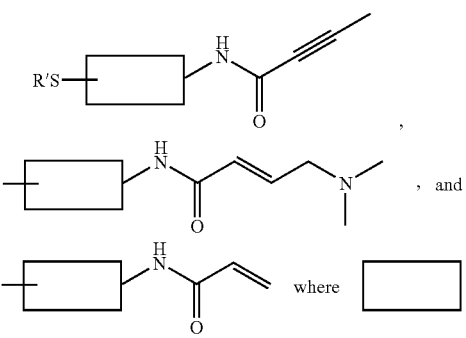

and R' are as previously defined.

FIG. 1A illustrates one embodiment of tethering using an extender that is attached to a target outside of the site of interest. As shown, a target is provided with a reactive group (in this case, a thiol) that is located outside of the site of interest (depicted as a circular indentation). An extender (depicted by an oval) having a first functionality (X) and a second functionality (in this case, SR'— a thiol or a masked thiol where R' is H, $SR^1$, SC(=O)$R^1$) is attached to the target via a covalent bond between the target's reactive group and the first functionality thereby forming a target-extender complex. The second functionality is used to probe the site of interest by contacting the target-extender complex with a candidate ligand. If the candidate ligand possesses an affinity for the site of interest, a second covalent bond is formed between the target-extender complex and the candidate ligand thereby forming a target-extender-ligand conjugate. Ligands with binding affinity for the site of interest are identified by analyzing the resulting target-extender-ligand conjugates.

Once a ligand is identified for the site of interest, it in turn can be used to probe an adjacent site in situations where such sites exist. In such a case, the adjacent site becomes a new site of interest in a subsequent round of tethering.

One approach for using ligand-binding information in an extended tether method is illustrated in FIG. 1B. As shown, the original extender is modified in view of known ligand information. This information can arise from a previous tether experiment or other known methods. The modified extender primarily differs from the original extender by the incorporation of the binding determinant (depicted by a circle), the portion of the ligand (or candidate ligand) possessing binding affinity for the original site of interest, and optionally, the location of the second functionality. As with the original extender, the modified extender possesses a first functionality that forms a covalent bond with a reactive group outside of the site of interest. The second functionality is located such that it is in a position to probe a site (depicted by a rectangular indentation) adjacent to the original site of interest (depicted by a circular indentation). The modified extender then is used in a similar manner as previously described. Once a second binding determinant (depicted by a rectangle) is identified, the first and second binding determinants are merged into a composite compound. As it can be seen, the original extender (depicted by an oval) does not need to be incorporated into the composite compound.

In another aspect of the present invention, a tethering method is provided for use where a target includes a reactive nucleophile within a site of interest and where there is an advantage to preserving this nucleophile. Typically, this first reactive nucleophile is an active site residue and scrubbing this residue (mutating it to an inert amino acid) would not be compatible with preserving enzymatic function. As with the previous method, a reactive nucleophile (a second reactive nucleophile) outside of the site of interest is used for tethering. An extender is used that attaches to the target via the second reactive nucleophile outside of the site of interest. The extender attaches to the second reactive nucleophile instead of the first reactive nucleophile because the extender also includes a binding determinant that is specific for the site of interest. This binding determinant functions as a temporary plug that is subsequently cleaved revealing a latent functionality. Tethering then proceeds as previously described using the latent functionality to explore the now-unplugged site of interest.

Thus, the method comprises:
a) providing a target having a first reactive nucleophile located inside of the site of interest and a second reactive nucleophile located outside of a site of interest;
b) contacting the target with an extender thereby forming a target-extender complex, the extender comprising a first functionality and a latent second functionality, a cleavable linker and a binding determinant wherein the first functionality forms a first covalent bond with the second reactive nucleophile and the binding determinant binds to the site of interest;
c) cleaving the extender at the cleavable linker thereby forming a modified target-extender complex by exposing the second functionality and releasing the binding determinant from the site of interest;
d) contacting the modified target-extender complex with a candidate ligand that comprises a group that is capable of forming a second covalent bond with the second functionality;
e) forming a second covalent bond between the modified target-extender complex and the candidate ligand thereby forming a target-extender-ligand conjugate; and,
f) identifying the candidate ligand present in the target-extender-ligand conjugate.

In one embodiment, the first reactive nucleophile is a —OH and the second reactive nucleohile is a —SH. In another embodiment, the first reactive nucleophile is a —SH and the second reactive nucleohile is a —OH. In another embodiment, both the first and second reactive nucleophiles are each —OH. In another embodiment, both the first and second reactive nucleophiles are each —SH.

In another embodiment, the extender comprises: a) a first functionality that is capable of forming an irreversible covalent bond with the second reactive nucleophile on the target; and b) a latent second functionality that is capable of forming a disulfide bond.

Figure 2:
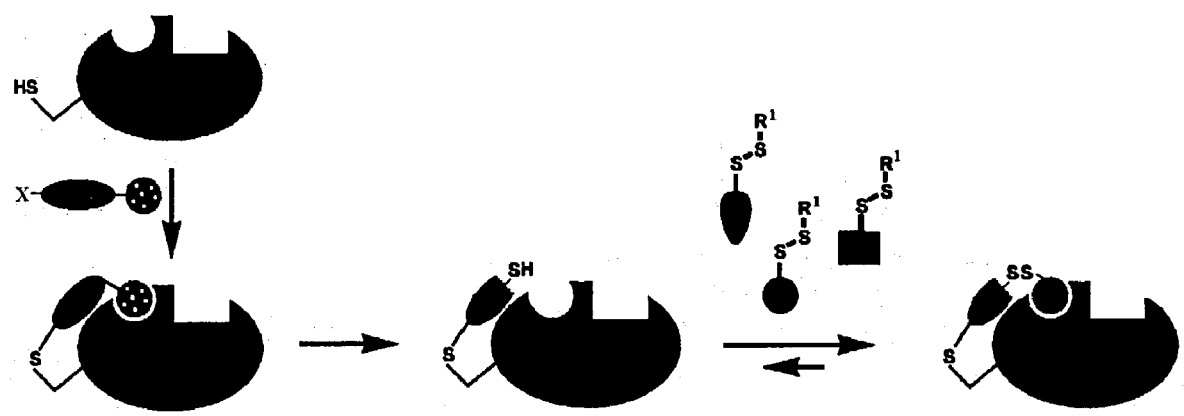
FIG. 2 is a schematic illustration of another embodiment of the tethering method.

FIG. 2 illustrates one embodiment of this form of tethering wherein the target comprises a first reactive nucleophile in the site of interest and a second reactive nucleophile outside of the site of interest. As shown, a target is provided with a site of interest (depicted as a circular indentation), a first reactive nucleophile in the site of interest (not pictured), and a second reactive nucleophile (in this case, a thiol) that is located outside of the site of interest. An extender,

having a first functionality (X), a latent second functionality, a cleavable linker and a binding determinant (circle with dots), is attached to the target via a covalent bond between the target's reactive group and the first functionality thereby forming a target-extender complex. The extender is subsequently cleaved to form a modified target-extender complex revealing the second functionality and releasing the binding determinant from the site of interest. Tethering is then performed using the second functionality to probe the site of interest. The modified target-extender complex is contacted with one or more candidate ligands. If the candidate ligand possesses an affinity for the site of interest, a second covalent bond is formed between the modified target-extender complex and the candidate ligand thereby forming a target-extender-ligand conjugate. Ligands with binding affinity for the site of interest are identified by analyzing the resulting target-extender-ligand conjugates.

In general, residues to be mutated to provide a reactive nucleophile are solvent-accessible. Solvent accessibility may be calculated from structural models using standard numeric (Lee, B. & Richards, F. M. *J. Mol. Biol* 55:379–400 (1971); Shrake, A. & Rupley, J. A. *J. Mol. Biol.* 79:351–371 (1973)) or analytical (Connolly, M. L. *Science* 221:709–713 (1983); Richmond, T. J. *J. Mol. Biol.* 178:63–89 (1984)) methods. For example, a potential cysteine variant is considered solvent-accessible if the combined surface area of the carbon-beta ($C_\beta$), or sulfur-gamma ($S_\gamma$) is greater than about 20 Å$^2$ when calculated by the method of Lee and Richards (Lee, B. & Richards, F. M. *J. Mol. Biol* 55:379–400 (1971)). This value represents approximately 33% of the theoretical surface area accessible to a cysteine side-chain as described by Creamer et al. (Creamer, T. P. et al. *Biochemistry* 34:16245–16250 (1995)).

It is also preferred that the residue to be mutated to provide a reactive nucleophile not participate in hydrogen-bonding with backbone atoms or, that at most, it interacts with the backbone through only one hydrogen bond. Wildtype residues where the side-chain participates in multiple (>1) hydrogen bonds with other side-chains are also less preferred. Variants for which all standard rotamers ($\chi_1$ angle of −60°, 60°, or 180°) can introduce unfavorable steric contacts with the N, $C_\alpha$, C, O, or $C_\beta$ atoms of any other residue are also less preferred. Unfavorable contacts are defined as interatomic distances that are less than 80% of the sum of the van der Waals radii of the participating atoms.

Other preferred variants are those which, when mutated to a desired nucleophilic residue would possess a conformation that provides a vector towards the site of interest. For example, if mutating a residue to a cysteine, than the cysteine when tethered as to comprise -Cys-SSR, should possess an allowable conformation that directs the atoms of R towards the site of interest. Two general procedures can be used to identify these preferred variants. In the first procedure, a search is made of unique structures (Hobohm, U. et al. *Protein Science* 1:409–417 (1992)) in the Protein Databank (Berman, H. M. et al. *Nucleic Acids Research* 28:235–242 (2000)) to identify structural fragments containing a disulfide-bonded cysteine at position j in which the backbone atoms of residues j−1 ,j, and j+1 of the fragment can be superimposed on the backbone atoms of residues i-1, i, and i+1 of the target molecule with an RMSD of less than 0.75 squared Angstroms. If fragments are identified that place the $C_\beta$ atom of the residue disulfide-bonded to the cysteine at position j closer to any atom of the site of interest than the $C_\beta$ atom of residue i (when mutated to cysteine), position i is considered preferred. In an alternative procedure, the residue at position i is computationally "mutated" to a cysteine, capped with an S-Methyl group via a disulfide bond (such that the side chain is —$CH_2SSCH_3$), and is placed in the standard rotamer conformations for cysteine. A residue is considered to be a suitable candidate for cysteine mutation if it can be substituted with at least one rotamer that places the methyl carbon of the S-methyl group closer to the site of interest than the residue's $C_\beta$ atom.

In addition to adding residues that provide a reactive nucleophile, it may be desirable to delete one or more naturally occurring residues that possess reactive groups. For example, reactive cysteines can be replaced with other amino acids such as alanines for example.

Various recombinant, chemical, synthetic and/or other techniques can be employed to modify a target for use in tethering. Such techniques include, for example, site-directed mutagenesis of the nucleic acid sequence encoding the target polypeptide such that it encodes a polypeptide with a different number of cysteine residues. Site-directed mutagenesis using polymerase chain reaction (PCR) amplification is described in, for example, U.S. Pat. No. 4,683,195 issued Jul. 28, 1987 and Current Protocols In Molecular Biology, Chapter 15 (Ausubel et al., ed., 1991). Other site-directed mutagenesis techniques are also well known in the art and are described, for example, in the following publications: Ausubel et al., supra, Chapter 8; Molecular Cloning: A Laboratory Manual., 2nd edition (Sambrook et al., 1989); Zoller et al., Methods Enzymol. 100:468–500 (1983); Zoller & Smith, DNA 3:479–488 (1984); Zoller et al., Nucl. Acids Res., 10:6487 (1987); Brake et al., Proc. Natl. Acad. Sci. USA 81:4642–4646 (1984); Botstein et al., Science 229:1193 (1985); Kunkel et al., Methods Enzymol. 154:367–82 (1987), Adelman et al., DNA 2:183 (1983); and Carter et al., Nucl. Acids Res., 13:4331 (1986). Cassette mutagenesis (Wells et al., Gene, 34:315 [1985]), and restriction selection mutagenesis (Wells et al., Philos. Trans. R. Soc. London SerA, 317:415 [1986]) may also be used.

Amino acid sequence variants with more than one amino acid substitution may be generated in one of several ways. If the amino acids are located close together in the polypeptide chain, they may be mutated simultaneously, using one oligonucleotide that codes for all of the desired amino acid substitutions. If, however, the amino acids are located some distance from one another (e.g. separated by more than ten amino acids), it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. The alternative method involves two or more rounds of mutagenesis to produce the desired mutant.

Synthetic methods for forming a reversible or irreversible covalent bond between reactive groups on a target and an extender, a target-extender complex and a ligand, or between two ligands, are well known in the art, and are described in basic textbooks, such as, e.g. March, *Advanced Organic Chemistry*, John Wiley & Sons, New York, $4^{th}$ edition, 1992. Reductive aminations between aldehydes and ketones and amines are described, for example, in March et al., supra, at pp. 898–900; alternative methods for preparing amines at page 1276; reactions between aldehydes and ketones and hydrazide derivatives to give hydrazones and hydrazone derivatives such as semicarbazones at pp. 904–906; amide bond formation at p. 1275; formation of ureas at p. 1299; formation of thiocarbamates at p. 892; formation of carbamates at p. 1280; formation of sulfonamides at p. 1296; formation of thioethers at p. 1297; formation of disulfides at p. 1284; formation of ethers at p. 1285; formation of esters at p. 1281; additions to epoxides at p. 368; additions to aziridines at p. 368; formation of acetals and ketals at p. 1269; formation of carbonates at p. 392; formation of denamines at p. 1264; metathesis of alkenes at pp. 1146–1148 (see also Grubbs et al., *Acc. Chem. Res.* 28:446–453 [1995]); transition metal-catalyzed couplings of aryl halides and sulfonates with alkanes and acetylenes, e.g. Heck reactions, at p.p. 717–178; the reaction of aryl halides and sulfonates with organometallic reagents, such as organoboron, reagents, at p. 662 (see also Miyaura et al., *Chem. Rev.* 95:2457 [1995]); organotin, and organozinc reagents, formation of oxazolidines (Ede et al., *Tetrahedron Letts.* 28:7119–7122 [1997]); formation of thiazolidines (Patek et al., *Tetrahedron Letts.* 36:2227–2230 [1995]); amines linked through amidine groups by coupling amines through imidoesters (Davies et al., *Canadian J. Biochem.* c50:416–422 [1972]), and the like.

PTPs

For the purposes of illustration, the above-described methods are applied to an important class of targets, protein tyrosin phosphatases ("PTPs"). These methods are described within the context of the more general extended tethering methods that are specifically tailored for use with PTPs.

Tyrosine phosphorylation is reversible and dynamic, and the equilibrium between phosphorylated and unphosphorylated protein is governed by the opposing activities of protein tyrosine kinases ("PTKs") that catalyze the addition of a phosphate group and protein tyrosine phosphatases ("PTPs") that catalyze the reverse activity or the removal of the added phosphate group. Recent studies indicate that tyrosine phosphorylation is essential in controlling normal cell-to-cell communication, cell cycle, cell growth and proliferation, cell migration, differentiation, gene transcription, immune response, ion channels, metabolism, and survival. As a result, PTPs have become targets for drug discovery efforts as defects in the pathway or an imbalance in the levels of phosphorylated and unphosphorylated tyrosines in proteins contributes to many human diseases such as cancer, diabetes, rheumatoid arthritis and hypertension.

The hallmark of a PTP is the presence of the PTP signature motif: $(H/V)C(X)_5R(S/T)$ where X is any amino acid residue. See Zhang, Current Opinions in Chemical Biology 5: 416–423 (2001); and Zhang, Annual Review of Pharmacology and Toxicology 42: 209–234 (2002). The PTP signature motif is found in a critical loop (termed the PTP loop or P-loop) in the active site of the catalytic PTP domain and includes two (cysteine and arginine) of the three essential catalytic residues. The third catalytic residue is aspartic acid and is found in the WPD loop (also known as the flexible loop). In addition, all PTPs are characterized by their ability to hydrolyze p-nitrophenyl phosphate without the presence of a metal ion, sensitivity to vanadate, and insensitivity to okadaic acid.

PTP's can be categorized into three subfamilies: 1) tyrosine-specific; 2) dual-specific; and 3) low molecular weight phosphatases. Tyrosine-specific PTPs can be further divided into two groups: a) receptor-type PTPs and b) non-receptor type PTPs. Receptor-type PTPs generally have an extracellular putative ligand-binding domain, a single transmembrane region, and one or two cytoplasmic PTP domains. The catalytic domain is termed the PTP domain. Table 1 includes illustrative examples of receptor-type PTPs, indications, and references in which the specific receptor PTP is described in greater detail.

TABLE 1

| PHOSPHATASE | INDICATION | REFERENCES |
| --- | --- | --- |
| PTP α (AKA leukocyte common antigen related polypeptide PTP; TP alpha; PTPLCA-related phosphatase) | Diabetes Cancer | Oncogene 19 (43), 4979–4987 (2000) J. Biol. Chem. 273 (48), 31890–31900 (1998) Nature 359 (6393), 336–339 (1992) |
| PTP R type C (AKA leukocyte common antigen; CD45) | immune system disorders | Nature 409 (6818), 349–354 (2001) Nature 390 (6660), 629–632 (1997) |
| PTP δ | nervous system disorders where nerve regeneration is indicated | PNAS 92 (25), 11686–11690 (1995) |
| PTP ε | Cancer | J. Biol. Chem. 275 (36), 28216–28221 (2000) EMBO J. 19 (15), 4036–4045 (2000) Oncogene 18 (36), 5024–5031 (1999) |
| LAR, (AKA PTP R type F, Leukocyte antigen related TP; LCA-homolog) | Diabetes Obesity | PNAS 98 (9), 5187–5192 (2001) J. Biol. Chem. 274 (15), 10173–10183 (1999) |
| PTP γ | Cancer | Genomics 32 (2), 225–235 (1996) PNAS 88 (11), 5036–5040 (1991) |
| PTP κ | keratinocyte-mediated skin. | Gene 186 (1), 77–82 (1997) Biochem. Biophys. Res. Commun. 228 (3), 807–812 (1996) J. Biol. Chem. 270 (24), 14247–14250 (1995) |
| PTP μ | cellular adhesion disorders | J. Biol. Chem. 276 (18), 14896–14901 (2001) Cell Biol. 122 (4), 961–972 (1993) |
| PTP R type Q (AKA PTP NCPTPCOM1; PTPCr1PTPase; Ch-1 PTPase) | nervous system disorders where nerve regeneration is indicated | Gene 162 (2), 279–284 (1995) J. Biol. Chem. 270 (1), 49–53 (1995) |
| PTP-J (AKA PTPomiron; PTPRO; PTPpi; pancreatic carcinoma phosphatase-2; PCP-2) | Cancer and nervous system disorders where nerve regeneration is indicated | Biochem. Biophys. Acta 1450 (3), 331–340 (1999), Oncogene 12 (12), 2555–2562 (1996) |

Non-receptor type PTPs contain a single catalytic domain and various amino- or carboxy-terminal extensions. These extensions include SH2 domains, PDZ domains, and extra cellular ligand binding domains. Table 2 includes illustrative examples of non-receptor type PTPs, indications, and references in which the specific PTP is described in greater detail.

TABLE 2

| PHOSPHATASE | INDICATOR | REFERENCES |
| --- | --- | --- |
| PTP-1B | Diabetes Obesity | J. Biol. Chem. 276 (51), 47771–47774 (2001) J. Biol. Chem. 276 (13), 10207–10211 (2001) Science 263 (5152), 1397–1404 (1994) |

TABLE 2-continued

| PHOSPHATASE | INDICATOR | REFERENCES |
|---|---|---|
| TC-PTP (AKA T-cell-PTP) | Leukemia | J. Biol. Chem. 274 (39), 27768–27775 (1999) Genomics 16 (3), 619–629 (1993) |
| PTP-H1 (AKA cytoskeletal-associated PTP) | Cancer | J. Biol. Chem. 274 (25), 17806–17812 (1999) J. Biol. Chem. 272 (43), 27281–27287 (1997) J. Gastroenterol 29 (6), 727–732 (1994) |
| PTP-MEG1 (AKA megakaryocyte PTP) | glutamine receptor signaling disorders | J. Biol. Chem. 275 (21), 16167–16173 (2000) Proc. Natl. Acad. Sci. U.S.A. 88 (13), 5867–5871 (1991) |
| SHP-1 (AKA SH-PTP1; PTP-1c) | hematopoiesis disorders | EMBO J. 14 (11), 2519–2526 (1995) Molecular and cellular biology, 12 (2), 836–846 (1992) |
| LC-PTP (AKA HEPTP; HePTPase; hematopoeitic PTP; PTP NR type stress induced) | immune system disorders | J. Immunol. 163 (3), 1282–1288 (1999) J. Biol. Chem. 274 (17), 11693–11700 (1999) |
| PTPMEG2 (AKA PTPaseMEG2) | phagocytosis disorders | J. Biol. Chem. 277 (4), 2620–2628 (2002) Proc. Natl. Acad. Sci. U.S.A. 89 (7), 2980–2984 (1992) |
| SHP-2 (AKA PTP-ID; PTP-2c; SH-PTP3; SH-PTP2) | cellular proliferation disorders | J. Biol. Chem. 275 (7), 5208–5213 (2000) J. Biol. Chem. 275 (1), 599–604 (2000) Proc. Natl. Acad. Sci. U.S.A. 96 (17), 9677–9682 (1999) Mol. Cell. Biol. 19 (4), 3125–3135 (1999) Proc. Natl. Acad. Sci. U.S.A. 90 (6), 2197–2201 (1993) |
| PTP-G1 (AKA PTP-PEST) | Cancer | J. Biol. Chem. 276 (26), 24422–24431 (2001) Mol. Cell 6 (6); 1413–1423 (2000) J. Biol. Chem. 274 (6), 3811–3818 (1999) FEBS Lett. 339 (3), 222–228 (1994) |
| PTP-1E (AKA PTPL1; Fas-associated phosphatase-1, FAP-1; PTP-BAS; Apo1/CD95(Fas)-associated phosphatase | apoptotic disorders | Eur. J. Biochem. 267 (24), 7170–7175 (2000) J. Biol. Chem. 272 (39), 24333–24338 (1997) |

The other two subfamilies of PTPs, dual-specific PTPs and low molecular weight phosphatases, are not as well characterized in the literature as the tyrosine-specific PTPs. As its name implies, dual-specific PTPs can remove phosphates from both phosphotyrosine-containing proteins and phosphoserine or phosphothreonine-containing proteins. Illustrative examples of dual-specific PTPs include Cdc25A, PTEN, and MAP kinase phosphatases. Finally, low molecular weight phosphatases are so termed because they generally include only the PTP domain.

Although the methods that follow are described with reference to a particular PTP, PTP-1B, they are generally applicable to all PTPs due to the fact that the three-dimensional structures of the PTP domain (formed by approximately 240 residues) of all three subfamilies of PTPs are remarkably similar. The structural similarity of the PTP domain is striking in view of the variation in amino acid sequences and the differences in substrate specificity between the tyrosine-specific PTPs and the dual-specificity PTPs. A particularly useful publication providing a structural alignment of the PTP domains of the known PTPs to date is Andersen et al., *Mol Cell Biol* 21:7117–7136 (2001) which is incorporated herein by reference.

Briefly, all of the PTP domains are composed of a highly twisted mixed β-sheet flanked by α-helices on both sides. Not surprisingly, the active site of the PTP domain is the most conserved among PTPs and prominently features a pTyr binding pocket. Because the PTP domain includes the active site, it is sometimes referred to as the catalytic domain. The diversity of PTPs in function and overall structure is a consequence of the presence of diverse non-catalytic regulatory and targeting domains that are found in the N and C termini that often flank the PTP domain.

In one aspect of the present invention, a general method for using extenders is provided for identifying ligands that bind to the active site of PTP. In one embodiment, the method uses the active site cysteine (e.g, C215 in PTP-1B) as the reactive thiol and comprises:

a) providing a PTP having active site thiol;
b) contacting the PTP with an extender thereby forming a PTP-extender complex wherein the extender comprises a first functionality that forms a covalent bond with the active site thiol and a second functionality that is capable of forming a disulfide bond;
c) contacting the PTP-extender complex with a candidate ligand that comprises a group that is capable of forming a disulfide bond with the second functionality;
d) forming a disulfide bond between the PTP-extender complex and the candidate ligand thereby forming a PTP-extender-ligand conjugate; and,
e) identifying the candidate ligand present in the PTP-extender-ligand conjugate.

In one embodiment, the PTP is contacted with a candidate ligand in the presence of a reducing agent. Illustrative examples of suitable reducing agents include but are not limited to: cysteine, cysteamine, dithiothreitol, dithioerythritol, glutathione, 2-mercaptoethanol, 3-mercaptoproprionic acid, a phosphine such as tris-(2-carboxyethylphosphine) ("TCEP"), or sodium borohydride. In one embodiment, the reducing agent is 2-mercaptoethanol. In another embodiment, the reducing agent is cysteamine. In another embodiment, the reducing agent is glutathione. In another embodiment, the reducing agent is cysteine.

In another embodiment, the candidate ligand possesses a —SH group. In another embodiment, the candidate ligand possesses a masked thiol. In another embodiment, the candidate ligand possesses a masked thiol in the form of a disulfide of the formula —SSR$^1$ where R$^1$ is unsubstituted $C_1$–$C_{10}$ aliphatic, substituted $C_1$–$C_{10}$ aliphatic, unsubstituted aromatic or substituted aromatic. In another embodiment, the candidate ligand possesses a thiol masked as a disulfide of the formula —SSR$^2$R$^3$ wherein R$^2$ is $C_1$–$C_5$ alkyl (preferably —CH$_2$—, —CH$_2$CH$_2$—, or —CH$_2$CH$_2$CH$_2$—) and R$^3$ is NH$_2$, OH, or COOH. In another embodiment, the candidate ligand possesses a thiol masked as a disulfide of the formula —SSCH$_2$CH$_2$OH. In yet another embodiment, the candidate ligand possesses a thiol masked as a disulfide of the formula —SSCH$_2$CH$_2$NH$_2$. Illustrative examples of candidate ligands include:

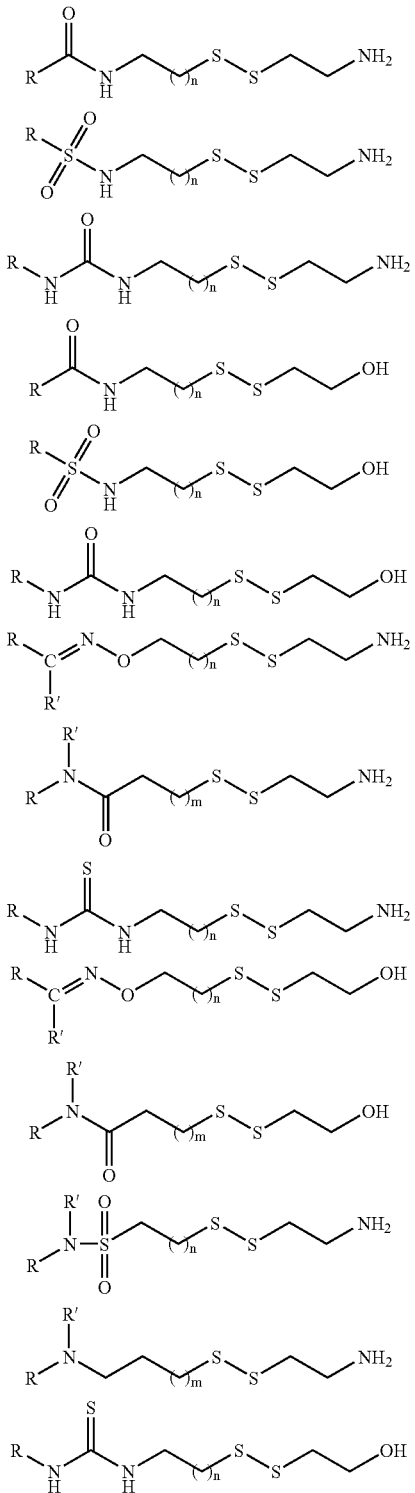

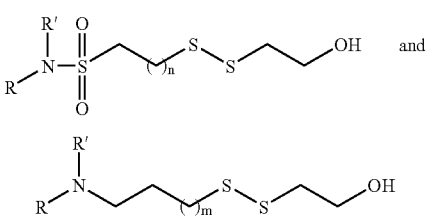

In another embodiment, the extender comprises a first and second functionalities as described above and includes a binding determinant that possesses an inherent binding affinity for the active site. If the binding determinant does not already include a first and second functionality, then it can be modified to contain them. In one method, tethering is used to identify a binding determinant RC that is then modified to include a first and second functionalities. In another method, the binding determinant is obtained from known substrates of the target or fragments thereof.

In another embodiment, the extender comprises a first and second functionalities as described above and includes a phosphotyrosine or a phosphotyrosine mimetic as the binding determinant. Phosphotyrosine mimetics are described for example in Burke et al., *Biopolymers*, 60: 32–44 (2001) which is incorporated herein by reference. In another embodiment, the phosphotyrosine or phosphotyrosine mimetic is selected from the group consisting of:

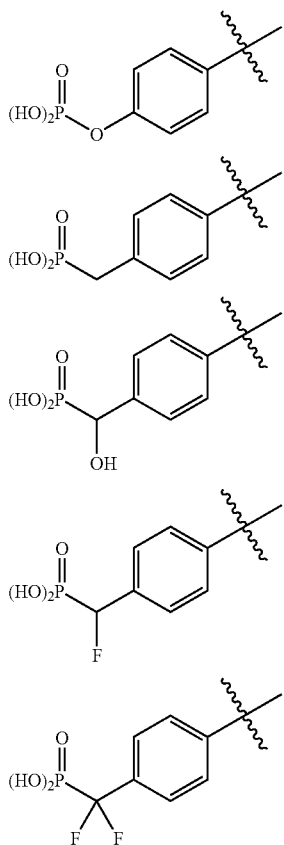

-continued
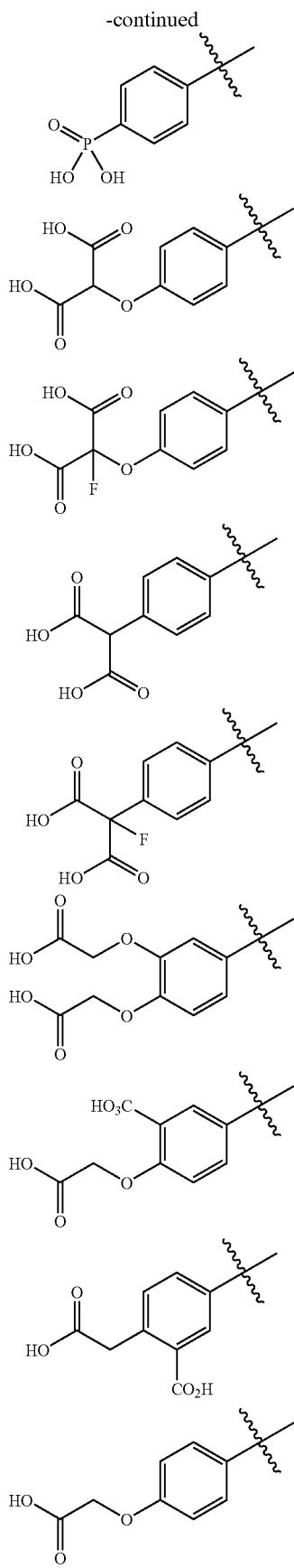
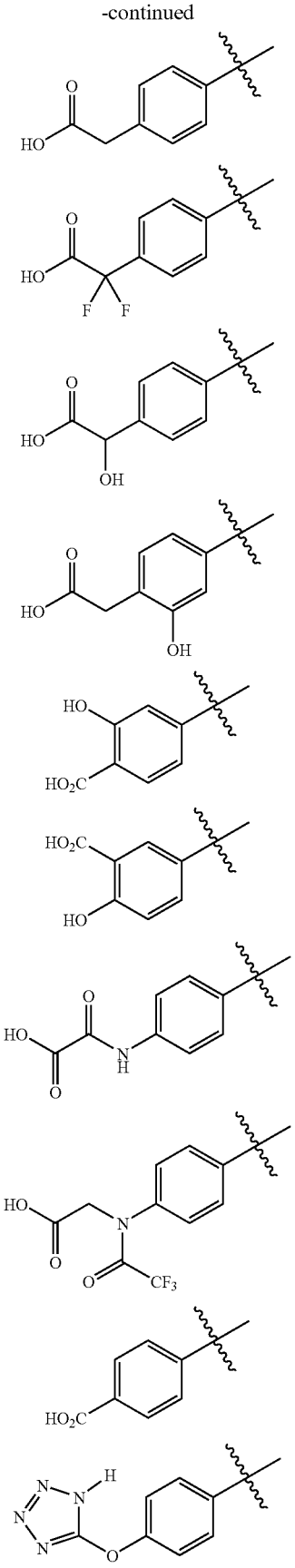

-continued

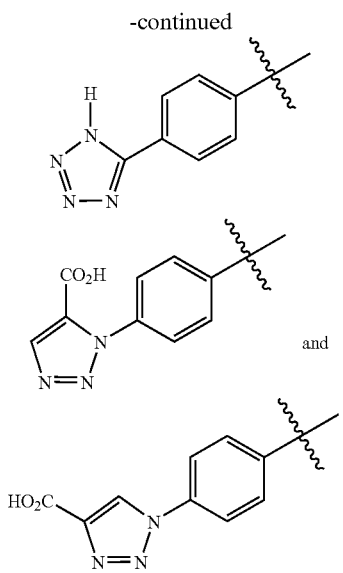

In another embodiment, the phosphotyrosine or phosphotyrosine mimetic is selected from the group consisting of:

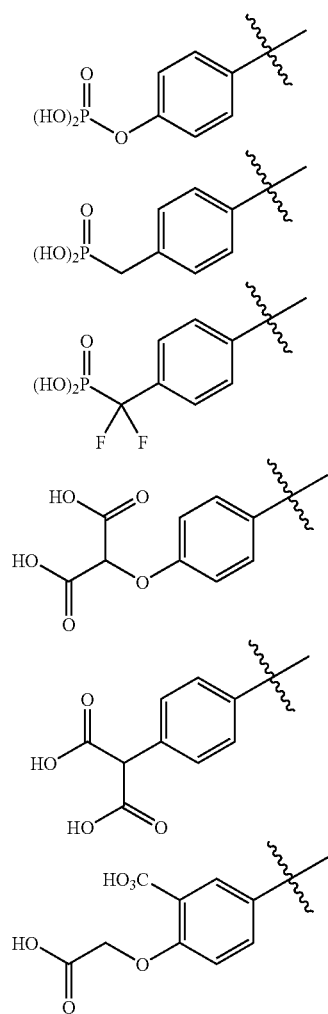

-continued

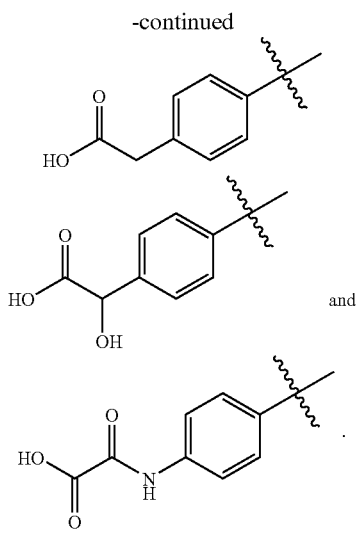

In another embodiment, the first and second functionalities of the extender are each independently a —SH or a masked —SH. An illustrative example of a masked thiol is a thioester of the formula —SC(=O)R$^1$ or a disulfide of the formula —SSR$^1$ where R$^1$ is as previously described. In this embodiment, the covalent bond formed between the target and the extender is a disulfide bond and thus is a reversible covalent bond. In one variation of the method, the target is contacted with the extender prior to contacting the target-extender complex with one or more candidate ligands. In another variation, the target is contacted with a pool comprising the extender and one or more candidate ligands.

In another embodiment, the extender comprises an alkylating agent that additionally comprises a masked thiol that is capable of forming a covalent bond with a candidate ligand. In one method, the alkylating agent is a halomethyl-ketone or a halomethyl-acetamide. Illustrative examples of chloromethyl-ketones include but are not limited to:

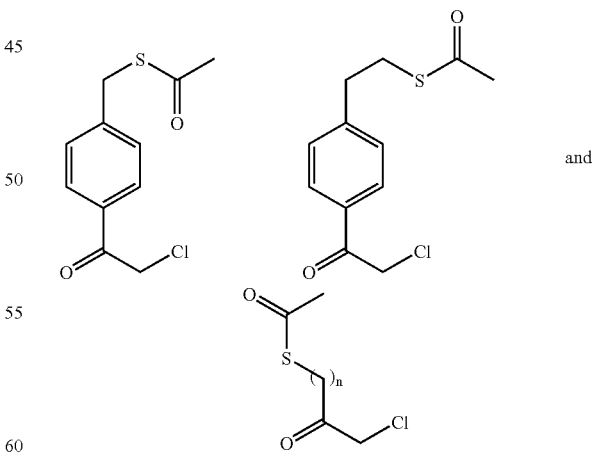

wherein n is 1–5, more preferably 1–3. In another method, the alkylating agent is a chloromethyl-ketone. In another method, the alkylating agent is a chloromethyl-acetamide. Illustrative examples of chloro-methyl acetamide extenders include but are not limited to:

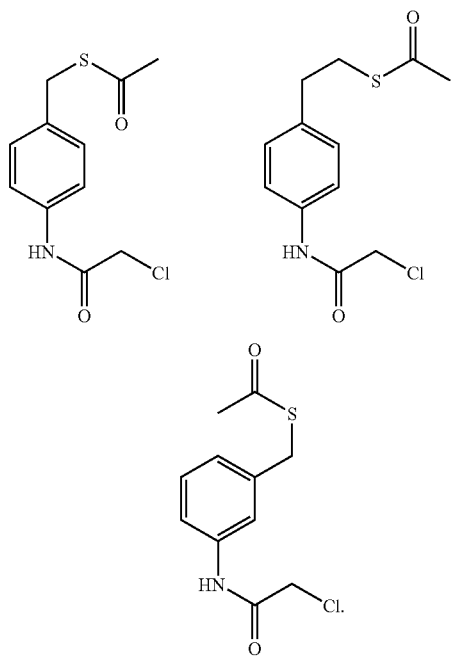

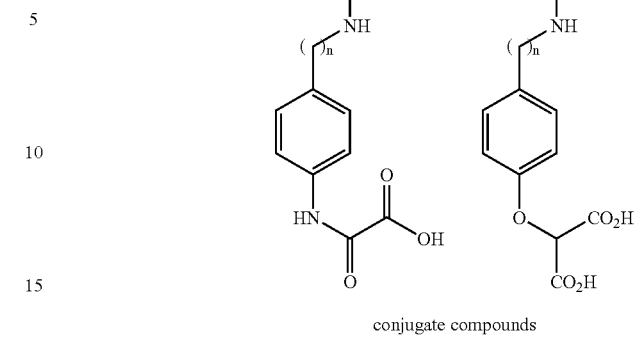

conjugate compounds

These chloromethyl ketones and chloromethyl acetamides are examples of extenders that comprise a first and second functionalities. Methods for making these extenders are described in Examples 1–8.

Scheme 1 illustrates one method for using such extenders to derive ligands that bind PTPs.

As shown, the extender is used to modify the active site thiol and the masked second functionality, a masked thiol, is deprotected. The PTP-extender complex then is used in a tethering experiment and is contacted with a library of candidate ligands. One embodiment of a tethering method using an extender with PTP-1B is further described in Example 9. Tethering identifies a binding determinant R that is specific for a site adjacent to the phosphotyrosine binding site (in which the active site thiol resides). As a result, conjugate compounds that are active site inhibitors of PTPs can be made combining a phosphotyrosine or phosphotyrosine mimetic with the identified binding determinant R. Because disulfide bonds are generally not stable, these linkages are typically replaced when making conjugate compounds.

Scheme 2 illustrates a variation of this method for making conjugate compounds using extenders where first functionality is located off a phenyl ring to aid in the superimposition of the phosphotyrosine or phosphotyrosine mimetic.

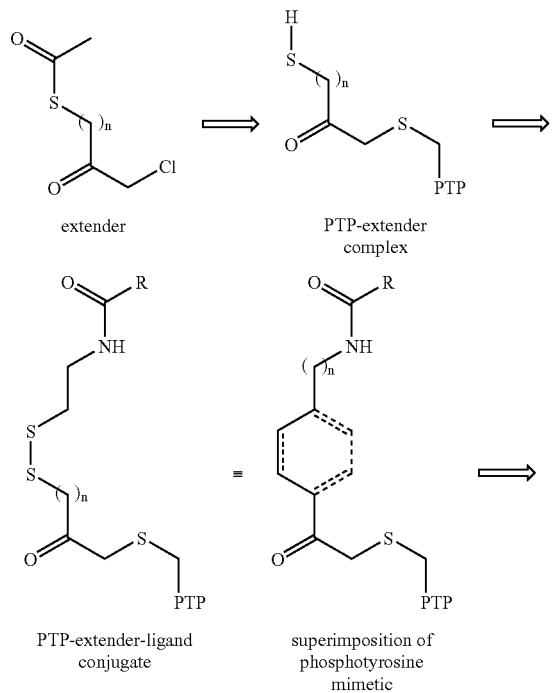

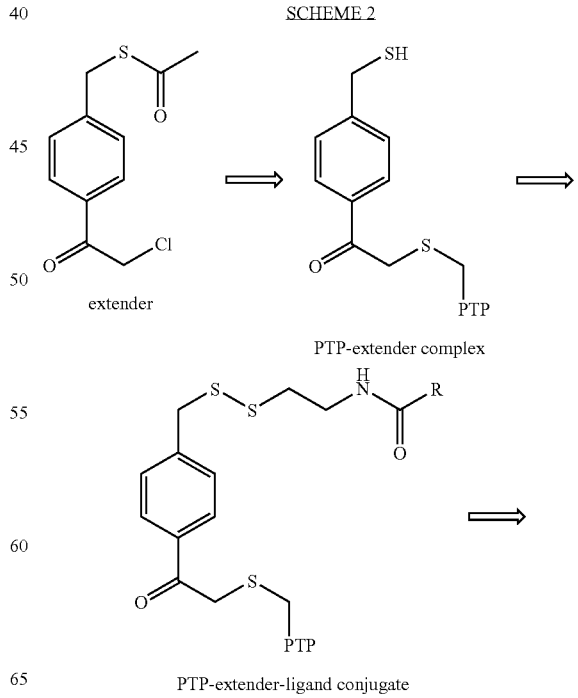

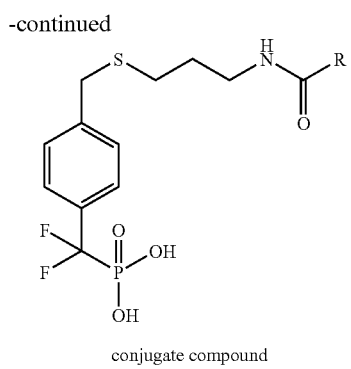

conjugate compound

The synthesis of one such conjugate compound is further described in Example 10.

In another aspect of the present invention, the extender strategy is used without forming a covalent bond in the active site to minimize potential structural rearrangements therein. Like the above described methods, the extender comprises a first functionality that is capable of forming a covalent bond with the reactive thiol, and a second functionality that is capable of forming a disulfide.

This method primarily differs from that described above in the location of the reactive thiol on the PTP. Instead of using the active site thiol, a reactive thiol that is located outside of the active site is used. Optionally, the extender additionally comprises a phosphotyrosine or a phosphotyrosine mimetic.

Thus, the method comprises:
a) providing a PTP having a reactive thiol located outside of the active site;
b) contacting the PTP with an extender thereby forming a PTP-extender complex wherein the extender comprises a first functionality that forms a covalent bond with the reactive thiol and a second functionality that is capable of forming a disulfide bond;
c) contacting the PTP-extender complex with a candidate ligand that comprises a group that is capable of forming a disulfide bond with the second functionality;
d) forming a disulfide bond between the PTP-extender complex and the candidate ligand thereby forming a PTP-extender-ligand conjugate; and,
e) identifying the candidate ligand present in the PTP-extender-ligand conjugate.

In embodiments where the extender includes a phosphotyrosine or a phosphotyrosine mimetic, a covalent bond is formed between the reactive thiol (that is located outside of the active site) and the first functionality thereby forming a PTP-extender complex. A covalent bond is not formed between the active site cysteine (e.g. C215 in PTP-1B) because the phosphotyrosine or phosphotyrosine mimetic binds to the active site, thus preventing the formation of a covalent bond between the active site thiol and the first functionality. Consequently, tethering experiments using the second functionality identify ligands that bind to a site adjacent to the phosphotyrosine-binding site in the PTP.

In one embodiment, the PTP is a PTP mutant comprising a cysteine instead of the naturally occurring amino acid at the position that corresponds to R47 in human PTP-1B. FIG. 3 shows the first 298 residues of human PTP-1B aligned with human TC-PTP and LAR. As it can be seen, the corresponding residue in human TC-PTP is also an arginine and is an alanine in human LAR. The corresponding residue in other PTPs can be identified using the structural alignment disclosed in Andersen et al., *Mol Cell Biol* 21:7117–7136 (2001).

If the target includes one or more naturally occurring cysteines outside of the active site, these cysteines can be mutated to another residue such as alanine, serine, or valine to eliminate the possibility of dual labeling. For example, PTP-1B contains two such cysteine, C32 and C92, that were sufficiently reactive in tethering experiments that they were mutated to another amino acid to prevent unwanted labeling. In preferred embodiments, C32 was mutated to serine and C92 was mutated to alanine. The cloning of human PTP-1B and the cysteine mutants thereof are described further in Examples 11 and 12 respectively.

In another embodiment, the extenders are of the formula:

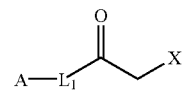

where A is a moiety comprising phosphotyrosine or a phosphotyrosine mimetic, $L_1$ is a linker, and X is a halide or together with the adjacent carbon is a carbon-carbon double bond or a carbon-carbon triple bond. The first functionality is X and the second functionality is generally located on $L_1$, although it can also be located on A. In another embodiment, A is selected from the group consisting of:

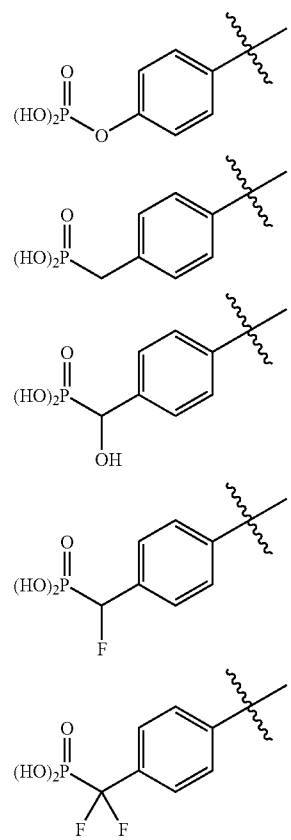

-continued
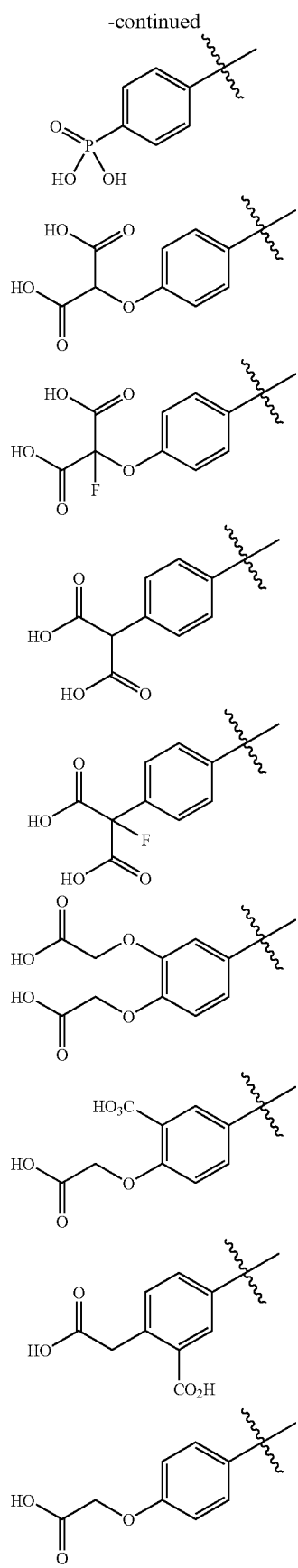
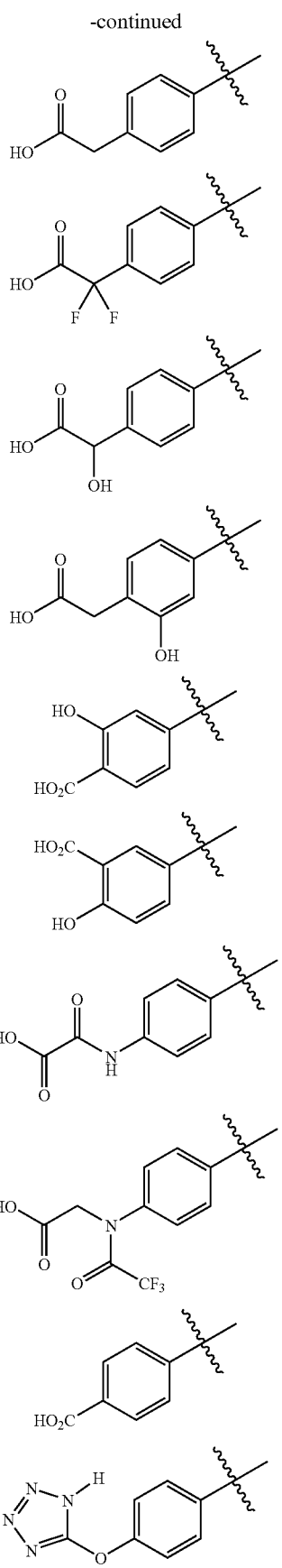

-continued

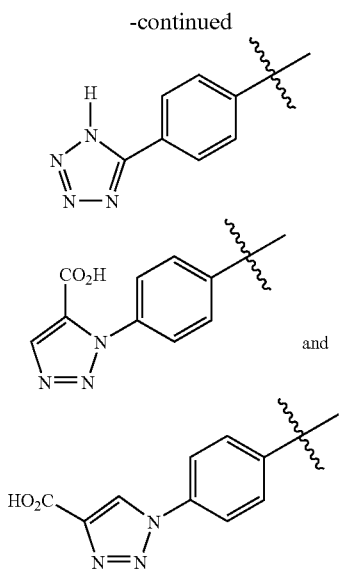

In another embodiment, A is selected from the group consisting of:

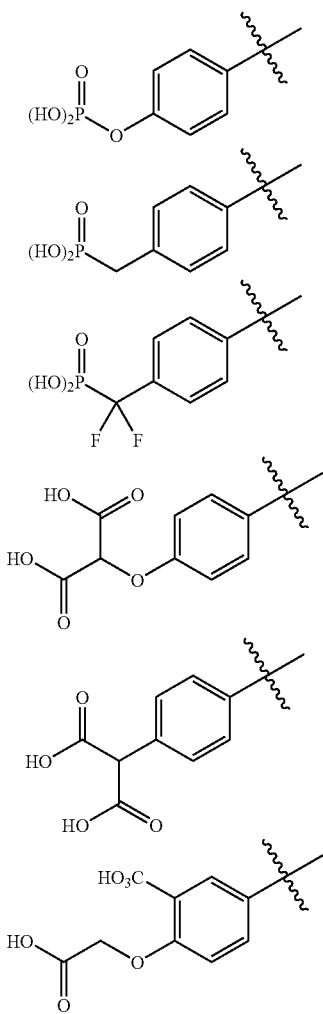

-continued

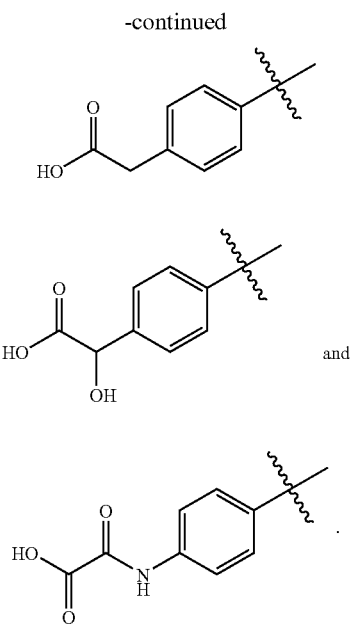

Illustrative examples of such extenders include:

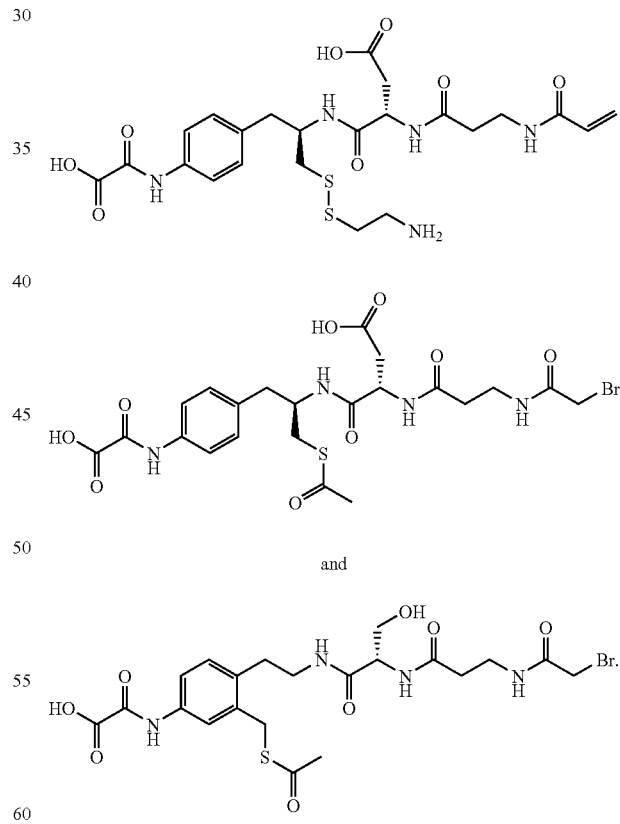

Exemplary methods for making these types of extenders are described in Examples 13–20.

Similar methods as those outlined by Schemes 1 and 2 can be used to make conjugate compounds using these extenders. Scheme 3 illustrates one embodiment for such a method.

SCHEME 3

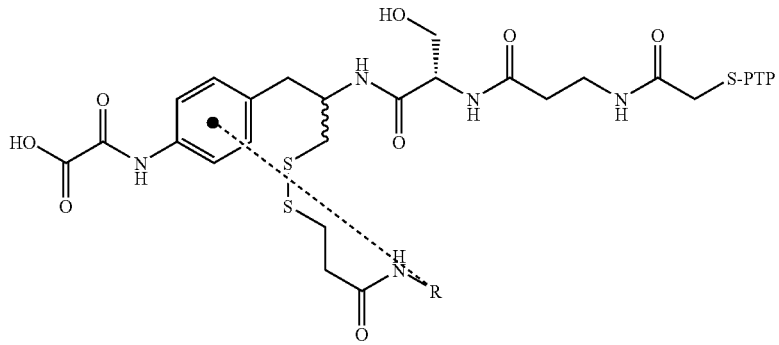

As can be seen, the phosphotyrosine or phosphotyrosine mimetic is linked with the binding determinant, R, that is identified from tethering. The portion of the extender that binds outside of the active site is eliminated from the conjugate compound. Illustrative examples of conjugate compounds that were derived using such a strategy are further described in Examples 21–25.

In another aspect of the present invention, a method of identifying a novel phosphotyrosine mimetic is provided. The method uses a PTP having an active site cysteine and a reactive thiol that is located outside of the active site, and an extender comprising a first functionality that is capable of forming a covalent bond with the reactive thiol, a cleavable linker having a latent second functionality, and a moiety comprising a phosphotyrosine or a phosphotyrosine mimetic. When the PTP is contacted with the extender, a covalent bond is formed between the reactive thiol and the first functionality thereby forming a PTP-extender complex. A covalent bond is not formed between the active site cysteine (e.g. C215 in PTP-1B) because the phosphotyrosine or phosphotyrosine mimetic binds to the active site and acts as a temporary plug, thus preventing the formation of a covalent bond between the active site thiol and the first functionality. The cleavable linker is then cleaved exposing the second functionality and thereby releasing the phosphotyrosine or phosphotyrosine mimetic, and the second functionality is used in tethering experiments to identify novel ligands that bind to the phosphotyrosine-binding site in the PTP.

Thus, the method comprises:
a) providing a PTP having an active site, a cysteine located in the active site and a reactive thiol located outside of the active site;
b) contacting the PTP with an extender thereby forming a PTP-extender complex, the extender comprising a first functionality and a latent second functionality, a cleavable linker and a binding determinant comprising a phosphotyrosine or a phosphotyrosine mimetic wherein the first functionality forms a first covalent bond with the reactive thiol and the binding determinant binds to the active site;
c) cleaving the extender at the cleavable linker thereby forming a modified PTP-extender complex by exposing the second functionality and releasing the binding determinant from the active site;
d) contacting the modified PTP-extender complex with a candidate ligand that comprises a group that is capable of forming a second covalent bond with the second functionality;
e) forming a second covalent bond between the modified PTP-extender complex and the candidate ligand thereby forming a PTP-extender-ligand conjugate; and,
f) identifying the candidate ligand present in the PTP-extender-ligand conjugate.

In one embodiment, the extender comprises a compound of the formula

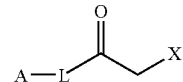

where A is a moiety comprising phosphotyrosine or a phosphotyrosine mimetic, L is a cleavable linker, and X is a halide. In another embodiment, the extender comprises a compound of the formula

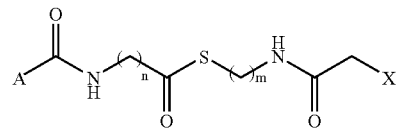

where A is selected from the group consisting of:

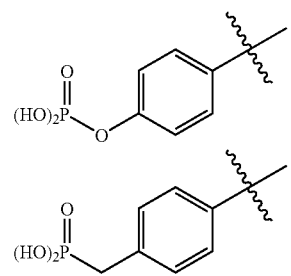

-continued
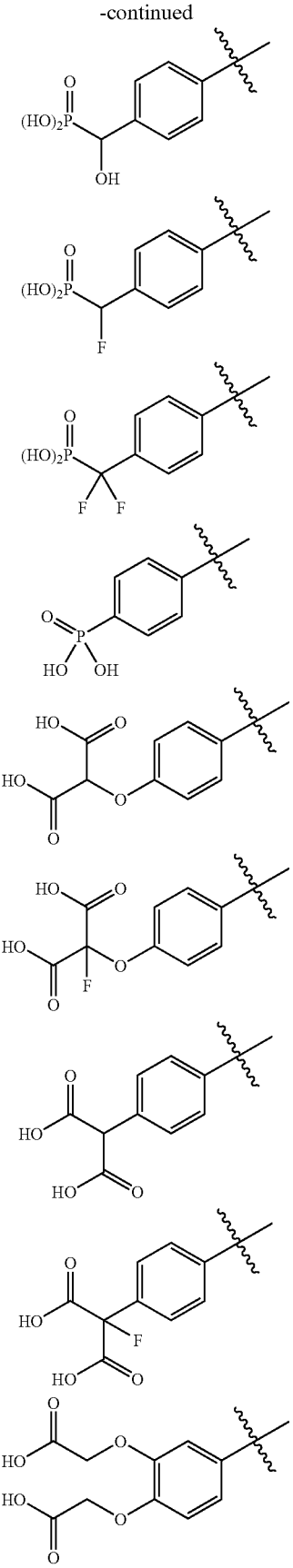
-continued
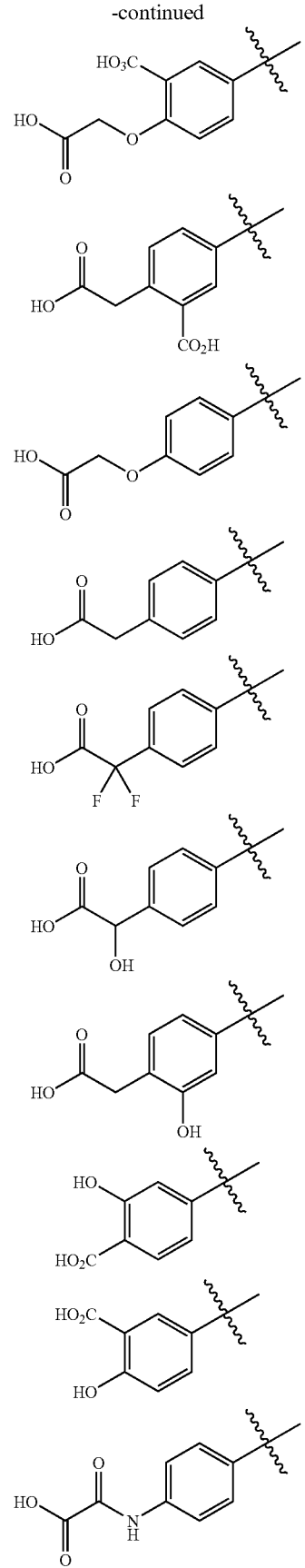

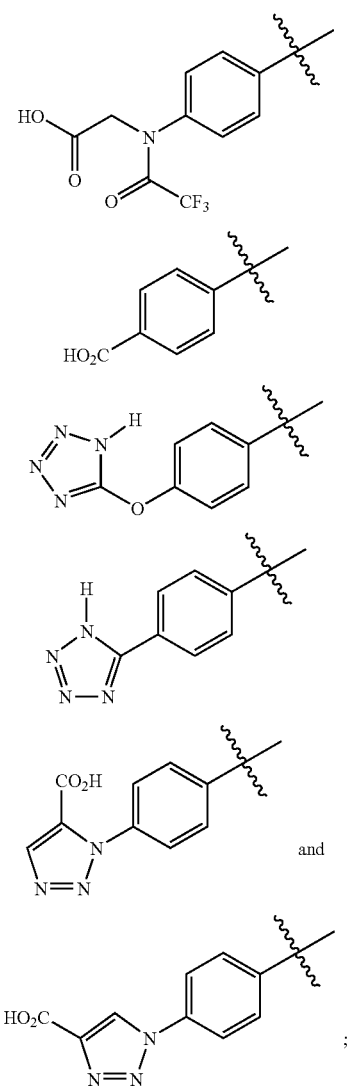
n is 1–5; m is 2–5; and, X is a halide. In another embodiment, A is selected from the group consisting of:
n and m are independently 2 or 3; and X is bromide. Examples 26 and 27 describe the synthesis of two illustrative extenders
The latter extender was used in tethering experiments to identify a novel phosphotyrosine mimetic In another aspect of the present invention, a novel phosphotyrosine mimetic is provided.

In one embodiment, the phosphotyrosine mimetic includes the moiety

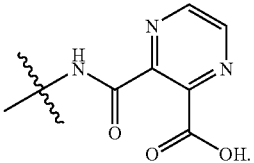

In another embodiment, the phosphotyrosine mimetic includes the moiety

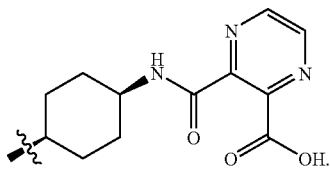

In another embodiment, the phosphotyrosine mimetic includes the moiety

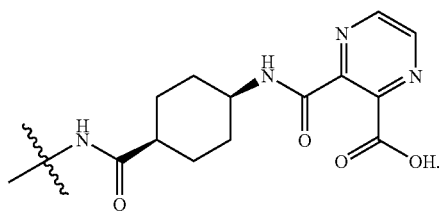

All references cited throughout the specification are expressly incorporated herein by reference. While the present invention has been described with references to specific embodiments thereof, it should be understood by those skilled in the art that various changes may be made and equivalents substituted to adapt the present invention to a particular situation. All such changes and modifications are within the scope of the present invention.

The invention is further illustrated by the following non-limiting examples.

EXAMPLE 1

This example describes the synthesis of the compound below

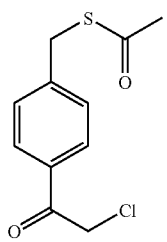

which was made according to Scheme A.

SCHEME A

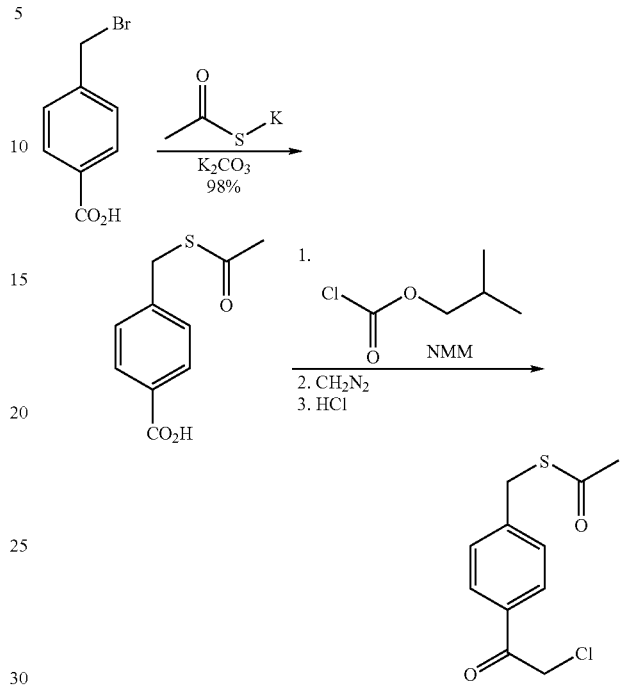

Commercially available α-bromo-p-toluic acid (0.513 g, 2.39 mmol) was reacted with potassium thioacetate (0.27 g, 2.36 mmol) and potassium carbonate (0.33 g, 2.39 mmol) in N,N-dimethylformamide (DMF, 20 ml) for 16 hours and was then flooded with 100 ml ethyl acetate (EtOAc), rinsed with 3×50 ml 1 M sodium hydrogen sulfate, 50 ml brine, dried over sodium sulfate, and evaporated to a white crust (0.484 g, 2.3 mmol, 98%, ES (+)MS m/z=211 (M+H)).

This acid was dissolved in 10 ml dry tetrahydrofuran (THF), chilled in an ice-water bath, and treated with 4-methylmorpholine (NMM, 0.26 ml, 2.37 mmol) and isobutyl-chloroformate (IBCF, 0.3 ml, 2.31 mmol). The reaction was allowed to proceed for 20 minutes before being filtered through a medium glass frit and the resultant solid rinsed with 5 ml THF. The combined pink filtrate was transferred to a round-bottom flask without ground glass joints and cooled in an ice water bath. Meanwhile, diazomethane was prepared by cooling 11 ml of diethyl ether in an ice-water bath, adding 3.2 ml of 40% potassium hydroxide, followed by 1-methyl-3-nitro-1-nitrosoguanidine (1 g, 6.8 mmol). This solution was allowed to stir for 45 minutes, and then the diazamethane ethereal layer was carefully decanted into the carbonate solution above. The reaction mixture was allowed to slowly warm to room temperature and stirred under nitrogen for two days before being chilled on ice again. A solution of 4 M HCl in dioxane (1 ml, 4 mmol) was added and the reaction allowed to proceed for 80 minutes. Residual diazomethane was then quenched with acetic acid (1 ml) and the reaction was flooded with 100 ml EtOAc, rinsed with 2×50 ml saturated sodium hydrogen carbonate, 2×50 ml 1 M sodium hydrogen sulfate, 50 ml brine, dried over sodium sulfate, and evaporated to dryness. The residue was purified by reverse-phase chromatography to yield the titled compound as a pale yellow liquid (0.07 g, 0.29 mmol, 13%, ES (+) MS m/z=243 (M+H)).

EXAMPLE 2

This example describes the synthesis of the compound below

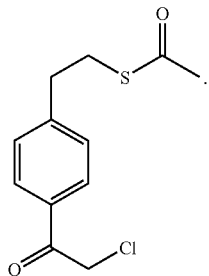

This compound was made using the method of Example 1 except that 4-(2-bromoethyl)benzoic acid was used instead of α-bromo-p-toluic acid (ES (+) MS m/z=257 (M+H)).

EXAMPLE 3

This example describes the synthesis of the compound below

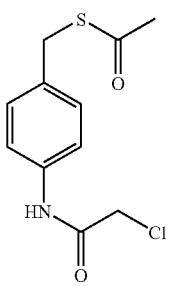

which was made according to Scheme B.

SCHEME B

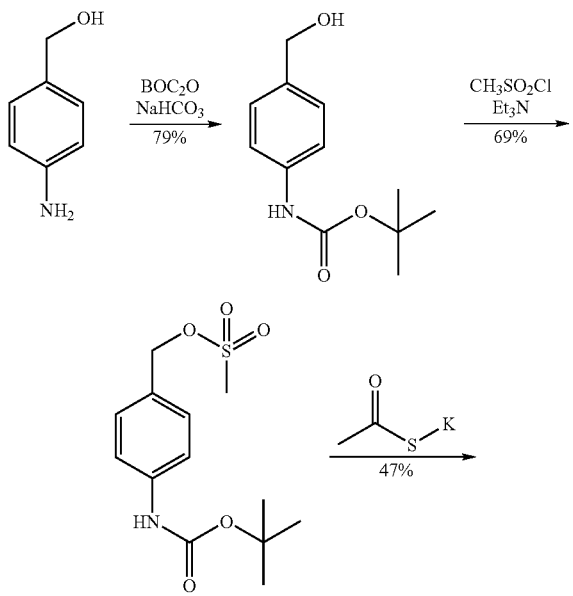

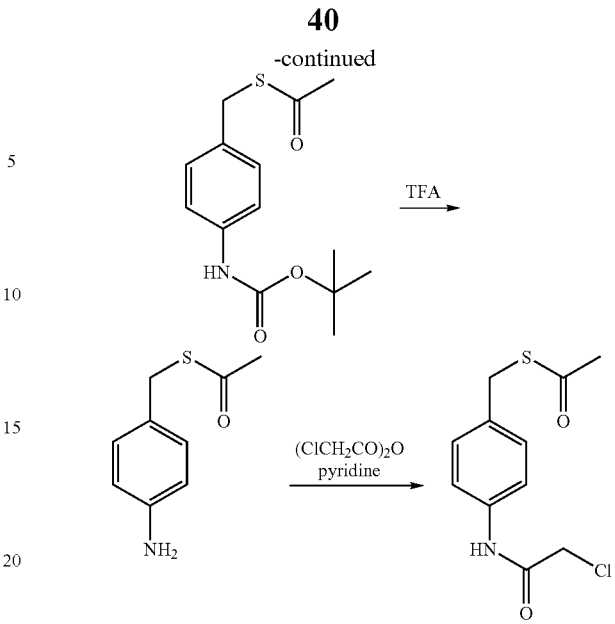

This compound was made starting with commercially available 4-amino benzyl alcohol (1.9 g, 15.4 mmol) which was reacted with di-tert-butyl-dicarbonate (3.6 g, 16.5 mmol) in 20 ml p-dioxane, 10 ml water, and 10 ml saturated sodium bicarbonate. The reaction was allowed to proceed at room temperature overnight, whereupon 20 ml water was added. The reaction mixture was extracted with 3×40 ml EtOAc, then the combined organics were rinsed with 40 ml saturated sodium bicarbonate and 2×50 ml brine, dried over sodium sulfate, filtered, and concentrated to a dark brown liquid which was purified by flash chromatography on silica gel with 70:30 hexane:EtOAc to yield a light yellow liquid (2.7 g, 12 mmol, 79%, MS m/z=246 (M+Na)).

The resulting benzyl alcohol (0.929 g, 4.16 mmol) was dissolved in 10 ml dry DCM, cooled in an ice-water bath, and treated with triethylamine (0.7 ml, 5.0 mmol) and methanesulfonyl chloride (0.35 ml, 4.52 mmol). After 3 hours the reaction was flooded with 100 ml EtOAc, rinsed with 3×50 ml 1 M sodium hydrogen sulfate, 50 ml brine, dried over sodium sulfate, and evaporated to a yellow crust (0.859 g, 2.9 mmol, 69%) This was redissolved in 2.5 ml dry DMF and then potassium thioacetate (0.35 g, 3.06 mmol) was added followed by another 2.5 ml dry DMF. The reaction was stirred vigorously for 14 hours and then flooded with 100 ml EtOAc, rinsed with 3×50 ml 1 M sodium hydrogen sulfate, 50 ml brine, dried over sodium sulfate, and evaporated to a light brown solid that was purified by flash chromatography on silica gel with 90:10 hexane:EtOAc to yield a light reddish-brown solid (0.385 g, 1.37 mmol, 47%, MS m/z=304 (M+Na)).

The resulting thioester (0.379 g, 1.35 mmol) was dissolved in 10 ml dry DCM, chilled in an ice-water bath, and treated with 10 ml trifluoroacetic acid. The reaction was allowed to proceed on ice for 30 minutes at which time solvents were removed by rotary evaporation. The residue was then redissolved in 10 ml dry pyridine and treated with chloroacetic anhydride (0.448 g, 2.62 mmol). The reaction was allowed to proceed for one hour at room temperature, then quenched with 10 ml water. The reaction was then flooded with 100 ml EtOAc, rinsed with 2×50 ml saturated sodium hydrogen sulfate, 2×50 ml 1 M sodium bicarbonate, 50 ml brine, dried over sodium sulfate, and evaporated to dryness. The residue was purified by flash chromatography on silica gel with 70:30 hexane:EtOAc to yield the titled compound as an off-white solid (0.194 g, 0.753 mmol, 56%, ES (+) MS m/z=280 (M+Na)).

EXAMPLE 4

This example describes the synthesis of the compound below

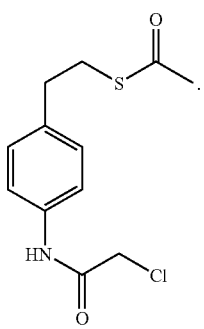

This compound was made using the method of Example 3 except that 4-aminophenethyl alcohol was used instead of 4-amino benzyl alcohol (ES (+) MS m/z=294 (M+Na)).

EXAMPLE 5

This example describes the synthesis of the compound below

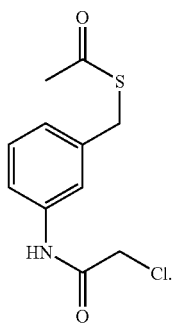

This compound was made using the method of Example 3 except that 3-aminobenzyl alcohol was used instead of 4-amino benzyl alcohol (ES (+) MS m/z=258 (M+H)).

EXAMPLE 6

This example describes the synthesis of

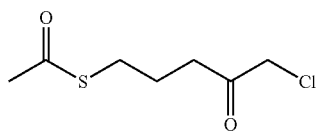

which was made according to Scheme C where n=3.

SCHEME C

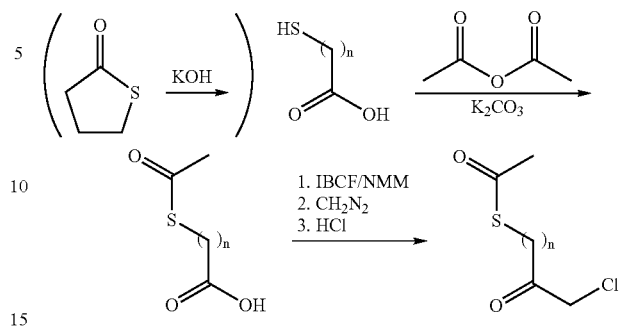

This compound was made starting with commercially available γ-thiobutyrolactone (1.01 g, 9.89 mmol) which was dissolved in water (10 ml) and THF (15 ml) and sparged with nitrogen. Solid potassium hydroxide (1.73 g, 30.8 mmol) was added and the reaction was allowed to proceed at room temperature for 2.5 hours. The reaction was then cooled in an ice-water bath and acetic anhydride (5 ml, 53 mmol) was added. The reaction was stirred on ice for 1 hour, then flooded with 100 ml 1 N HCl. The mixture was extracted with 3×30 ml EtOAc, and the combined organics were then rinsed with 50 ml 1 N HCl and 50 ml brine, dried over sodium sulfate, filtered, and solvent removed under reduced pressure. The resulting liquid was chromatographed on silica gel with 1:1 EtOAc:hexane to yield the S-acetyl acid (0.742 g, 4.6 mmol, 46%, ES (+) MS m/z=185 (M+Na)).

The resulting acid was converted to the chloromethylketone as described in Scheme A of Example 1 (where the resulting acid was used instead of α-bromo-p-toluic acid), and the final product was purified on silica gel with 90:10 hexane:EtOAc to yield the titled compound (0.314 g, 1.61 mmol, 35%, ES (+) MS m/z=217 (M+Na)).

EXAMPLE 7

This example describes the synthesis of the compound below

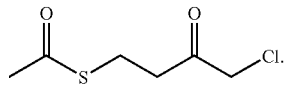

This compound was made as described in Scheme A of Example 1 using 3-mercaptopropionic acid instead of α-bromo-p-toluic acid (ES (+) MS m/z=203 (M+Na)).

EXAMPLE 8

This example describes the synthesis of the compound below

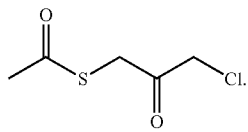

This compound was synthesized by reacting commercially available 1,3-dichloroacetone (1.177 g, 9.27 mmol) with thiolacetic acid (0.7 ml, 9.8 mmol) and triethylamine (1.4 ml, 10 mmol) in THF (20 ml) in an ice-water bath. The reaction was allowed to proceed for one hour, then flooded with 50 ml EtOAc, rinsed with 3×35 ml saturated sodium bicarbonate and 35 ml brine, dried over sodium sulfate, filtered, and solvent removed under reduced pressure to yield a yellow liquid which was purified twice using flash chromatography on silica gel, first with 80:20 hexane: EtOAc, then with 90:10 hexane:EtOAc. The purest fractions were then concentrated under reduced pressure to a pale yellow liquid consisting of the titled compound (0.187 g, 1.12 mmol, 12%, ES (+) MS m/z=167 (M+H)).

EXAMPLE 9

This example describes one embodiment of a tethering experiment using a PTP-1B-extender complex or a modified PTP-1B-extender complex (generically referred to as "the protein").

The protein concentration was adjusted to 5 μM and β-mercaptoethanol ("β-ME" was added such that its concentration was 1 mM. The protein/β-ME solution was then incubated with a monophore library pool dissolved in DMSO (50 μM each monophore final) for 1 hour and subjected to LC/MS analysis on either a Finnigan MAT LCQ or an Applied Biosystems Inc. API Qstar Pulsar I. Spectra were deconvoluted using either Xcalibur software package (Finnigan MAT) or Analyst QS software package (Applied Biosystems Inc.). Relative peak heights were used to roughly quantitate the fraction of protein conjugated with bound cysteamine and ligand-candidate hits. Individual ligand candidates that generated hits were identified by mass and incubated individually for 1 hour at 50 uM with 5 uM protein, 1 mM β-ME and subjected to LC/MS analysis.

For the Finnigan MAT LCQ, the sample was injected (Gilson 215 autosampler and Agilent 1100 HPLC system) with a flow rate of 0.7 ml/min onto a Phenomenex Jupiter C5, 300 Angstrom, 5 mm, 50×2 mm column in 50% Solvent A (water/0.05% TFA)/50% Solvent B (CH₃CN/0.05% TFA) and subjected to a linear gradient to 5% Solvent A (water/0.05% TFA)/95% Solvent B (CH₃CN/0.05% TFA) over 0.75 minutes, followed by a linear gradient to 95% Solvent A/5% Solvent B over 0.25 minutes and then held for 1 min at 95% Solvent A.

For the API Qstar Pulsar I, the sample was injected (CTC Analytics PAL Systems autosampler and Agilent 1100 HPLC system) t-split to 25 μL/min onto a Phenomenex Jupiter C5, 300 Angstrom, 5 mm, 50×2 mm column in 90% Solvent A (water/0.1% formic acid)/10% Solvent B (CH₃CN/0.1% formic acid) and subjected to a linear gradient to 10% Solvent A (water/0.1% FA)/90% Solvent B (CH₃CN/0.1% FA) over 0.60 minutes, held there for 1.70 minutes, then followed by a linear gradient to 90% Solvent A/10% Solvent B over 0.20 minutes and then held for 0.80 min at 90% Solvent A.

EXAMPLE 10

This example describes the synthesis of the compound below

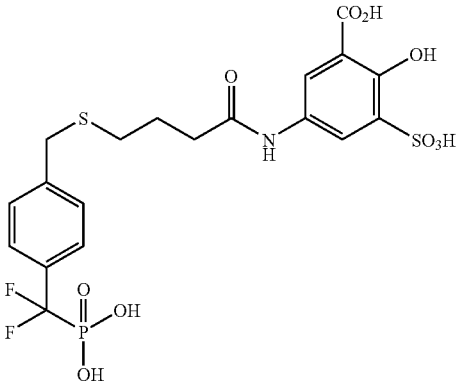

which was made according to Scheme D

SCHEME D

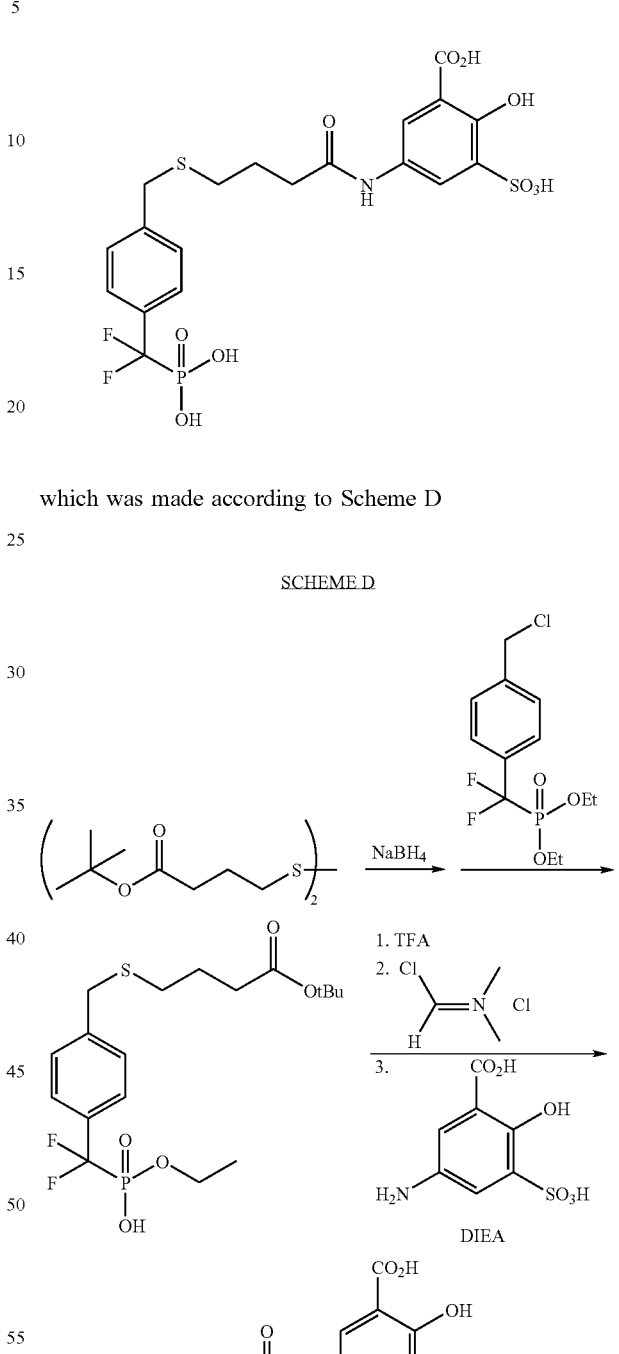

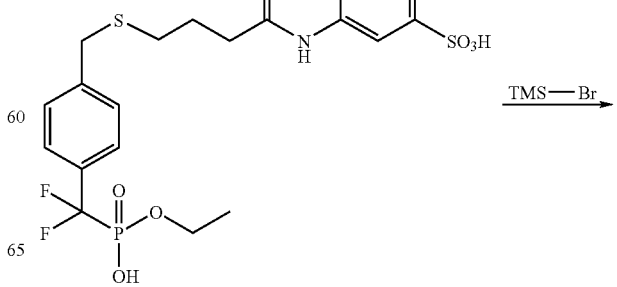

-continued

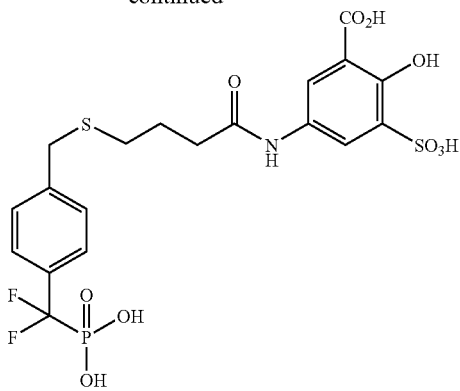

The t-butyl ester of 3-carboxypropyl disulfide was synthesized using the methods of Wright et al. (Stephen W. Wright, David L. Hagemean, Ann S. Wright, Lester D. McClure Tetrahedron Letters 38 (42) 7345–7348 (1997)). This disulfide (122 mg, 0.348 mmol) was reduced with sodium borohydride (17 mg, 0.449 mmol) under nitrogen for 5 minutes in 3 ml THF and 0.5 ml methanol. Next, the difluorophosphonyl benzyl chloride (200 mg, 0.64 mmol, synthesized according to the method of Caplan et al. (J. Chem. Soc. Perkin Trans. 1, 3 421–437 (2000)) was added in 1 ml THF. The reaction was allowed to stir for one hour at ambient temperature, at which time sodium hydroxide (0.07 ml of 10 N solution in water, 0.7 mmol) and more sodium borohydride (38 mg, 1 mmol) was added with 1 ml methanol. The reaction was allowed to proceed for three days under nitrogen, then flooded with 100 ml ethyl acetate, rinsed with 2×50 ml 1 M sodium hydrogen sulfate, 50 ml brine, dried over sodium sulfate, filtered and the solvent removed under reduced pressure to yield 218 mg of impure gum (ES (+) MS m/z=447 (M+Na)).

This material (208 mg) was suspended in 10 ml of DCM, chilled in an ice-water bath, and 10 ml of trifluoroacetic acid (TFA) was added. The reaction was stirred for 75 minutes and then solvent was removed under reduced pressure. The material was then resuspended in 3 ml dry dichloromethane and (chloromethylene)dimethyl ammonium chloride (71 mg, 0.555 mmol) was added, along with another 1 ml of DCM. The reaction was stirred at ambient temperature for 45 minutes, at which point 5-amino-2-hydroxy-3-sulfobenzoic acid (C012504, 128 mg, 0.549 mmol) and N,N-diisoproylethylamine (0.5 ml, 2.87 mmol) were added. The reaction was allowed to proceed overnight, at which point it was flooded with 70 ml 1 N HCl (aqueous) and extracted with 3×30 ml EtOAc. The aqueous layer was evaporated to reveal the product (ES (+) MS m/z=584 (M+H)). This was suspended in 15 ml of dry DCM, and bromotrimethylsilane (5.5 ml, 42 mmol) was added. After 14 hours the reaction was evaporated to dryness and purified via reverse-phase HPLC to yield the titled compound (8.1 mg, (ES (+) MS m/z=556 (M+H)) as an off-white solid.

EXAMPLE 11

Cloning of PTP-1B

PTP-1B (accession number SWS P18031) is a tyrosine phosphatase that has a C-terminal domain that is associated to the endoplasmic reticulum (ER) and a phosphatase domain that faces the cytoplasm. The proteins that it dephosphorylates are transported to this location by vesicles. The activity of PTP-1B is regulated by phosphorylation on serine and protein degradation. PTP-1B is a negative regulator of insulin signaling, and plays a role in the cellular response to interferon stimulation. This phosphatase may play a role in obesity by decreasing the sensitivity of organisms to leptin, thereby increasing appetite. Additionally, PTP-1B plays a role in the control of cell growth. A crystal structure has been solved for PTP-1B [IPTY, Puius, Y. A., et al., *Proc Natl Acad Sci USA* 94: 13420–13425 (1997)].

Full length human PTP-1B is 435 amino acids in length; the phosphotase domain comprises the first 298 amino acids. Because truncated portions of PTP-1B comprising the phosphotase domain is fully active, various truncated versions of PTP-1B are often used. A cDNA encoding the first 321 amino acids of human PTP-1B was isolated from human fetal heart total RNA (Clontech). Oligonucleotide primers corresponding to nucleotides 91 to 114 (Forward) and complementary to nucleotides 1030 to 1053 (Rev) of the PTP-1B cDNA [Genbank M31724.1, Chernoff, J., et al., *Proc. Natl. Acad. Sci. U.S.A.* 87: 2735–2739 (1990)] were synthesized and used to generate DNA using the polymerase chain reaction.

```
                                     SEQ ID NO: 1
Forward    GCCCATATGGAGATGGAAAAGGAGTTCGAG SEQ ID NO: 2
Rev        GCGACGCGAATTCTTAATTGTGTGGCTCCAGGATTCGTTT
```

The primer Forward incorporates an NdeI restriction site at the first ATG codon and the primer Rev inserts a UAA stop codon followed by an EcoRI restriction site after nucleotide 1053. cDNAs were digested with restriction nucleases NdeI and EcoRI and cloned into pRSETc (Invitrogen) using standard molecular biology techniques. The identity of the isolated cDNA was verified by DNA sequence analysis (methodology is outlined in a later paragraph).

A shorter cDNA, PTP-1B 298, encoding amino acid residues 1–298 was generated using oligonuclotide primers Forward and Rev2 and the clone described above as a template in a polymerase chain reaction.

```
Rev2
TGCCGGAATTCCTTAGTCCTCGTGGGAAAGCTCC    SEQ ID NO: 3
```

EXAMPLE 12

PTP-1B Mutants

Site-directed mutants of PTP-1B (amino acids 1–321), PTP-1B 298 (amino acids 1–298) and PTP-1B 298-2M (with Cys32 and Cys92 changed to Ser and Ala, respectively) were prepared by the single-stranded DNA method (modification of Kunkel, 1985). 298-2M was made with the following oligonucleotides:

```
C32S    CTTGGCCACTCTAGATGGGAAGTCACT    SEQ ID NO: 4

C92A    CCAAAAGTGACCGGCTGTGTTAGGCAA    SEQ ID NO: 5
```

The R47C mutant was made with the following oligonucleotide:

```
R47C    GGGACTGACGTCACAGTACCTATTTCG    SEQ ID NO: 6
```

Oligonucleotides were designed to contain the desired mutations and 12 bases of flanking sequence on each side of the mutation. The single-stranded form of the PTP-1B/ pRSET, PTP-1B 298/pRSET and PTP-1B 298-2M/pRSET plasmid was prepared by transformation of double-stranded plasmid into the CJ236 cell line (1 μl double-stranded plasmid DNA, 2 μl 5×KCM salts, 7 μl water, 10 μl PEG-DMSO competent CJ236 cells; incubated on ice for 20 minutes followed by 25° C. for 10 minutes; plated on LB/agar with 100 μg/ml ampicillin and incubated at 37° C. overnight). Single colonies of CJ236 cells were then grown in 100 ml 2YT media to midlog phase; 5 μl VCS helper phage (Stratagene) were then added and the mixture incubated at 37° C. overnight. Single-stranded DNA was isolated from the supernatant by precipitation of phage (⅕ volume 20% PEG 8000/2.5M NaCl; centrifuge at 12K for 15 minutes). Single-stranded DNA was then isolated from phage using Qiagen single-stranded DNA kit.

Site-directed mutagenesis was accomplished as follows. Oligonucleotides were dissolved in TE (10 mM Tris pH 8.0, 1 mM EDTA) to a concentration of 10 OD and phosphorylated on the 5' end (2 μl oligonucleotide, 2 μl 10 mM ATP, 2 μl 10× Tris-magnesium chloride buffer, 1 μl 100 mM DTT, 12.5 μl water, 0.5 μl T4 PNK; incubate at 37° C. for 30 minutes). Phosphorylated oligonucleotides were then annealed to single-stranded DNA template (2 μl single-stranded plasmid, 0.6 μl oligonucleotide, 6.4 μl water; heat at 94° C. for 2 minutes, slow cool to room temperature). Double-stranded DNA was then prepared from the annealed oligonucleotide/template (add 2 μl 10× TM buffer, 2 μl 2.5 mM dNTPs, 1 μl 100 mM DTT, 0.5 μl 10 mM ATP, 4.6 μl water, 0.4 μl T7 DNA polymerase, 0.2 μl T4 DNA ligase; incubate at room temperature for two hours). E. coli (XL1 blue, Stratagene) were then transformed with the double-stranded DNA (5 μl double-stranded DNA, 5 μl 5×KCM, 15 μl water, 25 μl PEG-DMSO competent cells; incubate 20 minutes on ice, 10 min. at room temperature), plated onto LB/agar containing 100 μg/ml ampicillin, and incubated at 37° C. overnight. Approximately four colonies from each plate were used to inoculate 5 ml 2YT containing 100 μg/ml ampicillin; these cultures were grown at 37° C. for 18–24 hours. Plasmids were then isolated from the cultures using Qiagen miniprep kit. These plasmids were sequenced to determine which clones contained the desired mutation.

Mutant proteins were expressed as follows. PTP-1B clones were transformed into BL21 codon plus cells (Stratagene) (1 μl double-stranded DNA, 2 μl 5×KCM, 7 μl water, 10 μl DMSO competent cells; incubate 20 minutes at 4° C., 10 minutes at room temperature), plated onto LB/agar containing 100 μg/ml ampicillin, and incubated at 37° C. overnight. 2 single colonies were picked off the plates or from frozen glycerol stocks of these mutants and inoculated in 100 ml 2YT with 50 μg/ml carbenicillin and grown overnight at 37° C. 50 ml from the overnight cultures were added to 1.5 L of 2YT/carbenicillin (50 μg/ml) and incubated at 37° C. for 3–4 hours until late-log phase (absorbance at 600 nm ~0.8–0.9). At this point, protein expression was induced with the addition of IPTG to a final concentration of 1 mM. Cultures were incubated at 37° C. for another 4 hours and then cells were harvested by centrifugation (7K rpm, 7 minutes) and frozen at −20° C. PTP-1B proteins were purified from the frozen cell pellets as described in the following. First, cells were lysed in a microfluidizer in 100 ml of buffer containing 20 mM MES pH 6.5, 1 mM EDTA, 1 mM DTT, and 10% glycerol buffer (with 3 passes through a Microfluidizer [Microfluidics, 110S]) and inclusion bodies were removed by centrifugation (10K rpm; 10 minutes). Purification of all PTP-1B mutants was performed at 4° C. The supernatants from the centrifugation were filtered through 0.45 μm cellulose acetate (5 μl of this material was analyzed by SDS-PAGE) and loaded onto an SP Sepharose fast flow column (2.5 cm diameter×14 cm long) equilibrated in Buffer A (20 mM MES pH 6.5, 1 mM EDTA, 1 mM DTT, 1% glycerol) at 4 ml/min.

The protein was then eluted using a gradient of 0–50% Buffer B over 60 minutes (Buffer B: 20 mM MES pH 6.5, 1 mM EDTA, 1 mM DTT, 1% glycerol, 1 M NaCl). Yield and purity was examined by SDS-PAGE and, if necessary, PTP-1B was further purified by hydrophobic interaction chromatography (HIC). Protein was supplemented with ammonium sulfate until a final concentration of 1.4 M was reached. The protein solution was filtered and loaded onto an HIC column at 4 ml/min in Buffer A2: 25 mM Tris pH 7.5, 1 mM EDTA, 1.4 M $(NH_4)_2SO_4$, 1 mM DTT. Protein was eluted with a gradient of 0–100% Buffer B over 30 minutes (Buffer B2: 25 mM Tris pH 7.5, 1 mM EDTA, 1 mM DTT, 1% glycerol). Finally, the purified protein was dialyzed at 4° C. into the appropriate assay buffer (25 mM Tris pH 8, 100 mM NaCl, 5 mM EDTA, 1 mM DTT, 1% glycerol). Yields varied from mutant to mutant but typically were within the range of 3–20 mg/L culture.

EXAMPLE 13

This example describes the synthesis of the compound below

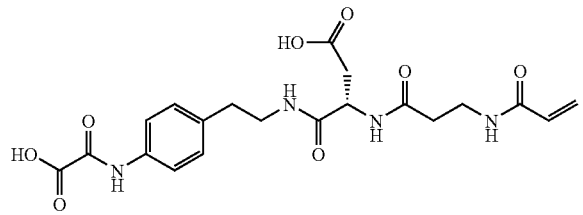

which was made according to Scheme E.

SCHEME E

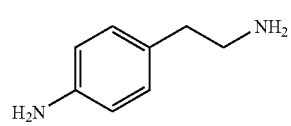 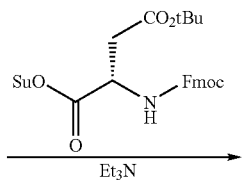

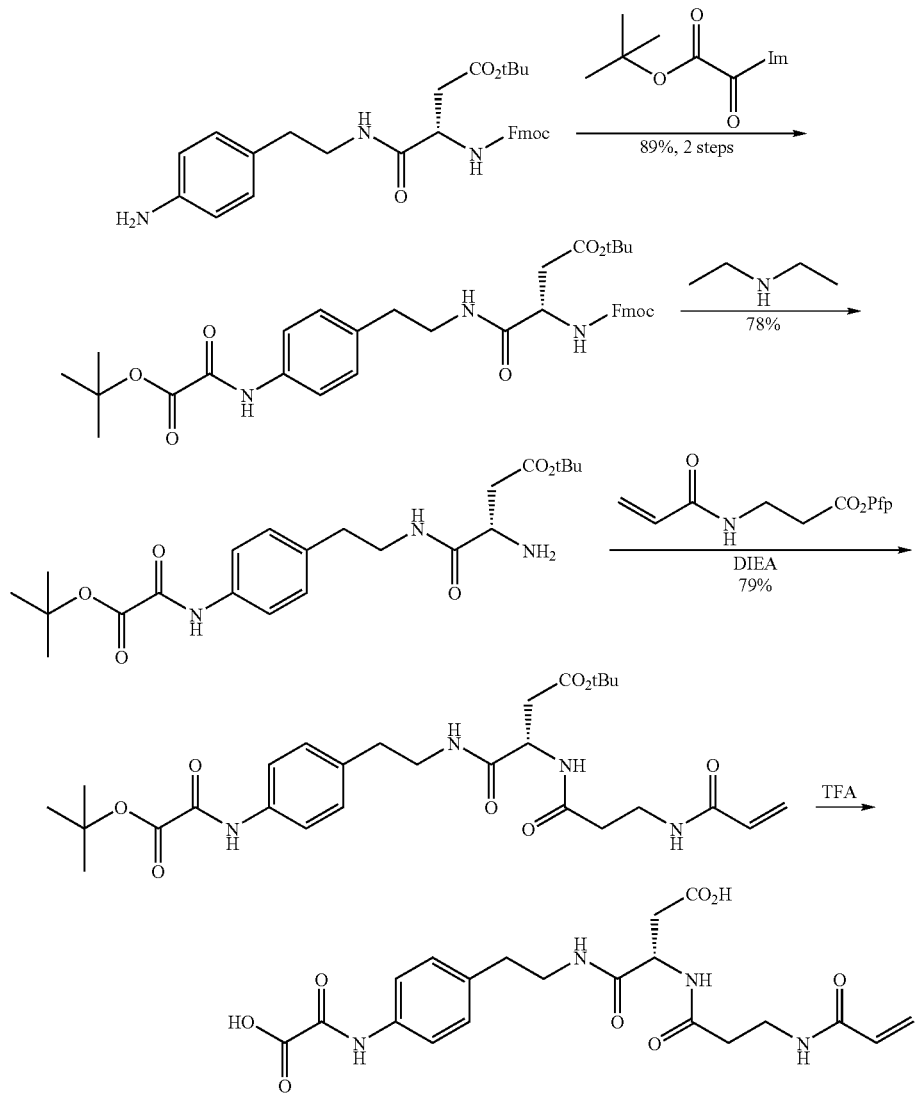

Commercially available 2-(4-aminophenyl)-ethylamine (0.69 ml, 5.24 mmol) was reacted with Fmoc-Asp(OtBu)-OSu (2.64 g, 5.19 mmol, Chem-Impex) and triethylamine (0.75 ml, 5.4 mmol) in 20 ml DCM for 30 minutes. The reaction was flooded with 80 ml DCM, rinsed with 2×50 ml saturated sodium bicarbonate, 50 ml brine, dried over sodium sulfate, and solvent was removed under reduced pressure to yield product quantitatively ((+) MS m/z=552 (M+Na)).

This was converted to the oxalamate using the oxalamating reagent described by Mosher (Jonathan S. Nimitz and Harry S. Mosher, J. Org. Chem. 1981 46 211–213) to yield a white foam (3.0 g, 4.61 mmol, 89%, (+) MS m/z=680 (M+Na)).

The Fmoc protecting group was removed with diethylamine (20 ml, 193 mmol) in DCM (20 ml) by reacting for 16 hours, at which point the reaction was evaporated to dryness and purified using flash chromatography on silica gel with 95:5 DCM:MeOH (0.1 M ammonia) to yield the amine as an off-white foam (1.55 g, 3.55 mmol, 78%, (+) MS m/z=436 (M+Na)).

The activated acrylamide was synthesized according to Scheme F.

SCHEME F

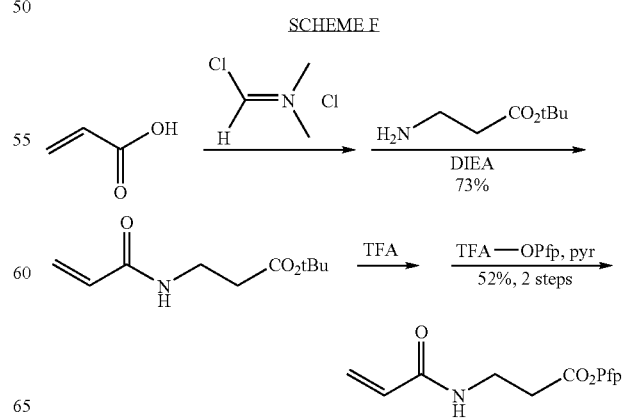

Acrylic acid (0.5 ml, 7.29 mmol) was reacted with (chloromethylene)dimethyl ammonium chloride (1.12 g, 8.75 mmol) in 20 ml DCM for 25 minutes, followed by addition of β-alanine-OtBu-hydrochloride (1.6 g, 8.8 mmol) and diisopropylethylamine (3.0 ml, 17.2 mmol). After 15 hours the reaction was flooded with DCM (60 ml), rinsed with 2×50 ml 1 M sodium hydrogen sulfate, 2×50 ml saturated sodium bicarbonate, 50 ml brine, dried over sodium sulfate, and solvent removed under reduced pressure to yield product (1.07 g, 5.36 mmol, 73%, (+) MS m/z=222 (M+Na)). This was then redissolved in 20 ml dry DCM, chilled in an ice-water bath, and reacted with 20 ml trifluoroacetic acid for 30 minutes. The reaction mixture was then evaporated to dryness, redissolved in DMF (5 ml), and pyridine (1.2 ml, 14.8 mmol) and pentafluorophenyl trifluoroacetate (1 ml, 5.8 mmol) were added. The reaction was allowed to proceed for 40 minutes, then flooded with EtOAc (75 ml), rinsed with 2×25 ml 1 M sodium hydrogen sulfate, 2×25 ml saturated sodium bicarobonate, 25 ml brine, dried over sodium sulfate, filtered, evaporated to dryness, and purified using flash chromatography with 60:40 hexane:EtOAc to yield a white crystalline solid (0.799 g, 2.58 mmol, 52%, (+) MS m/z=310 (M+H)).

The activated acrylamide (199 mg, 0.644 mmol) was reacted with the amine (282 mg, 0.648 mmol) and diisopropylethylamine (0.14 ml, 0.804 mmol) in 5 ml DCM for 14 hours, at which time the reaction was flooded with 50 ml EtOAc, rinsed with 2×25 ml 1 M sodium hydrogen sulfate, 25 ml saturated sodium bicarbonate, 25 ml brine, dried over sodium sulfate, filtered, evaporated to dryness, and purified using flash chromatography on silica gel with 95:5 DCM:MeOH to yield a colorless resin (288 mg, 0.514 mmol, 79% (+) MS m/z=561 (M+H)).

This material was dissolved in 10 ml DCM, chilled in an ice-water bath, and deprotected with trifluoroacetic acid (10 ml). The reaction was then removed from the ice-water bath and allowed to stir at room temperature for 40 minutes before being evaporated to dryness and purified using reverse-phase HPLC to yield the titled compound as a white solid (47 mg, (+) MS m/z=449 (M+H)).

EXAMPLE 14

This example describes the synthesis of the compound below

This compound was made using the method of Example 13 except that the disulfide linker was used instead of the acrylamide linker (ES (+) MS m/z=544 (M+H)).

EXAMPLE 15

This example describes the synthesis of the compound below

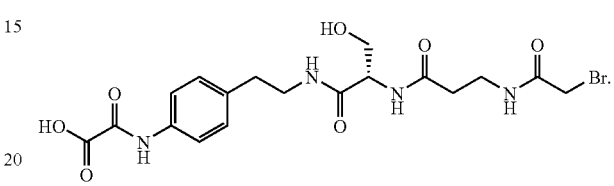

This compound was made using the method of Example 3 except that the brocoacetamide linker was used instead of the acylamide linker (ES (+) MS m/z=489 (M+H)).

EXAMPLE 16

This example describes the synthesis of the compound below

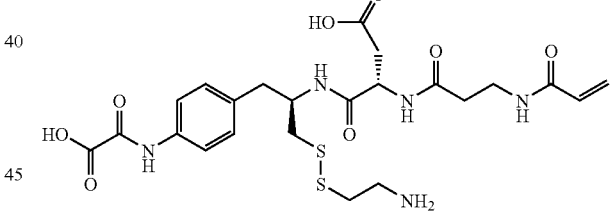

which was made according to Scheme G.

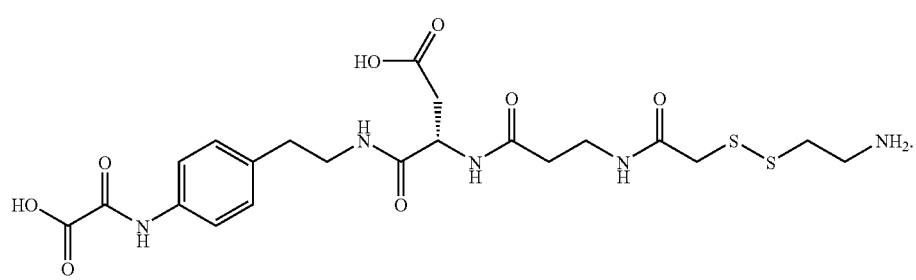

SCHEME G

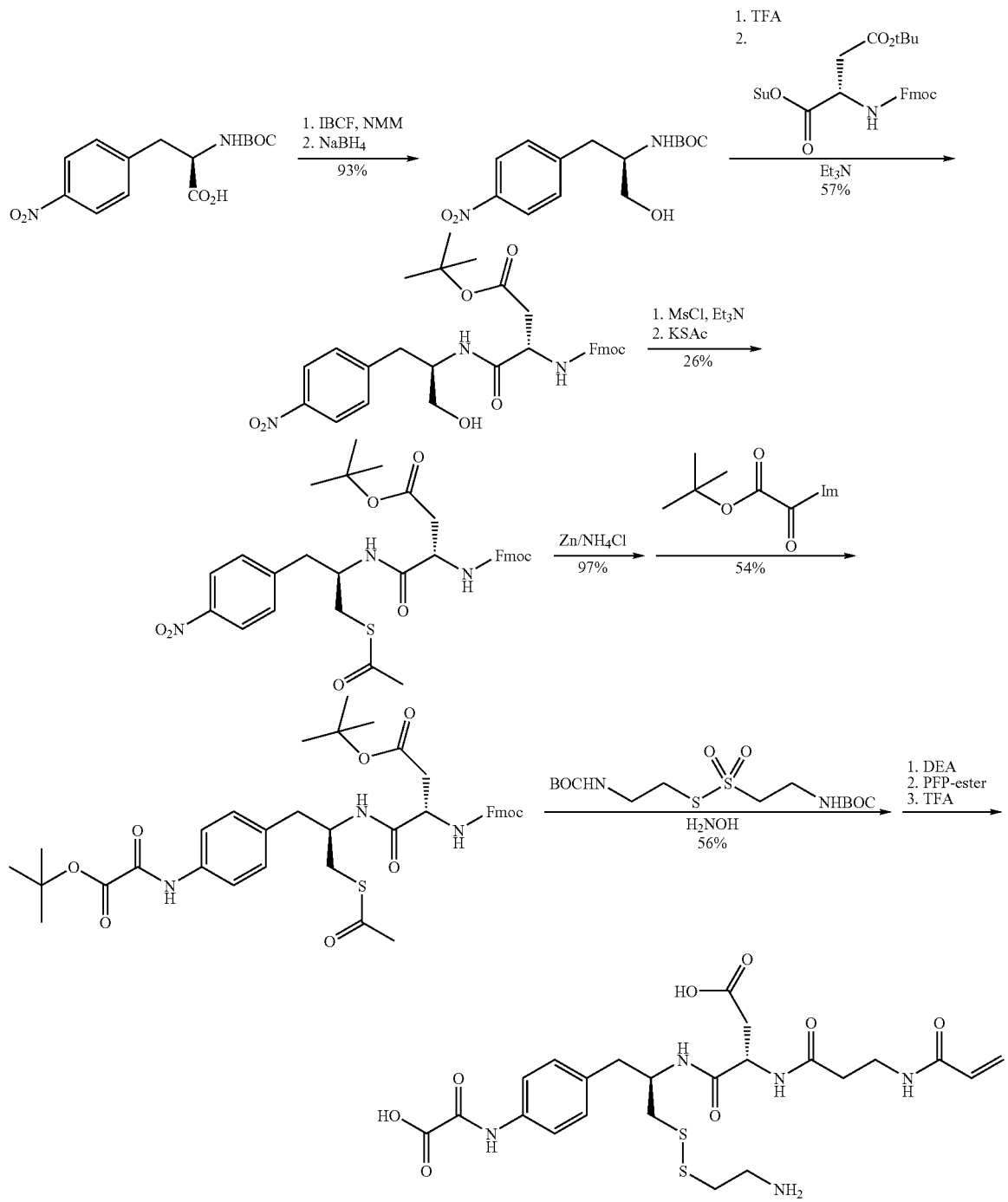

Commercially available Boc-D-Phe(4-nitro)—OH (2.05 g, 6.61 mmol, Chem-Impex) was dissolved in 30 ml dry THF, chilled in an ice-water bath, and reacted with N-methylmorpholine (0.74 ml, 6.73 mmol) and isobutyl chloroformate (0.86 ml, 6.63 mmol). The reaction was stirred on ice for 20 minutes, then filtered through a medium glass frit and the precipitate rinsed with 2×5 ml THF. The combined filtrates were then cooled in an ice-water bath again and reduced with sodium borohydride (1.25 g, 33 mmol) along with 7 ml methanol. The reaction was allowed to proceed for 10 minutes, quenched with 50 ml 1 M sodium hydrogen sulfate (aqueous), and extracted with 100 ml EtOAc. The organics were then rinsed with 50 ml 1 M sodium hydrogen sulfate, 50 ml saturated sodium bicarbonate, and 50 ml brine, dried over sodium sulfate, filtered, and evaporated to dryness to yield product alcohol (1.82 g, 6.15 mmol, 93%, ES (+) MS m/z=319 (M+Na).

This alcohol was suspended in 40 ml DCM, chilled in an ice-water bath, and treated with 25 ml trifluoroacetic acid. The reaction was warmed to room temperature and allowed to proceed for 25 minutes, and then evaporated to dryness.

The material was then resuspended in 20 ml DCM and reacted with triethylamine (2.6 ml, 18.7 mmol) and Fmoc-Asp(OtBu)-OSu (3.18 g, 6.25 mmol) along with another 20 ml DCM. The reaction was allowed to proceed for 40 minutes and then flooded with 60 ml DCM, rinsed with 50 ml 1 M sodium hydrogen sulfate, 50 ml saturated sodium bicarbonate, and 50 ml brine, dried over sodium sulfate, filtered, and solvent removed under reduced pressure. The residue was purified by flash chromatography on silica gel using 95:5 DCM:MeOH to yield product (2.05 g, 3.48 mmol, 57%, ES (+) MS m/z=612 (M+Na).

The alcohol was dissolved in 50 ml DCM, chilled in an ice-water bath, and treated with triethylamine (0.56 ml, 4.02 mmol) and methanesulfonyl chloride (0.3 ml, 3.88 mmol). The reaction was allowed to proceed on ice for 30 minutes before being flooded with 50 ml DCM, rinsed with 50 ml 1 M sodium hydrogen sulfate, 50 ml saturated sodium bicarbonate, 50 ml brine, dried over sodium sulfate, filtered, and the solvent removed under reduced pressure to yield a yellow solid. This was dissolved in 10 ml DMF and treated with potassium thioacetate (0.42 g, 3.68 mmol) and 10 ml more DMF. The reaction was allowed to proceed for 18 hours before being flooded with 100 ml EtOAc, rinsed with 2×50 ml 1 M sodium hydrogen sulfate, 2×50 ml saturated sodium bicarbonate, 50 ml brine, dried over sodium sulfate, evaporated to dryness, and purifed using flash chromatography on silica gel with 70:30 hexane:EtOAc to obtain the thioester as a yellow solid (0.588 g, 0.908 mmol, 26%, two steps, ES (+) MS m/z=670 (M+Na).

The nitro group was selectively reduced by dissolving the above compound (0.464 g, 0.716 mmol) in 5 ml methanol, chilling in an ice-water bath, and adding ammonium chloride (0.773 g, 14.5 mmol) and zinc dust (0.244 g, 3.73 mmol) along with another 15 ml methanol. The reaction was slowly allowed to warm to room temperature and allowed to proceed overnight under nitrogen, at which point it was filtered through celite and evaporated. The residue was redissolved in 100 ml EtOAc, rinsed with 3×50 ml saturated sodium bicarbonate, 50 ml brine, dried over sodium sulfate, filtered, and evaporated to a yellow foam (0.43 g, 0.696 mmol, 97%, ES (+) MS m/z=618 (M+H)).

The xalamate was installed as described in Scheme E and purified using flash chromatography, first with 70:30 hexane:EtOAc, then 50:50 hexane:EtOAc to yield product as a light yellow foam (0.280 mg, 0.375 mmol, 54%, ES (+) MS m/z=768 (M+Na).

The cystamine-based-thiosulfonate was synthesized by dissolving N-Boc-cysteamine (25.7 g, 145 mmol) in dimethylsulfoxide (DMSO, 50 ml, 704 mmol) and heating to 70 degrees C. for 4 days open to the air. The reaction was then flooded with 300 ml EtOAc, rinsed with 3×100 ml water, 100 ml brine, dried over sodium sulfate, filtered, and evaporated to dryness to produce the disulfide as a white solid (25 g, 71 mmol, 98%). This was oxidized to the thiosulfonate by dissolving it in 400 ml DCM, chilling the reaction in an ice-water bath, and adding meta-chloro-peroxybenzoic acid (64 g of 77% commercial material from Aldrich, 286 mmol) in portions over 15 minutes. As precipitate formed 200 ml more DCM was also added. After 3 hours the reaction was filtered through a glass frit and the precipitate washed with 3×50 ml DCM. The combined filtrate was rinsed with 2×100 ml saturated sodium bicarbonate, 2×100 ml 50% saturated sodium bicarbonate, 100 ml water, and 100 ml brine, dried over sodium sulfate, filtered, and evaporated to a viscous yellow syrup which slowly solidified to a hard crystalline solid over the course of a week (14.7 g, 38.2 mmol, 54%, ES (+) MS m/z=407 (M+Na)).

The thioester was converted to a disulfide by dissolving it (0.272 g, 0.365 mmol) in 5 ml ethanol and adding the thiosulfonate described above. This was then sparged under nitrogen, and hydroxylamine (0.1 ml, 1.63 mmol, 50% in water) was added. The reaction was allowed to proceed for three hours, at which point it was flooded with EtOAc (50 ml), rinsed with 3×25 ml saturated sodium bicarbonate, 25 ml brine, dried over sodium sulfate, filtered, evaporated to dryness, and purified using flash chromatography on silica gel with 70:30 hexane:EtOAc to yield an off-white foam (0.179 g, 0.204 mmol, 56%, ES (+) MS m/z=901 (M+Na)).

The Fmoc group was removed by dissolving the material in 5 ml DCM and reacting it with diethylamine (5 ml, 48 mmol) for 15 hours. The reaction was then evaporated to dryness and purified by flash chromatography on silica gel with 95:5 DCM:MeOH (0.1 M ammonia). The amine was obtained as an off-white foam (0.117 g, 0.178 mmol, 89%, ES (+) MS m/z=657 (M+H)).

The amine (0.114 g, 0.174 mmol) was coupled to the acrylamide active ester (0.067 g, 0.217 mmol) described earlier (Scheme E) in DCM (5 ml) with diisopropylethylamine (0.05 ml, 0.287 mmol) for 69 hours. The reaction was then flooded with 50 ml EtOAc, rinsed with 2×25 ml 1 M sodium hydrogen sulfate, 2×25 ml saturated sodium bicarbonate, 25 ml brine, dried over sodium sulfate, filtered, evaporated to dryness, and purified using flash chromatography on silica gel with 95:5 DCM:MeOH to obtain product quantitatively (ES (+) MS m/z=782 (M+H)).

This material was globally deprotected by dissolving it in DCM (10 ml), chilling it in an ice-water bath, and adding 10 ml trifluoroacetic acid. The reaction was then warmed to room temperature and allowed to proceed for 35 minutes before being evaporated to dryness and purified by reverse-phase HPLC to obtain the titled compound as a white solid (0.039 g, 0.056 mmol, 32%, ES (+) MS m/z=569 (M+H)).

EXAMPLE 17

This example describes the synthesis of the compound below

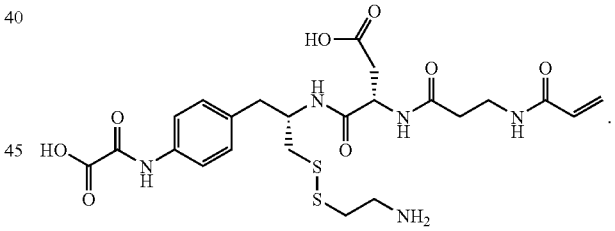

This compound was made using the method of Example 16 except that the S-enantiomer of Boc-Phe(4-nitro)—OH was used (ES (+) MS m/z=569 (M+H)).

EXAMPLE 18

This example describes the synthesis of the compound below

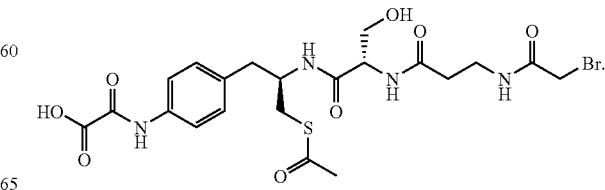

which was made according to Scheme H.

SCHEME H

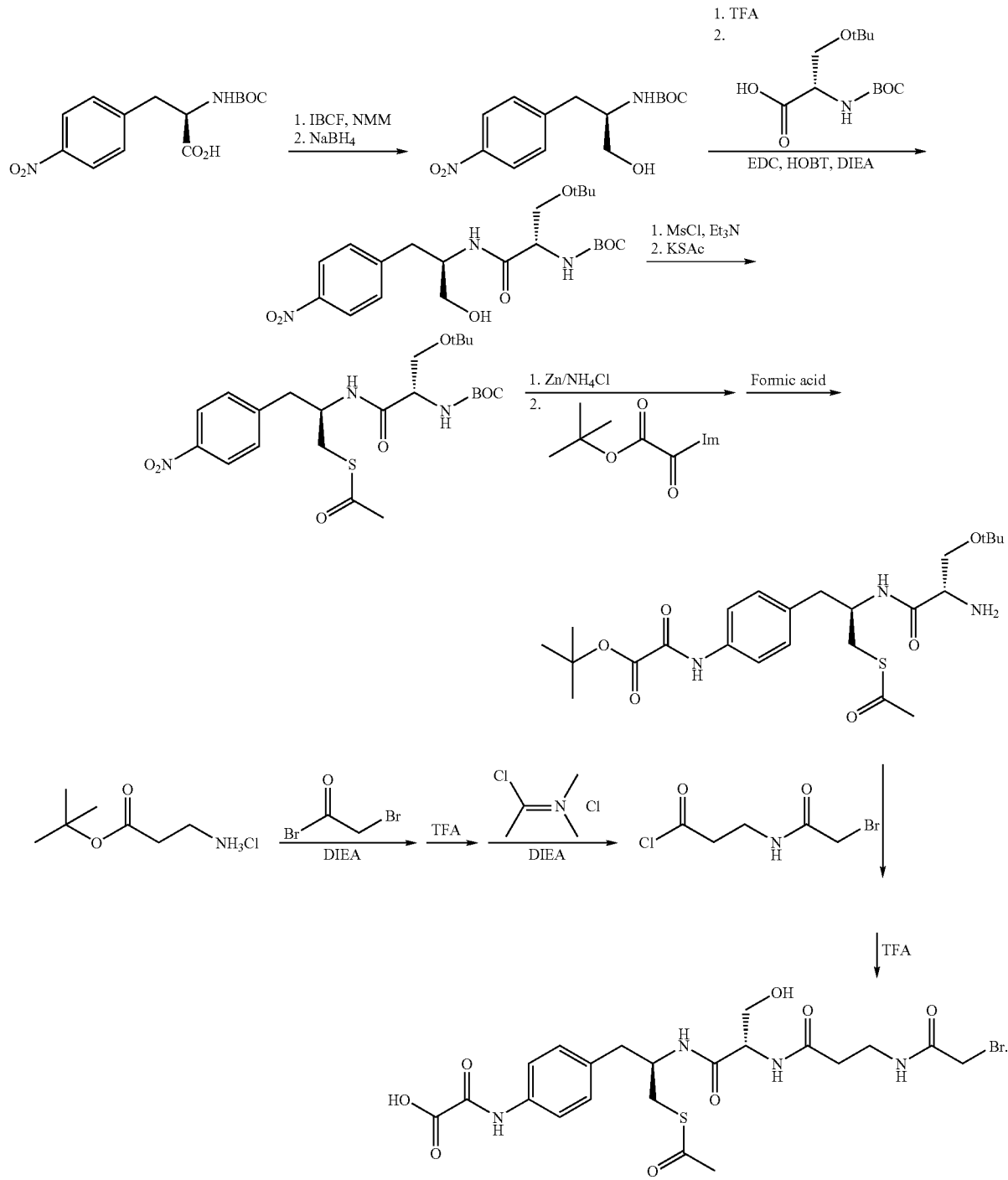

This method is similar to the method of Example 13 except for the following. The H₂N-Phe(4-nitro)—CH₂OH was conjugated to Boc-Ser(OtBu)—OH using an EDC coupling. This was done by dissolving Boc-Ser(OtBu)—OH (1.75 g, 6.7 mmol), HOBT (0.99 g, 7.33 mmol) and EDC (1.4 g, 7.3 mmol) in 20 ml dry DMF. The freshly deprotected H₂N-Phe(4-nitro)—CH₂OH was then dissolved in 10 ml dry DMF and N,N-diisopropylethylamine (DIEA, 3.7 ml, 21.2 mmol) was added. This amine solution was added to the activated acid solution along with another 10 ml dry DMF, and the reaction was allowed to stir for 40 minutes at ambient temperature. The reaction was then flooded with 100 ml EtOAc, rinsed with 2×50 ml 1 M sodium hydrogen sulfate, 2×50 ml saturated sodium bicarbonate, and 50 ml saturated sodium chloride, dried over sodium sulfate, filtered, and evaporated to dryness to yield product which was used without further purification (ES (+) MS m/z=462 (M+Na)).

The bromoacetamide portion of the molecule was constructed as follows. H-β-Ala-OtBu (1.01 g, 5.56 mmol) was dissolved in 40 ml dry DCM, chilled in an ice-water bath, and then DIEA (2.0 ml, 11.5 mmol) and bromoacetylbromide (0.49 ml, 5.63 mmol) were added and the reaction allowed to proceed on ice for 30 minutes. The reaction was then flooded with 60 ml DCM, rinsed with 2×50 ml saturated sodium bicarbonate and 50 ml brine, dried over sodium sulfate, filtered, and evaporated to dryness. The resulting product was purified by flash chromatography using 60:40 hexane: EtOAc to yield a pale yellow liquid (1.198 g, 4.5 mmol, 81%, ES (+) MS m/z=288 (M+Na)). The t-butyl protecting group was removed by dissolving the ester in 20 ml dry DCM, chilling the reaction in an ice-water bath, and adding 20 ml TFA. The reaction was allowed to stir for 30 minutes and then evaporated to dryness to yield the free acid as a light tan syrup which was used without further purification (ES (+) MS m/z=212 (M+H)).

After installation of the oxalamate functionality, the Boc-group of the serine was selectively removed by treating the peptide (97 mg, 0.163 mmol) with neat formic acid (4 ml) at ambient temperature for 20 minutes. The formic acid was then removed by rotary evaporation. Meanwhile, the bromoacetamide-containing acid fragment was activated by dissolving it (89 mg, 0.334 mmol) in 2 ml dry DCM, adding Villsmeier Reagent (46 mg, 0.359 mmol), and 3 ml more DCM and allowing the reaction to proceed for 5 minutes. The freshly deprotected peptide redissolved in DCM was then added along with DIEA (0.2 ml, 1.15 mmol). The coupling reaction was allowed to proceed for only 10 minutes, then evaporated to dryness, redissolved in 50 ml EtOAc, rinsed with 2×25 ml 1 M sodium hydrogen sulfate, 2×25 ml saturated sodium bicarbonate, and 25 ml brine, dried over sodium sulfate, filtered, and evaporated to dryness. The product was purified using flash chromatography, first with 80:20 EtOAc: hexane, then pure EtOAc, and finally 95:5 DCM: MeOH. Pure product was obtained as a light yellow foam (20 mg, 0.029 mmol, 18%, ES (+) MS m/z=689 (M+H)).

This material was dissolved in 10 ml dry DCM and treated with 10 ml TFA. The reaction was allowed to proceed for 1.75 hours, at which point it was evaporated to dryness and the product purified by reverse-phase HPLC to obtain SP-5899 as a white solid (3.6 mg, 0.0062 mmol, 21%, ES (+) MS m/z=577 (M+H)).

EXAMPLE 19

This example describes the synthesis of the compound below

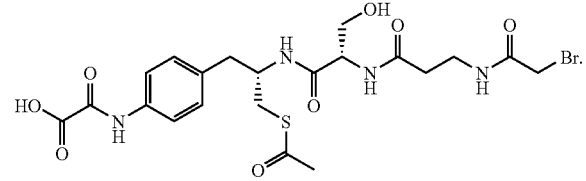

This compound was made using the method of Example 16 except that the S-enantiomer of Boc-Phe(4-nitro)—OH was used (ES (+) MS m/z=577 (M+H)).

EXAMPLE 20

This example describes the synthesis of the compound below

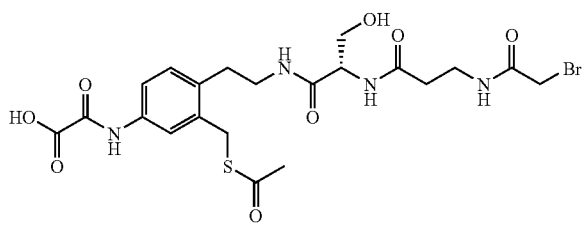

which was made according to Scheme I.

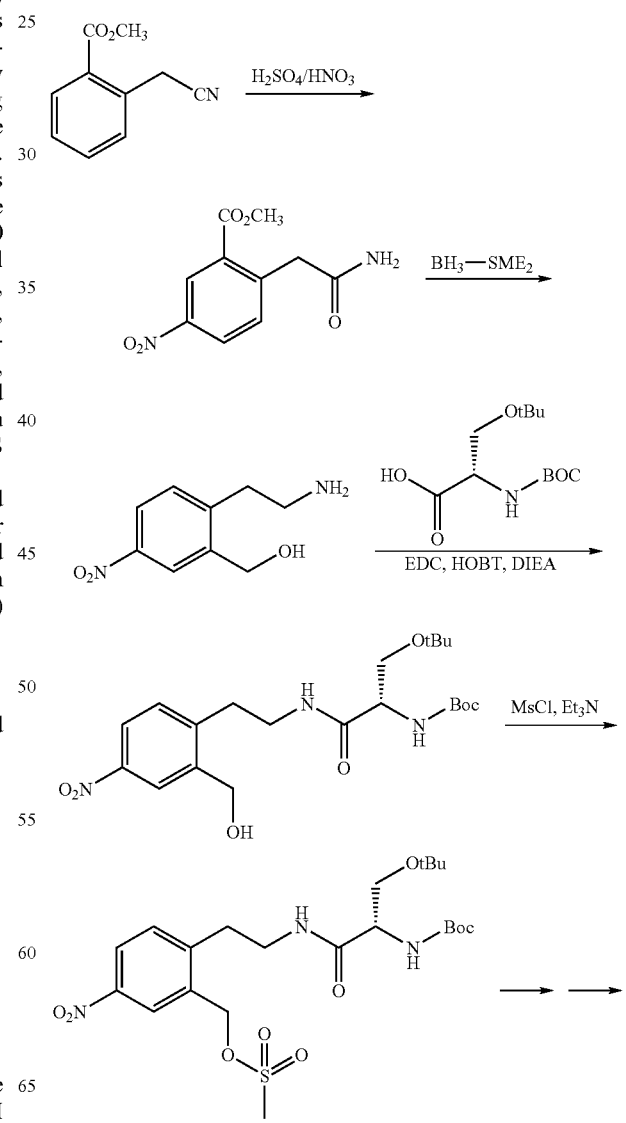

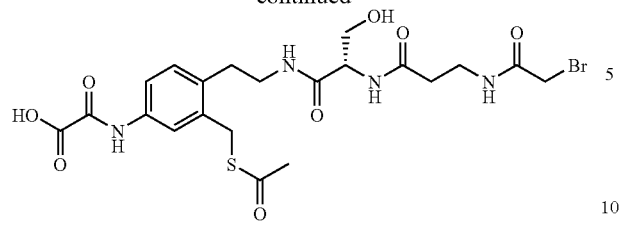

2-cyanomethyl benzoic acid methyl ester (6.03 g, 34.4 mmol) was cooled in an ice water bath, to which was added concentrated sulfuric acid (25 ml) and 70% nitric acid (3 ml). The reaction was allowed to proceed on ice for 40 minutes, at which point it was poured onto ice (50 grams) and flooded with water (50 ml) and EtOAc (50 ml). This mixture was stirred vigorously on ice and then filtered through a medium glass frit. The precipitate was washed with 2×25 ml EtOAc and dried under reduced pressure to yield an off-white solid (1.96 g, 8.24 mmol, 24%, ES (+) MS m/z=261 (M+Na)) which was used without further purification.

The nitrobenzene compound (1.89 g, 7.93 mmol) was transferred to a teflon-capped glass "bomb," and a solution of 1 M borane methyl sulfide complex in THF was added (32 ml, 64 mmol). The bomb was sealed and heated to 65 deg. C. for 14 hours. The bomb was then cooled in an ice-water bath, carefully opened, and the reaction very carefully quenched with methanol (10 ml) and concentrated HCl (10 ml). The solution was then heated to 65 deg. C. for 30 minutes, after which point the acid was neutralized with 1 N NaOH (140 ml) and the mixture extracted with 4×30 ml EtOAc. The combined organic layers were rinsed with 3×50 ml 1 N NaOH and 50 ml saturated NaCl, dried over sodium sulfate, filtered, and evaporated to dryness to yield the amino alcohol as an orange liquid (100%, ES (+) MS m/z=197 (M+H)). The remaining steps were carried out using the corresponding method as described for the compound in Example 17 to yield the titled compound (ES (+) MS m/z=577 (M+H)).

EXAMPLE 21

This example describes the synthesis of the compound below

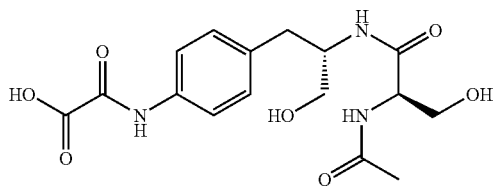

which was made according to Scheme J

SCHEME J

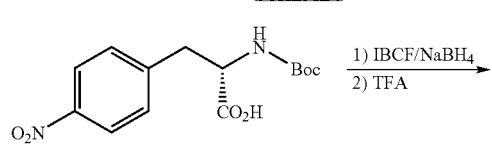

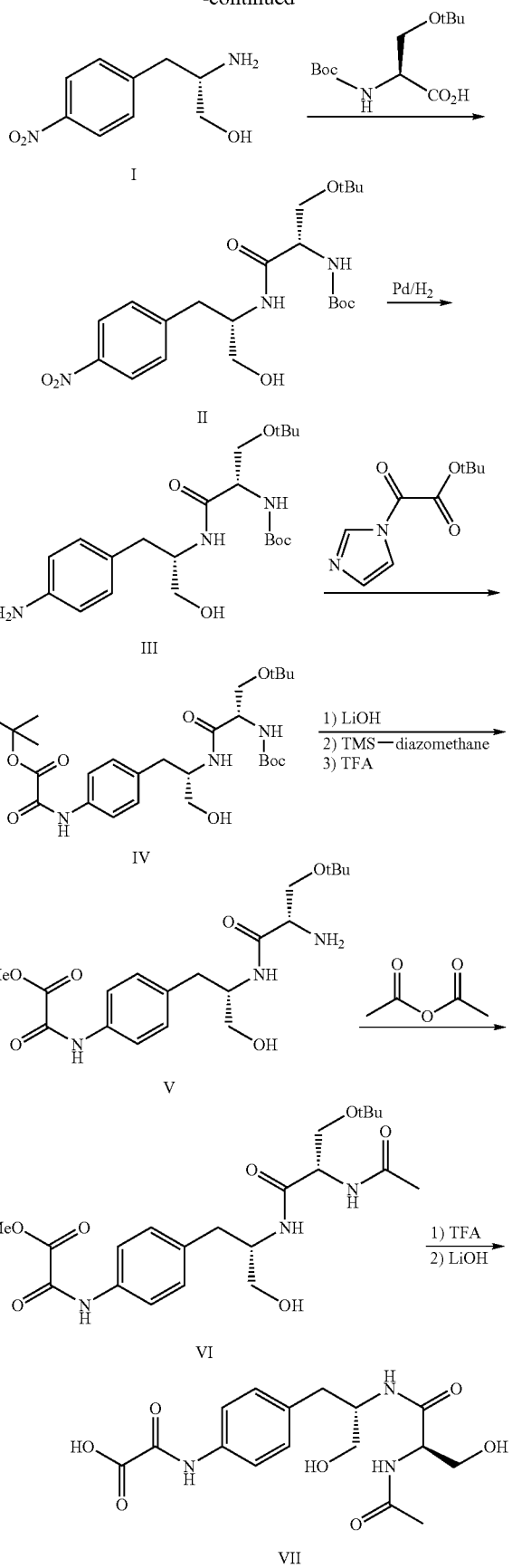

a) Boc-4-nitro-D-phenylalanine (5.0 g, 16.11 mmol) was dissolved in 75 mL THF and cooled to 0° C. under a nitrogen atmosphere. N-methylmorpholine (1.81 mL, 16.43 mmol) was added followed by isobutylchloroformate (ICBF) (2.11 mL, 16.27 mmol). The reaction was stirred at 0° C. for 15 minutes and then filtered through a coarse glass frit funnel. Sodium borohydride (3.04 g, 80.39 mmol) was added to the filtrate and the solution stirred for 20 minutes at 0° C. The reaction was flooded with 100 mL 1 M NaHSO$_4$ and extracted with 3×30 mL EtOAc. The combined organic layers were washed with 30 mL 1 M NaHSO$_4$, 30 mL saturated NaHCO$_3$, 30 mL brine, dried over anhydrous Na$_2$SO$_4$, filtered, and the solvent removed under reduced pressure. The resulting residue was dissolved in 10 mL DCM and 10 mL TFA was added. The solution was stirred for 1 hour at which point the solvent was removed under reduced pressure to yield Compound I in quantitative yield, ES (+) MS m/e=197 (M+H) which was used without further purification.

b) Compound I (2.98 g, 15.19 mmol) was dissolved in 15 mL DMF and DIEA (13.23 mL, 75.95 mmol) was added. This solution was added to a mixture of Boc-O-(t-butyl ether)-L-serine (4.36 g, 16.71 mmol), 1-ethyl-(3-dimethylaminopropyl)carbodiimide hydrochloride (3.49 g, 18.23 mmol) and 1-hydroxybenzotriazole (2.46 g, 18.23 mmol) in 75 mL DMF. This solution was stirred at ambient temperature for 1 hour at which point it was flooded with 200 mL EtOAc, rinsed with 2×50 mL 1 M NaHSO$_4$, 2×50 mL saturated NaHCO$_3$, 50 mL brine, dried over anhydrous Na$_2$SO$_4$, filtered, and the solvent removed under reduced pressure to yield Compound II (5.73 g, 13.04 mmol, 86%), ES (+) MS m/e=462 (M+Na) which was used without further purification.

c) Compound II (5.73 g, 13.04 mmol) was dissolved in 50 mL MeOH and palladium on carbon (2.77 g, 1.30 mmol) was added. The reaction was stirred at ambient temperature under a hydrogen balloon for 4 hours. The reaction was filtered through celite and the solvent removed under reduced pressure to yield Compound III (4.11 g, 10.0 mmol, 77% yield), ES (+) MS m/e=410 (M+1) which was used without further purification.

d) Compound III (4.11 g, 10.0 mmol) was dissolved in 30 mL DCM and mixed with imidazol-1-yl-oxo-acetic acid tert-butyl ester (1.97 g, 10.04 mmol) in 20 mL DCM. The reaction was stirred at ambient temperature for 15 hours at which point the DCM was removed under reduced pressure and the residue redissolved in 50 mL EtOAc. The reaction was washed with 2×10 mL 1 M NaHSO$_4$, 2×10 mL saturated NaHCO$_3$, 10 mL brine, dried over anhydrous Na$_2$SO$_4$, filtered, and the solvent removed under reduced pressure to yield Compound IV (4.68, 8.70 mmol, 87%), ES (+) MS m/e=560 (M+Na) which was used without further purification.

e) Compound IV (1.0 g, 1.86 mmol) was dissolved in 2 mL MeOH and lithium hydroxide (0.045 g, 1.86 mmol) in 2 mL water was added. The solution was stirred for 0.5 hours and then flooded with 30 mL 1 M NaHSO$_4$ and extracted with 3×10 mL EtOAc. The combined organic layers were washed with 15 mL 1 M NaHSO$_4$, 15 mL brine, dried over anhydrous Na$_2$SO$_4$, filtered, and the solvent removed under reduced pressure. The crude residue was then dissolved in 5 mL 4:1 Benzene:MeOH and (trimethylsilyl)diazomethane (0.229 mL, 0.457 mmol) was added drop wise. The solvents were removed and the residue redissolved in 10 mL DCM. 1 mL TFA was added and the solution stirred at ambient temperature for 10 minutes. The solvent was removed under reduced pressure to yield Compound V in quantitative yield, ES (+) MS m/e=396 (M+H) which was used without further purification.

f) Compound V (0.157 g, 0.398 mmol) was dissolved in 2 mL DCM and triethylamine (TEA) (0.166 mL, 1.19 mmol) was added followed by acetic anhydride (0.038 mL, 0.398 mmol). The reaction was stirred for 1 hour at ambient temperature, flooded with 20 mL EtOAc, washed with 2×5 mL 1 M NaHSO$_4$, 2×5 mL saturated NaHCO$_3$, 5 mL brine, dried over anhydrous Na$_2$SO$_4$, filtered, and the solvent removed under reduced pressure to yield Compound VI (0.127 g, 0.290 mmol, 73%), ES (+) MS m/e=460 (M+Na) which was used without further purification.

g) Compound VI (0.127 g. 0.290 mmol) was dissolved in 2.5 mL DCM and 2.5 mL TFA was added and the reaction stirred at ambient temperature for 3 hours. The solvent was removed under reduced pressure and the residue was redissolved in 2.5 mL MeOH. Lithium hydroxide (0.014 g, 0.58 mmol) in 2.5 mL water was added and the reaction stirred for 1 hour. The solvent was removed and the crude residue purified by reverse-phase preparatory HPLC to afford Compound VII (0.007 g, 0.019 mmol, 7%), ES (+) MS: m/e=368 (M+1).

EXAMPLE 22

This example describes the synthesis of the compound below

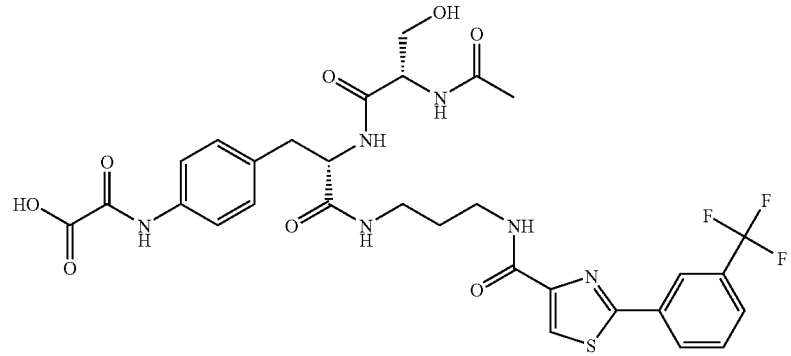

which was made according to Scheme K

SCHEME K

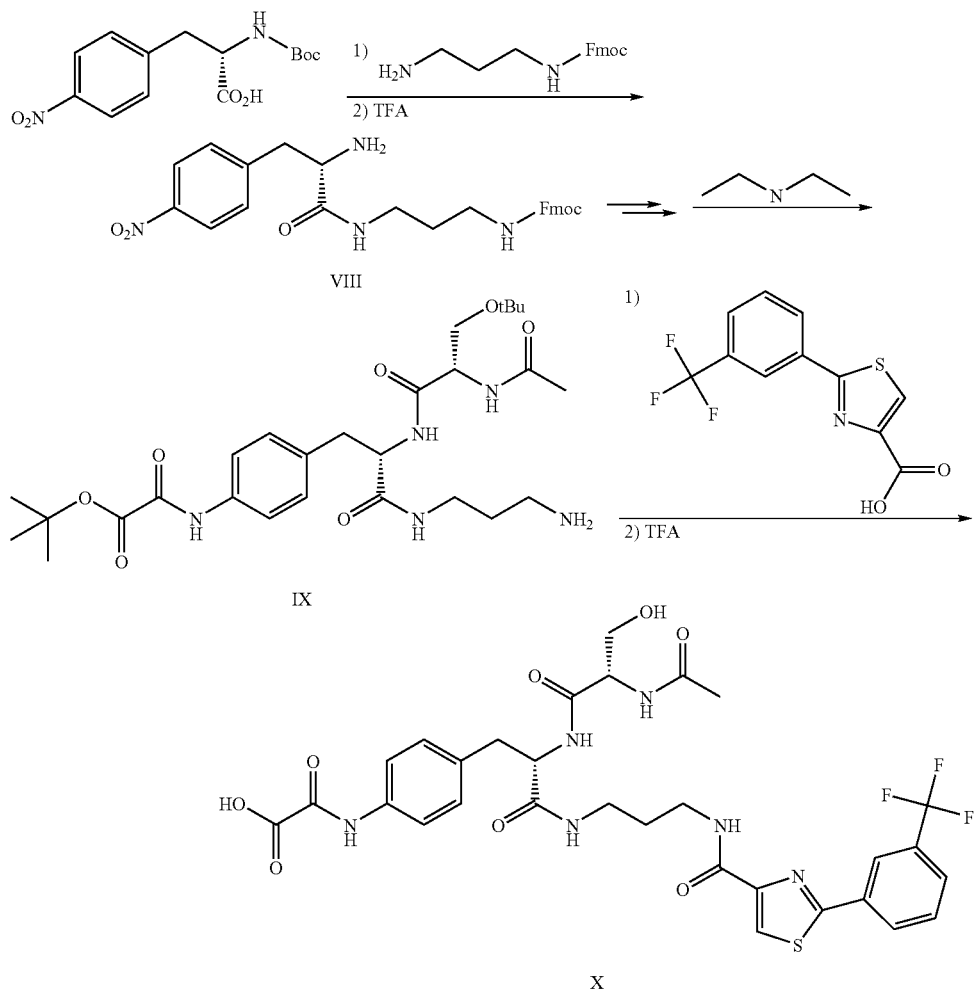

a) Compound VIII was prepared according to the method of Example 21b followed by TFA deprotection (Example 21a) except starting from N-1-Fmoc-1,3-diaminopropane HCl instead of Compound I and using Boc-4-nitro-D-phenylalanine instead of Boc-O-(t-butyl ether)-L-serine, ES (+) MS m/e=525 (M+Na)

b) Compound IX was prepared by treating Compound VIII according to the methods of Example 21 b, e (TFA deprotection only), f, c, and d. The resulting residue was then dissolved in 5 mL DCM and 5 mL diethylamine (DEA) was added. The solution was stirred at ambient temperature for 16 hours, the solvent removed under reduced pressure and the residue purified by silica gel chromatography using $CHCl_3$: 2 M $NH_3$ in MeOH 9:1, yielding Compound IX (0.173 g, 0.306 mmol, 38% yield), ES (+) MS m/e=550 (M+1).

c) Compound X was prepared by treating Compound IX according to the method of Example 21b followed by the TFA deprotection and HPLC purification portions of 21 h except starting from 2-[3-(trifluoromethyl)phenyl]-1,3-thiazole-4-carboxylic acid instead of Boc-O-(t-butyl ether)-L-serine, ES (+) MS m/e=693 (M+H).

EXAMPLE 23

This example describes the synthesis of the compound below

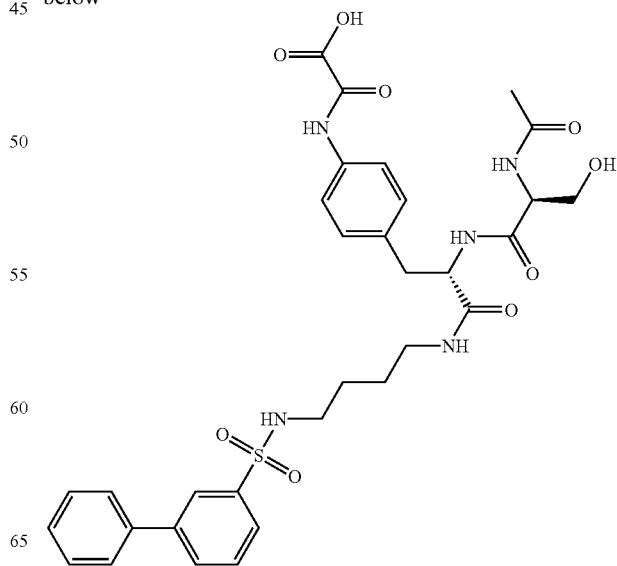

which was made according to Scheme L

SCHEME L

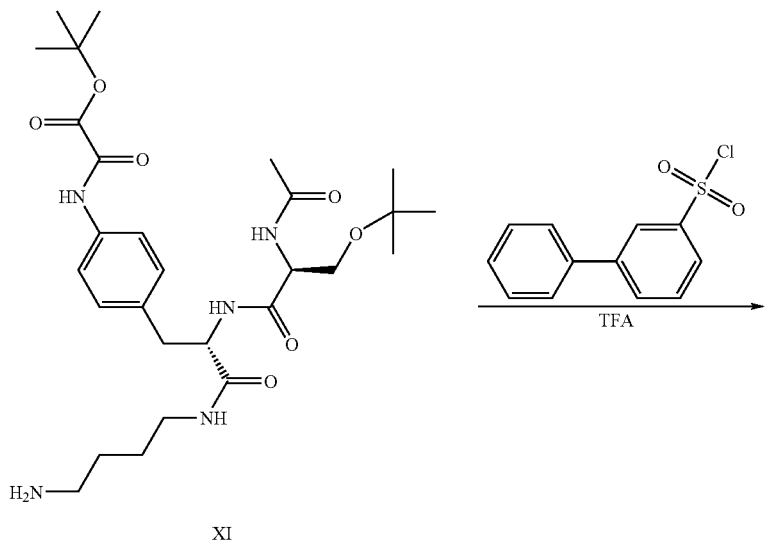

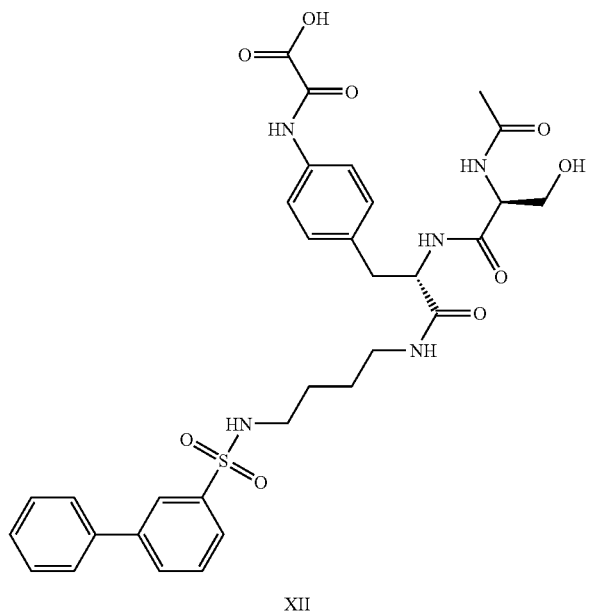

a) Compound XI was prepared according to the methods of Examples 22a–b except starting from N-1-Fmoc-1,4-diaminobutane HCL instead of N-1-Fmoc-1,3-diaminopropane HCL, ES (+) MS m/e 564 (M+H).

b) Compound XI (0.173 g, 0.307 mmol) was dissolved in 1 mL DCM, DIEA (0.043 mL, 0.307 mmol) was added and this solution was added to 4-biphenylsulfonyl chloride (0.078 g, 0.307 mmol) dissolved in 1 mL DCM. This mixture was stirred at ambient temperature for 0.5 hour at which point it was flooded with 20 mL DCM, washed with 2×5 mL 1 M NaHSO$_4$, 5 mL brine, dried over anhydrous Na$_2$SO$_4$, filtered, and the solvent removed under reduced pressure. The residue was dissolved in 2 mL DCM, 2 mL TFA was added and the reaction stirred for 0.5 hour. The solvent was removed and the crude residue purified by reverse-phase preparatory HPLC to afford Compound XII (0.025 g, 0.037 mmol, 12%), ES (+) MS: m/e=668 (M+1).

EXAMPLE 24

This example describes the synthesis of the compound below

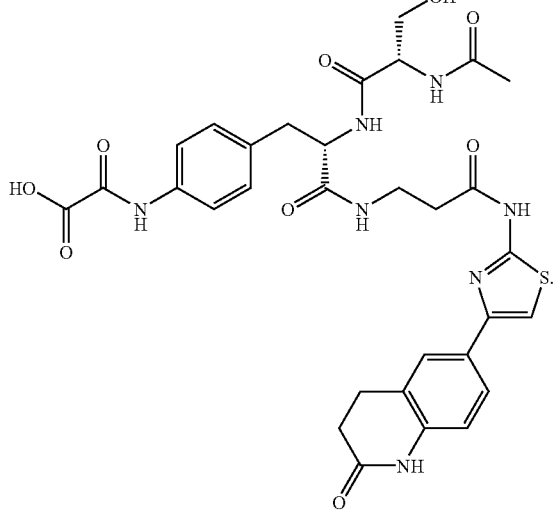

This compound was prepared essentially according to the methods of Example 22 except starting from β-alanine benzyl etser-p-toluenesulfonate salt instead of N-1-Fmoc-1, 3-diaminoproprionic HCl. ES (+) MS m/e=680 (M+H).

EXAMPLE 25

This example describes the synthesis of the compound below

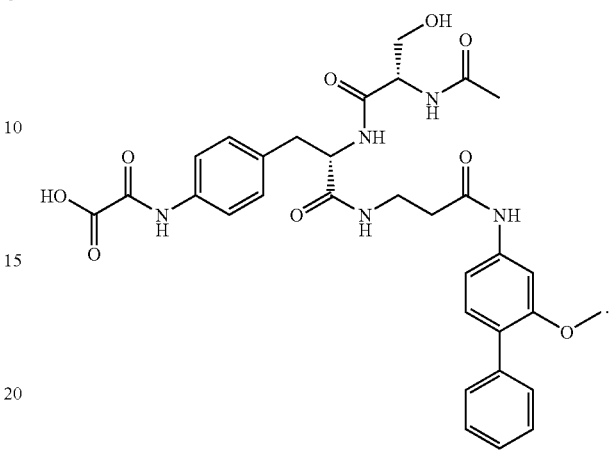

This compound was prepared according to the method of Example 24 except using 4-phenyl-M-anisidine hydrochloride instead of 6-(2-amino-1,3-thiazole-4-yl)-1,2,3,4-tetrahydroquinolin-2-on. ES (+) MS m/e=634 (M+H).

EXAMPLE 26

This example describes the synthesis of the following compound

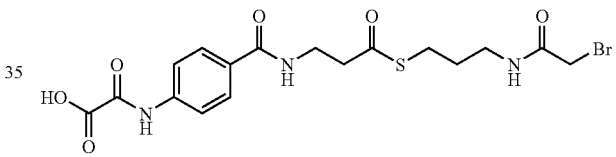

which was synthesized according to Scheme M and the procedure below.

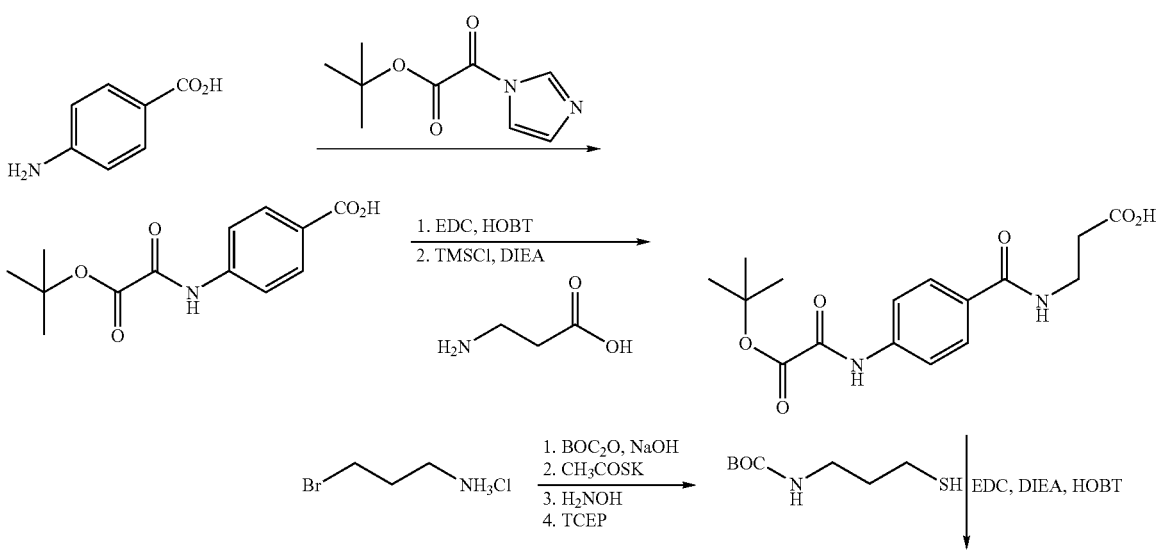

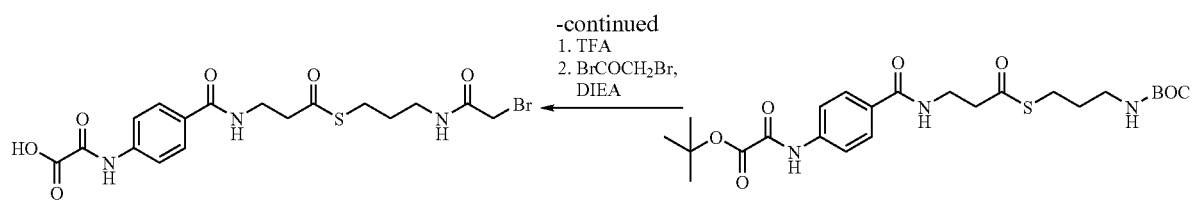

Commercially available 4-aminobenzoic acid (2.24 g, 16.3 mmol) was suspended in dichloromethane ("DCM", 40 ml) under nitrogen and diisopropylethylamine ("DIEA", 2.9 ml, 16.6 mmol) was added with stirring. After 20 minutes most of the solid had dissolved, and the oxalamating reagent was added (see e.g., Jonathan S. Nimitz and Harry S. Mosher, *J. Org. Chem.* 46: 211–213 (1981)). After one hour the reaction was diluted with 60 ml DCM, rinsed with 3×50 ml 1 M NaHSO$_4$ and 50 ml brine, and evaporated to dryness to yield an off-white solid (3.34 g, 12.6 mmol, 77%, (+) MS m/z=288 (M+Na)).

This acid (0.440 g, 1.66 mmol) was mixed with 1-ethyl-(3-dimethylaminopropyl)carbodiimide hydrochloride ("EDC", 0.328 g, 1.71 mmol) and 1-hydroxybenzotriazole ("HOBT", 0.225 g, 1.71 mmol) and dissolved in dry dimethylformamide ("DMF", 5 ml) and stirred at room temperature. Meanwhile, β-alanine was suspended in dry DCM (10 ml) and DIEA (1.4 ml, 8.0 mmol) and trimethylsilyl chloride ("TMSCl", 1.0 ml, 7.9 mmol) were added and the solution refluxed at 50° C. for one hour to yield a homogeneous golden solution; This was added to the activated acid along with 5 ml more DMF. The reaction was allowed to proceed for 30 minutes at which time it was flooded with 100 ml EtOAc, rinsed with 4 times 50 ml 1 M NaHSO4 and 50 ml brine, dried over sodium sulfate, evaporated to dryness, and purified by flash chromatography using 95:5:1 DCM:MeOH:AcOH. The product-containing fractions were coevaporated from toluene to remove acetic acid and dried to yield a white solid (0.465 g, 1.38 mmol, 83%, (+) MS m/z=337 (M+H)) consisting of product as well as residual HOBT.

The thiol was synthesized by mixing 3-aminopropylbromide hydrobromide (3.98 g, 18.2 mmol) with BOC anhydride (4.01 g, 18.4 mmol), dissolving the mixture in 25 ml water, and adding 18 ml of 1 N NaOH in water. After stirring for 18 hours the reaction was extracted with 100 ml EtOAc and the organic layer rinsed with 3×50 ml 1 M NaHSO4 and 50 ml brine, dried over sodium sulfate, filtered, and evaporated to dryness to yield the product bromide as a pale yellow syrup (3.98 g, 16.7 mmol, 92%, (+) MS m/z=260/262 (M+Na)). This material (0.958 g, 4.02 mmol) was dissolved in 5 ml dry DMF and treated with potassium thioacetate (0.484 g, 4.24 mmol) and 5 ml more DMF and allowed to react under nitrogen for 2 days. To this was then added hydroxylamine (1 ml of 50% in water, 16.3 mmol) and the reaction allowed to proceed for 2 hours, at which point it was flooded with 80 ml EtOAc, rinsed with 2×40 ml saturated sodium bicarbonate, 2×40 ml 1 M NaHSO4, and 40 ml brine, dried over sodium sulfate, filtered, and evaporated to dryness to yield a 1:2 mixture of thiol:disulfide as a pale yellow syrup (0.719 g, 3.76 mmol, 93%, (+) MS m/z=403 (M+Na)). This was fully reduced to the free thiol by dissolving it (0.499 mg, 1.31 mmol) in 5 ml methanol and adding a solution of tris(2-carboxyethyl)phosphine hydrochloride in 3 ml 1 M NaOH in water, along with another 5 ml methanol. After stirring for one hour under nitrogen, the reaction was flooded with 50 ml EtOAc, rinsed with 2×25 ml saturated sodium bicarbonate, 25 ml 1 M NaHSO4, and 25 ml brine, dried over sodium sulfate, filtered, and evaporated to dryness to yield product thiol as an almost colorless oil (0.466 g, 2.44 mmol, 93%, (+) MS m/z=214 (M+Na)).

The thiol was conjugated to the acid as follows. First, the acid (268 mg, 0.796 mmol) was mixed with EDC (162 mg, 0.845 mmol) and HOBT (108 mg, 799 mmol) and dissolved in 5 ml dry DMF. The thiol (160 mg, 0.836 mmol) was added along with another 3 ml dry DMF. Finally, DIEA (0.3 ml, 1.72 mmol) was added and the reaction allowed to proceed for 45 minutes. The reaction was then flooded with 50 ml EtOAc, rinsed with 2×25 ml 1 M NaHSO4, 2×25 ml saturated sodium bicarbonate, and 25 ml brine, dried over sodium sulfate, filtered, evaporated to dryness, and purified by flash chromatography using 50:50 EtOAc:hexane to yield pure thioester as a white foam (186 mg, 0.365 mmol, 46%, (+) MS m/z=510 (M+H)).

This material (58 mg, 0.114 mmol) was dissolved in 4 ml dry DCM and TFA (4 ml) was added. The reaction was allowed to stir at room temperature for 30 minutes, then evaporated to dryness. This material was then resuspended in 3 ml dry THF and bromoacetyl bromide (0.03 ml, 0.345 mmol) and DIEA (0.1 ml, 0.574 mmol) was added, followed by 3 ml dry DMF. After 30 minutes the reaction was flooded with 50 ml EtOAc, rinsed with 3×25 ml 1 M NaHSO4 and 25 ml brine, dried over sodium sulfate, filtered, evaporated to dryness, and purified by reverse phase chromatography to yield the desired product (5.2 mg, 0.011 mmol, 10%, (+) MS m/z=496/498 (M+Na)).

EXAMPLE 27

This example describes the synthesis of the following compound

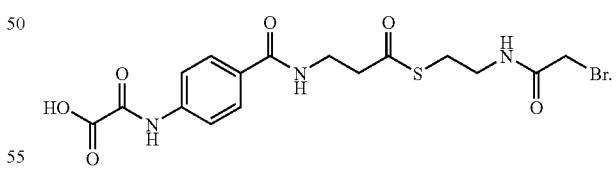

This compound was synthesized according to the procedure in Example 3 except for using commercially available N-BOC-cysteamine as the thiol instead of

BOC-NH-CH$_2$CH$_2$CH$_2$-SH (ES (+) MS m/z=460/462 (M+H)).

EXAMPLE 28

This example describes the procedure for modifying R47C mutant of PTP-1B with the extender whose synthesis was described in Example 27. This extender comprises a first functionality, a cleavable linker with a latent second functionality and a phosphotyrosine mimetic.

Figure 4:
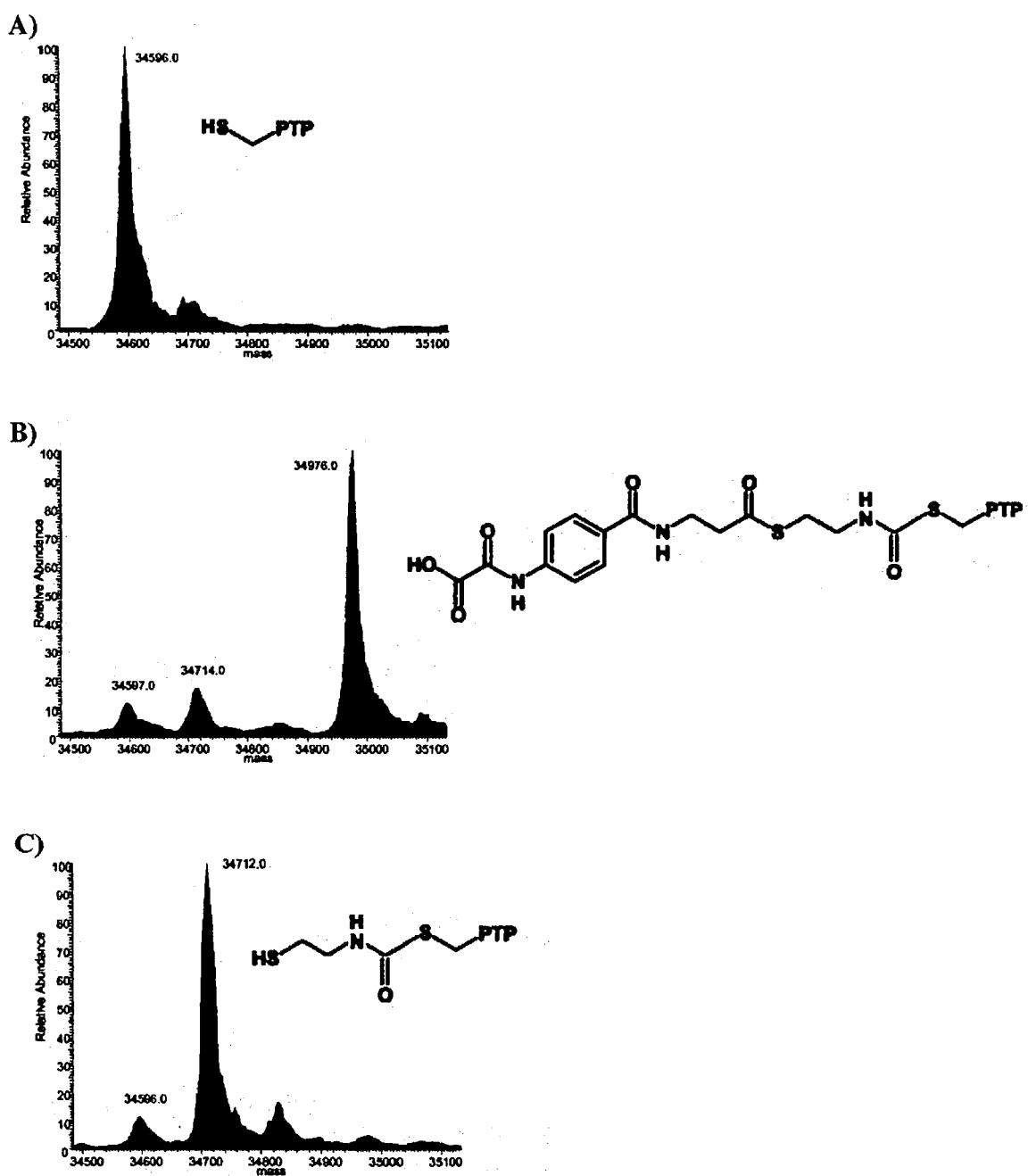
FIG. 4 is the mass spectrum of the R47C mutant of PTP-1B that is modified with an extender comprising a first functionality, a cleaveable linker with a latent second functionality and a phosphotyrosine mimetic.

Freshly prepared or freshly unfrozen (from −80 deg. C.) aliquots of PTP-1B R47C (2×1.8 ml, 1.7 mg/ml) were treated with 0.02 ml of freshly prepared or freshly thawed 1 M dithiothreitol ("DTT"), concentrated in Ultrafree 4 ml 5000 MWCO units (Millipore), and exchanged into 100 mM Tris buffer (pH 8) using a Nap-5 column (Pharmacia Biotech). To this solution (1 ml) was added 0.02 ml of 25 mM extender in dimethylsulfoxide (DMSO) thereby forming a PTP-1B-extender complex. The solution was carefully but thoroughly mixed and then centrifuged briefly to pellet any precipitate. The reaction was allowed to proceed for 15 minutes. After 15 minutes, excess extender was quenched with 0.01 ml 1 M DTT and the thioester was deprotected (thereby exposing the second functionality, the thiol) with 0.1 ml of 0.5 M hydroxylamine hydrochloride in 1 M Tris buffer (pH 8) thereby forming a modified PTP-1B-extender complex. The deprotection was allowed to proceed for at least 5 hours, after which another 0.02 ml 1 M DTT was added, the solution was concentrated in Ultrafree-4 ml 5000 MWCO units (Millipore), and then purified into 100 mM Tris 8 buffer via Nap-5. The resulting protein was cleanly and quantitatively modified as shown in FIG. 4.

EXAMPLE 29

This example describes two illustrative assays to measure the activity of PTP-1B.

pNPP Assay: This assay is performed with 5 mM para-nitrophenyl-phosphate (pNPP) substrate at pH 7 in a 100 ul total reaction volume. Upon addition of 750 ng PTP, the reaction is measured over 15 minutes (OD405–OD655) and IC50s determined using 5 minute and 15 minute rates. Compounds are tested at 7 concentrations using 3-fold dilutions. 1 mM pNPP is used for screening. $V_{max}$ and $K_m$ are determined to verify competitive inhibition according to classical Michaelis-Menten kinetics.

Insulin Receptor Kinase (IRK) peptide assay: The IRK peptide corresponds to the triphosphorylated segment of the insulin receptor kinase activation loop. This assay is performed using 100 uM peptide, 0.5 pmol of PTP-1B protein at pH 7 for 15 minutes at room temperature. The malachite green reagent, consisting of 3:1 malachite green:ammonium molybdate with 0.5% Tween 20, is added and the mixture incubated at room temperature for 30 minutes. Absorbance at 655 nm is measured. Compounds are tested at 7 concentrations using 3-fold dilutions.

---

What is claimed is:

1. A method for identifying a candidate ligand comprising:
   a) providing a PTP (protein tyrosine phosphatase) having a reactive thiol located outside of its active site;
   b) contacting the PTP with an extender thereby forming a PTP-extender complex wherein the extender comprises a first functionality that forms a covalent bond with the reactive thiol and a second functionality that is capable of forming a disulfide bond;
   c) contacting the PTP-extender complex with a candidate ligand that comprises a group that is capable of forming a disulfide bond with the second functionality;
   d) forming a disulfide bond between the PTP-extender complex and the candidate ligand thereby forming a PTP-extender-ligand conjugate; and,
   e) identifying the candidate ligand present in the PTP-extender-ligand conjugate.

2. The method of claim 1 wherein the reactive thiol on PTP is a naturally occurring -SH from a cysteine that is part of the naturally occurring protein sequence.

3. The method of claim 1 wherein the reactive thiol on the PTP is from a cysteine where mutagenesis was used to replace a naturally occurring amino acid.

4. The method of claim 1 wherein the reactive thiol is masked as a disulfide.

5. The method of claim 1 wherein the covalent bond between the reactive thiol and the first functionality is an irreversible covalent bond.

6. The method of claim 1 wherein the covalent bond between the reactive thiol and the first functionality is a reversible covalent bond.

7. The method of claim 1 wherein the PTP-extender complex is contacted with a candidate ligand in the presence of a reducing agent.

8. The method of claim 7 wherein the reducing agent is selected from the group consisting of: cysteine, cysteamine, dithiothreitol, dithioerythritol, glutathione, 2-mercaptoethanol, 3-mercaptoproprionic acid, a phosphine such as tris-(2-carboxyethylphosphine), and sodium borohydride.

9. The method of claim 1 wherein the extender is selected from the group consisting of

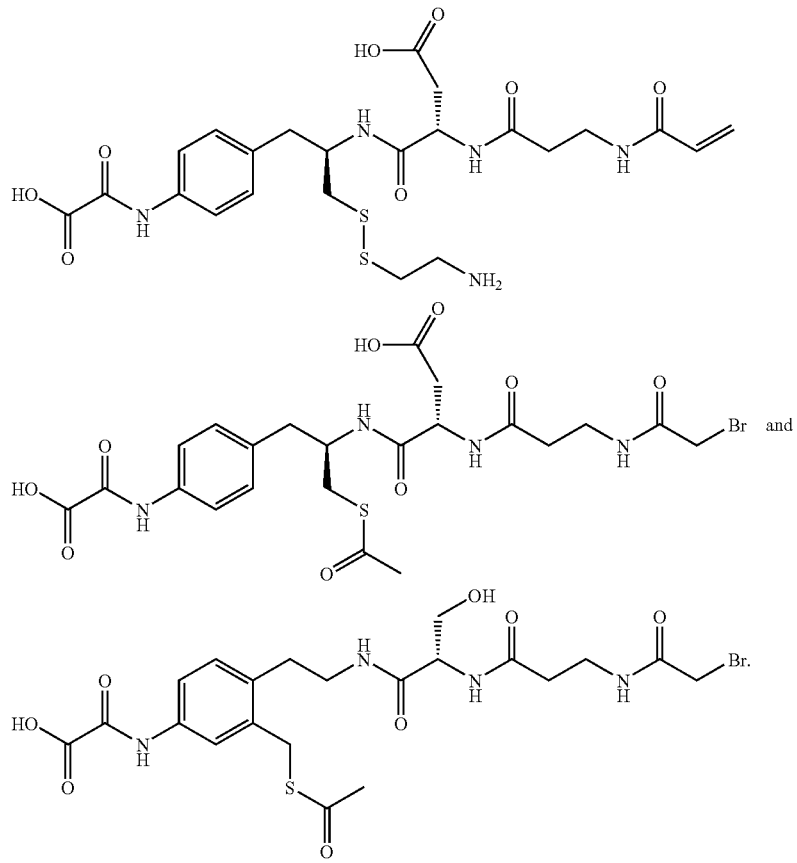

10. A method of identifying a candidate ligand comprising:
   a) providing a PTP (protein tyrosine phosphatase) having an active site, a cysteine located in its active site and a reactive thiol located outside of the active site;
   b) contacting the PTP with an extender thereby forming a PTP-extender complex, the extender comprising a first functionality and a latent second functionality, a cleavable linker and a binding determinant comprising a phosphotyrosine or a phosphotyrosine mimetic wherein the first functionality forms a first covalent bond with the reactive thiol and the binding determinant binds to the active site;
   c) cleaving the extender at the cleavable linker thereby forming a modified PTP-extender complex thereby exposing the second functionality and releasing the binding determinant from the active site;
   d) contacting the modified PTP-extender complex with a candidate ligand that comprises a group that is capable of forming a second covalent bond with the second functionality;
   e) forming a second covalent bond between the modified PTP-extender complex and the candidate ligand thereby forming a PTP-extender-ligand conjugate; and,
   f) identifying the candidate ligand present in the PTP-extender-ligand conjugate.

11. The method of claim 10 wherein the reactive thiol on PTP is a naturally occurring —SH from a cysteine that is part of the naturally occurring protein sequence.

12. The method of claim 10 wherein the reactive thiol on the PTP is from a cysteine where mutagenesis was used to replace a naturally occurring amino acid.

13. The method of claim 10 wherein the reactive thiol is masked as a disulfide.

14. The method of claim 10 wherein the covalent bond between the reactive thiol and the first functionality is an irreversible covalent bond.

15. The method of claim 10 wherein the covalent bond between the reactive thiol and the first functionality is a reversible covalent bond.

16. The method of claim 10 wherein PTP-extender complex is contacted with a candidate ligand in the presence of a reducing agent.

17. The method of claim 16 wherein the reducing agent is selected from the group consisting of: cysteine, cysteamine, dithiothreitol, dithioerythritol, glutathione, 2-mercaptoethanol, 3-mercaptoproprionic acid, a phosphine such as tris-(2-carboxyethylphosphine), and sodium borohydride.
18. The method of claim 10 wherein the extender is of the formula
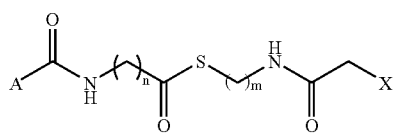
where A is selected from the group consisting of:
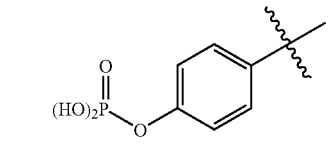
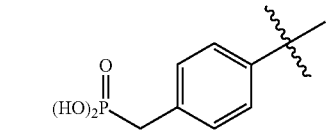
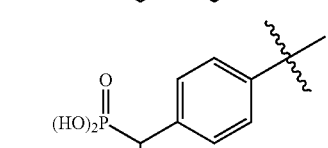
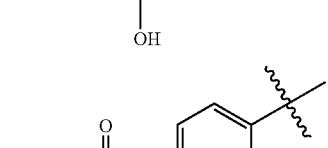
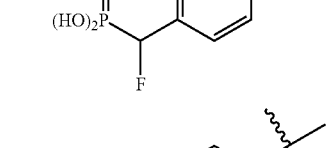
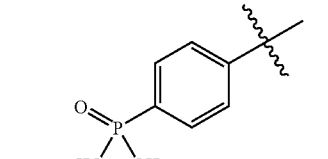
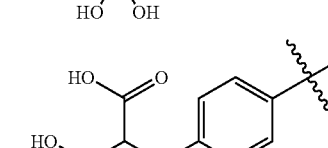
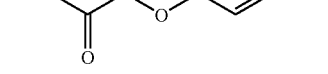
-continued
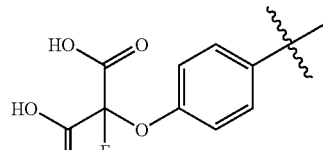
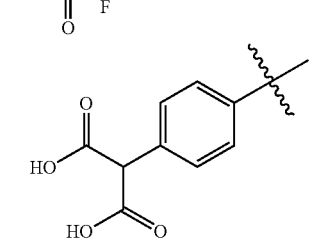
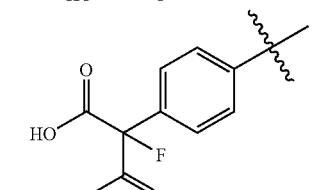
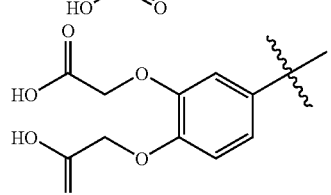
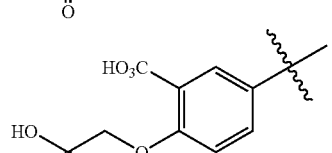
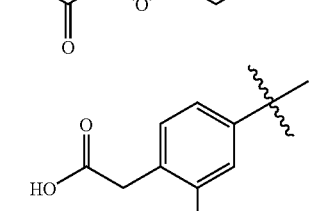
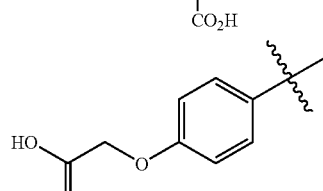
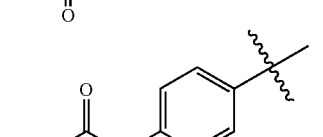
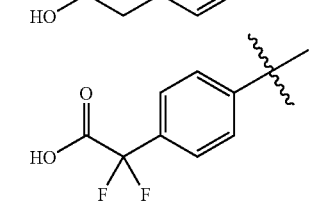

-continued
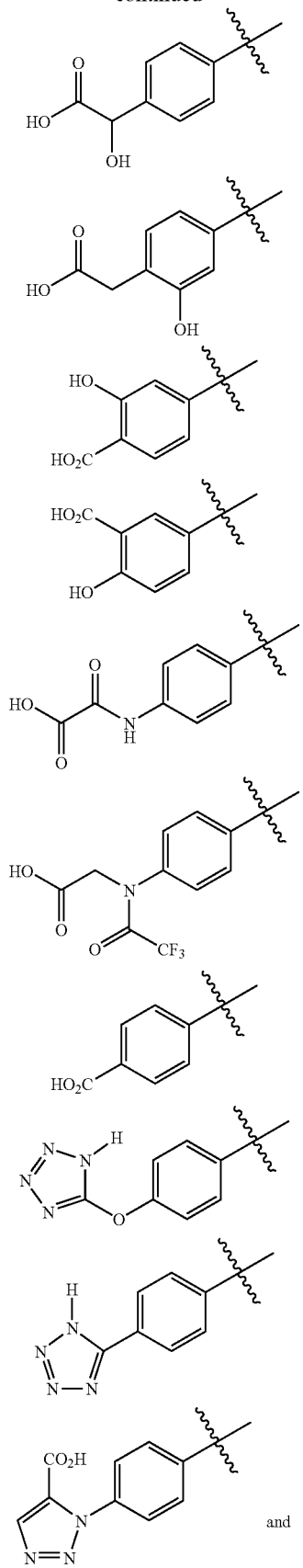
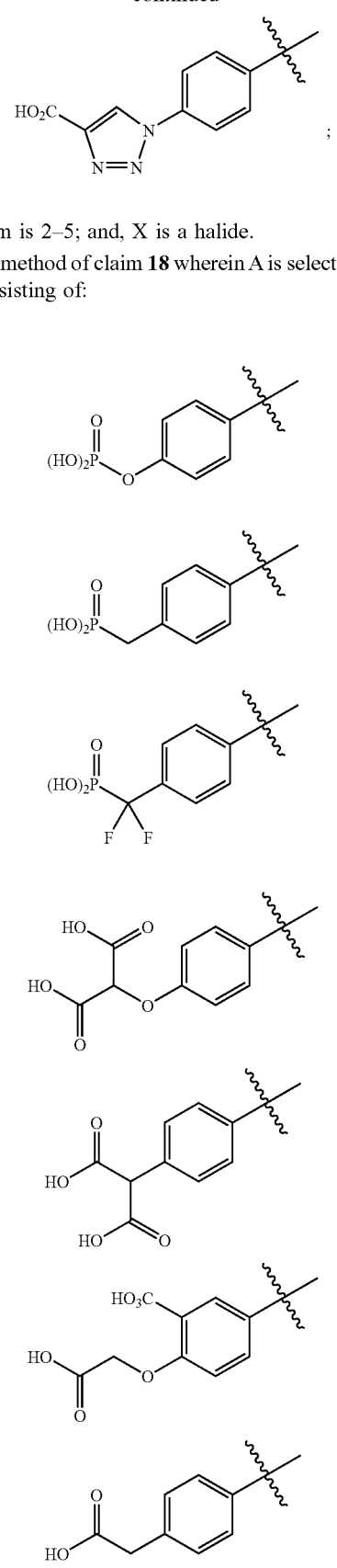
n is 1–5; m is 2–5; and, X is a halide.
19. The method of claim 18 wherein A is selected from the group consisting of:

-continued
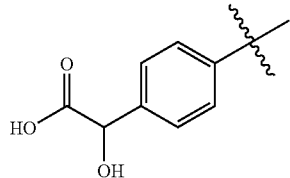 and
-continued
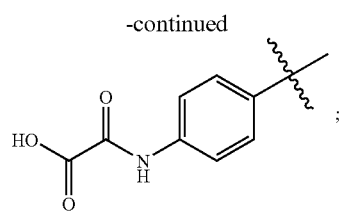
n and m are independently 2 or 3; and X is bromide.
* * * * *

SEQUENCE LISTING

```
<160> NUMBER OF SEQ ID NOS: 9

<210> SEQ ID NO 1
<211> LENGTH: 30
<212> TYPE: DNA
<213> ORGANISM: Homo sapiens

<400> SEQUENCE: 1
gcccatatgg agatggaaaa ggagttcgag                                    30

<210> SEQ ID NO 2
<211> LENGTH: 40
<212> TYPE: DNA
<213> ORGANISM: Homo sapiens

<400> SEQUENCE: 2
gcgacgcgaa ttcttaattg tgtggctcca ggattcgttt                         40

<210> SEQ ID NO 3
<211> LENGTH: 34
<212> TYPE: DNA
<213> ORGANISM: Homo sapiens

<400> SEQUENCE: 3
tgccggaatt ccttagtcct cgtgggaaag ctcc                               34

<210> SEQ ID NO 4
<211> LENGTH: 27
<212> TYPE: DNA
<213> ORGANISM: Homo sapiens

<400> SEQUENCE: 4
cttggccact ctagatggga agtcact                                       27
```

<210> SEQ ID NO 5
<211> LENGTH: 27
<212> TYPE: DNA
<213> ORGANISM: Homo sapiens

<400> SEQUENCE: 5
ccaaaagtga ccggctgtgt taggcaa                                              27

<210> SEQ ID NO 6
<211> LENGTH: 27
<212> TYPE: DNA
<213> ORGANISM: Homo sapiens

<400> SEQUENCE: 6
gggactgacg tcacagtacc tatttcg                                              27

<210> SEQ ID NO 7
<211> LENGTH: 298
<212> TYPE: PRT
<213> ORGANISM: Homo sapiens

<400> SEQUENCE: 7

```
Met Glu Met Glu Lys Glu Phe Glu Gln Ile Asp Lys Ser Gly Ser Trp
 1               5                  10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270
```

```
Ala Val Ile Glu Gly Ala Lys Phe Ile Met Gly Asp Ser Ser Val Gln
        275                 280                 285

Asp Gln Trp Lys Glu Leu Ser His Glu Asp
        290                 295

<210> SEQ ID NO 8
<211> LENGTH: 296
<212> TYPE: PRT
<213> ORGANISM: Homo sapiens

<400> SEQUENCE: 8

Met Pro Thr Thr Ile Glu Arg Glu Phe Glu Glu Leu Asp Thr Gln Arg
  1               5                  10                  15

Arg Trp Gln Pro Leu Tyr Leu Glu Ile Arg Asn Glu Ser His Asp Tyr
             20                  25                  30

Pro His Arg Val Ala Lys Phe Pro Glu Asn Arg Asn Arg Asn Arg Tyr
         35                  40                  45

Arg Asp Val Ser Pro Tyr Asp His Ser Arg Val Lys Leu Gln Asn Ala
     50                  55                  60

Glu Asn Asp Tyr Ile Asn Ala Ser Leu Val Asp Ile Glu Glu Ala Gln
 65                  70                  75                  80

Arg Ser Tyr Ile Leu Thr Gln Gly Pro Leu Pro Asn Thr Cys Cys His
                 85                  90                  95

Phe Trp Leu Met Val Trp Gln Gln Lys Thr Lys Ala Val Val Met Leu
            100                 105                 110

Asn Arg Ile Val Glu Lys Glu Ser Val Lys Cys Ala Gln Tyr Trp Pro
        115                 120                 125

Thr Asp Asp Gln Glu Met Leu Phe Lys Glu Thr Gly Phe Ser Val Lys
    130                 135                 140

Leu Leu Ser Glu Asp Val Lys Ser Tyr Tyr Thr Val His Leu Leu Gln
145                 150                 155                 160

Leu Glu Asn Ile Asn Ser Gly Glu Thr Arg Thr Ile Ser His Phe His
                165                 170                 175

Tyr Thr Thr Trp Pro Asp Phe Gly Val Pro Glu Ser Pro Ala Ser Phe
            180                 185                 190

Leu Asn Phe Leu Phe Lys Val Arg Glu Ser Gly Ser Leu Asn Pro Asp
        195                 200                 205

His Gly Pro Ala Val Ile His Cys Ser Ala Gly Ile Gly Arg Ser Gly
    210                 215                 220

Thr Phe Ser Leu Val Asp Thr Cys Leu Val Leu Met Glu Lys Gly Asp
225                 230                 235                 240

Asp Ile Asn Ile Lys Gln Val Leu Leu Asn Met Arg Lys Tyr Arg Met
                245                 250                 255

Gly Leu Ile Gln Thr Pro Asp Gln Leu Arg Phe Ser Tyr Met Ala Ile
            260                 265                 270

Ile Glu Gly Ala Lys Cys Ile Lys Gly Asp Ser Ser Ile Gln Lys Arg
        275                 280                 285

Trp Lys Glu Leu Ser Lys Glu Asp
        290                 295

<210> SEQ ID NO 9
<211> LENGTH: 296
<212> TYPE: PRT
<213> ORGANISM: Homo sapiens

<400> SEQUENCE: 9
```

-continued

```
Pro Ile Thr Asp Leu Ala Asp Asn Ile Glu Arg Leu Lys Ala Asn Asp
 1               5                  10                  15

Gly Leu Lys Phe Ser Gln Glu Tyr Glu Ser Ile Asp Pro Gly Gln Gln
                20                  25                  30

Phe Thr Trp Glu Asn Ser Asn Leu Glu Val Asn Lys Pro Lys Asn Arg
            35                  40                  45

Tyr Ala Asn Val Ile Ala Tyr Asp His Ser Arg Val Ile Leu Thr Ser
        50                  55                  60

Ile Asp Gly Val Pro Gly Ser Asp Tyr Ile Asn Ala Asn Tyr Ile Asp
 65                  70                  75                  80

Gly Tyr Arg Lys Gln Asn Ala Tyr Ile Ala Thr Gln Gly Pro Leu Pro
                85                  90                  95

Glu Thr Met Gly Asp Phe Trp Arg Met Val Trp Glu Gln Arg Thr Ala
            100                 105                 110

Thr Val Val Met Met Thr Arg Leu Glu Glu Lys Ser Arg Val Lys Cys
        115                 120                 125

Asp Gln Tyr Trp Pro Ala Arg Gly Thr Glu Thr Cys Gly Leu Ile Gln
130                 135                 140

Val Thr Leu Leu Asp Thr Val Glu Leu Ala Thr Tyr Thr Val Arg Thr
145                 150                 155                 160

Phe Ala Leu His Lys Ser Gly Ser Ser Glu Lys Arg Glu Leu Arg Gln
                165                 170                 175

Phe Gln Phe Met Ala Trp Pro Asp His Gly Val Pro Glu Tyr Pro Thr
            180                 185                 190

Pro Ile Leu Ala Phe Leu Arg Arg Val Lys Ala Cys Asn Pro Leu Asp
        195                 200                 205

Ala Gly Pro Met Val Val His Cys Ser Ala Gly Val Gly Arg Thr Gly
    210                 215                 220

Cys Phe Ile Val Ile Asp Ala Met Leu Glu Arg Met Lys His Glu Lys
225                 230                 235                 240

Thr Val Asp Ile Tyr Gly His Val Thr Cys Met Arg Ser Gln Arg Asn
                245                 250                 255

Tyr Met Val Gln Thr Glu Asp Gln Tyr Val Phe Ile His Glu Ala Leu
            260                 265                 270

Leu Glu Ala Ala Thr Cys Gly His Thr Glu Val Pro Ala Arg Asn Leu
        275                 280                 285

Tyr Ala His Ile Gln Lys Leu Gly
290                 295
```